(12) United States Patent
Banerjee et al.

(10) Patent No.: US 10,081,800 B1
(45) Date of Patent: Sep. 25, 2018

(54) LACTONASE ENZYMES AND METHODS OF USING SAME

(71) Applicant: Fornia BioSolutions, Inc., Hayward, CA (US)

(72) Inventors: Goutami Banerjee, Hayward, CA (US); Jie Yang, Foster City, CA (US); Khin Oo, Daly City, CA (US); Xiyun Zhang, Fremont, CA (US); Eric Lin Hu, Milbrae, CA (US); Tatsuya Fukushima, Fremont, CA (US)

(73) Assignee: Fornia BioSolutions, Inc., Hayward, CA (US)

( * ) Notice: Subject to any disclaimer, the term of this patent is extended or adjusted under 35 U.S.C. 154(b) by 0 days.

(21) Appl. No.: 15/668,231

(22) Filed: Aug. 3, 2017

(51) Int. Cl.
*A61K 38/48* (2006.01)
*C12N 9/18* (2006.01)

(52) U.S. Cl.
CPC ..................... *C12N 9/18* (2013.01)

(58) Field of Classification Search
CPC ............... A61K 38/00; C12N 15/86
USPC .............. 424/94.6; 435/195, 252.3, 320.1; 536/23.2
See application file for complete search history.

(56) References Cited

FOREIGN PATENT DOCUMENTS

| EP | 3020814 A1 | 5/2016 |
|---|---|---|
| WO | WO 2014/167140 A1 | 10/2014 |

OTHER PUBLICATIONS

Arama, N. et al., "Macromolecular Inhibition of Quorum Sensing: Enzymes, Antibodies, and Beyond," Chem. Rev., 2011, 111, p. 195-208, Epub Nov. 18, 2010.
Cao, Y. et al., "Orally Administered Thermostable N-Acyl Homoserine Lactonase from *Bacillus* sp. Strain Al96 Attenuates *Aeromonas hydrophila* Infection in Zebrafish," Appl Environ Microbiol, Mar. 2012, Epub Jan. 13, 2012, p. 1899-1908; doi:10.1128/AEM.06139-11.
Chen, F. et al., "Quorum Quenching Enzymes and Their Application in Degrading Signal Molecules to Block Quorum Sending-Dependent Infection," Int J Mol Sci, Aug. 26, 2013, 14, 17477-17500; doi:10:3390/ijms140917477.
Czajkowski, R. et al., "Quenching of acyl-homoserine lactone-dependent quorum sensing by enzymatic disruption of signal molecules," Acta Biochim Pol, Epub Feb. 17, 2009, vol. 56 No. Jan. 2009, 1-16.
Dong, Y.-H. et al., "Quenching quorum-sensing-dependent bacterial infection by an N-acyl homoserine lactonase," Nature, Jun. 14, 2001, vol. 411, 813-817.
Grandclément, C. et al., "Quorum quenching: role in nature and applied developments," FEMS Microbiol Rev, Epub Oct. 1, 2015, 1-31; doi: 10,1093/femsre/fuv038.
Lade, H. et al., "Quorum Quenching Mediated Approaches for Control of Membrane Biofouling," Int J Biol Sci, May 14, 2014, vol. 10(5), 550-565; doi: 10,7150/ijbs.9028.
Oh, H.-S., et al. "Control of Membrane Biofouling in MBR for Wastewater Treatment by Quorum Quenching Bacteria Encapsulated in Microporous Membrane," Environ Sci Technol, Epub Apr. 3, 2012, 46, 4877-4884; doi: 10.1021/es204312u.
Tang, K. et al., "Quorum Quenching Agents: Resources for Antivirulence Therapy," Mar Drugs, May 30, 2014, 12(6), 3245-3282; doi: 10.3390/md12063245.
UniProtKB accession No. C6L826 (AHLL_MICTS), retrieved from the Internet on Jan. 23, 2018. http://www.uniprot.org/uniprot/C6L862.
International Search Report and Written Opinion for International Application No. PCT/US2018/032096 dated Jul. 30, 2018, 15 pages.
Wang, W.Z. et al., "AiiM, a Novel Class of N-Acylhomoserine Lactonase from the Leaf-Associated Bacterium *Microbacterium testaceum*", Applied and Environmental Microbiology, Apr. 15, 2010, vol. 76, No. 8, p. 2524-2530.
Last et al., "Fast, Continuous, and High-Throughput (Bio)Chemical Activity Assay for N-Acyl-L-Homoserine Lactone Quorum-Quenching Enzymes", Applied and Environmental Microbiology, May 6, 2016, vol. 82, No. 14, p. 4145-4154.
Fast et al., "The enzymes of bacterial census and censorship", Trends in Biochemical Sciences, Jan. 2, 2012 vol. 37, No. 1, p. 7-14.
Romero et al., "Patients on Quorum Quenching: Interfering with Bacterial Communication as a Strategy to Fight Infections", Recent Patents on Biotechnology, Apr. 1, 2012, vol. 6, No. 1, p. 2-12.

*Primary Examiner* — Tekchand Saidha
(74) *Attorney, Agent, or Firm* — Morgan, Lewis & Bockius LLP

(57) ABSTRACT

Novel lactonases are provided.

12 Claims, 14 Drawing Sheets
Specification includes a Sequence Listing.

Figure 1 Thermoactivity Profile of Lactonase
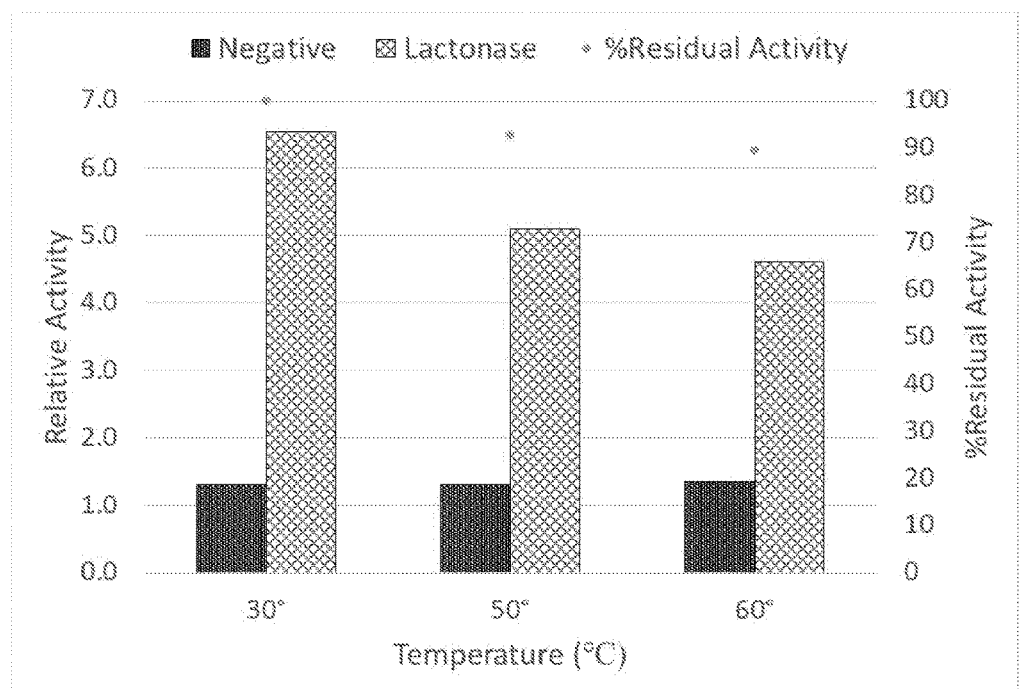

Figure 2  pH Profile of Lactonase
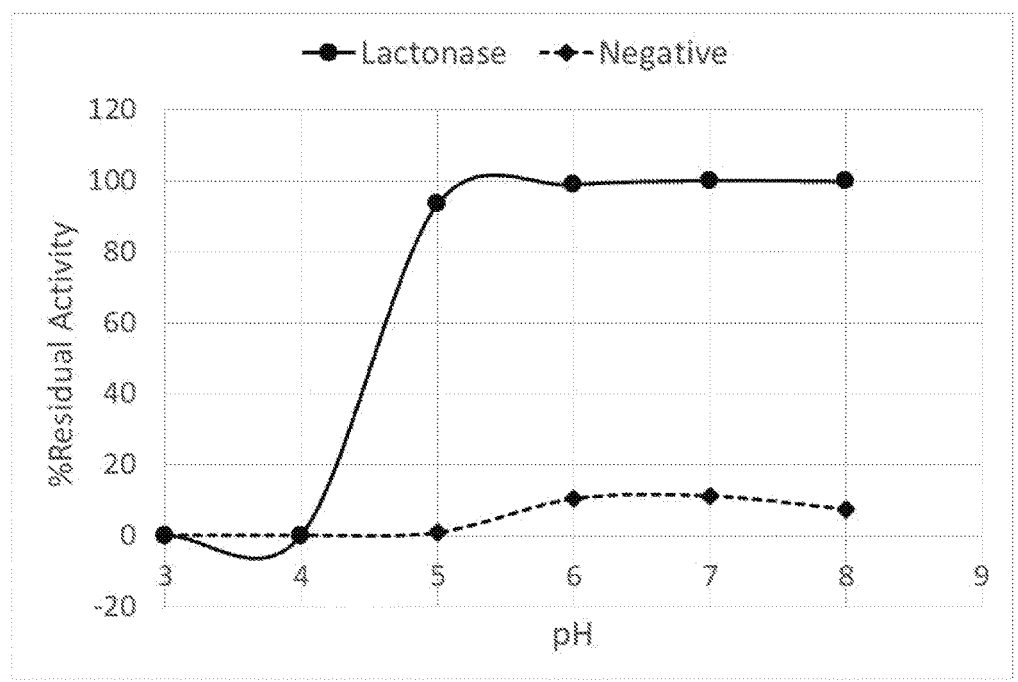

Figure 3  Thermostability Profile of Lactonase
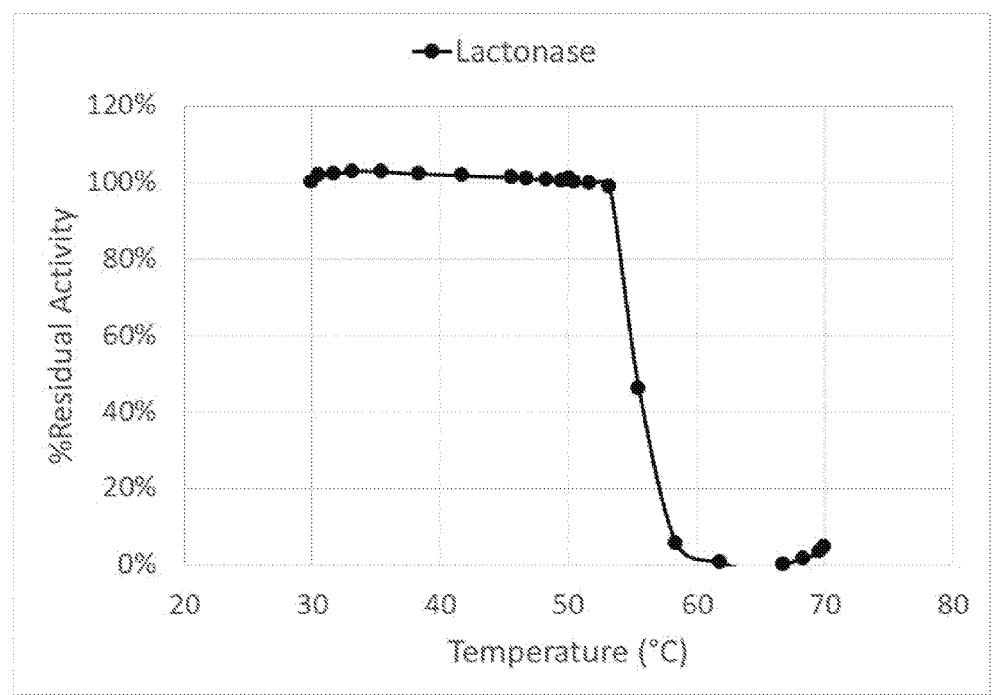

Figure 4A    G1 Improvement

| Colony Tracking Number | Activity Improvement<br><br>PF* AVG at pH7.2, 30°C, 30mins | Thermostability Improvement<br><br>PF* AVG at pH7.2, 30°C, 30mins after preincubation at pH7.2, 55.5°C for 10mins | pH Stability Improvement<br><br>PF* AVG at pH4.8, 30°C, 30mins | AA Mutations w.r.t. G1P (WT) | Alias |
|---|---|---|---|---|---|
| CL00023198 | 1.0 | 1.0 | 1.0 |  | G1P |
| CL00025408 | 1.0 | 2.2 | 0.3 | D66E/Q114H/ |  |
| CL00025417 | 1.0 | 1.9 | 3.0 | G35S/V41F/ |  |
| CL00025481 | 1.0 | 3.0 | 6.3 | G35S/ |  |
| CL00025500 | 1.0 | 3.0 | 6.3 | G35S/E195A/ |  |
| CL00025535 | 1.0 | 2.0 | 4.4 | G189R/E195A/ |  |
| CL00025550 | 1.0 | 2.7 | 5.3 | L17V/G35S/ |  |
| CL00025567 | 1.1 | 3.0 | 8.6 | L17V/G35S/I77V/L136V/G189R/ |  |
| CL00025583 | 1.0 | 2.6 | 5.0 | L17V/G35S/D66E/ |  |
| CL00025594 | 1.0 | 1.4 | 1.5 | L17V/D66E/L136V/ |  |
| CL00025622 | 1.0 | 1.4 | 0.8 | A132E/ |  |
| CL00025630 | 1.0 | 1.7 | 3.7 | G189R/ |  |
| CL00025634 | 1.0 | 1.0 | 0.8 | L17V/D66E/ |  |
| CL00025635 | 1.0 | 3.1 | 1.8 | G35S/Q114H/ |  |
| CL00025659 | 1.0 | 2.6 | 1.2 | Q114H/G189R/ |  |
| CL00025666 | 1.0 | 1.8 | 1.3 | D66E/V83I/ |  |
| CL00025686 | 1.0 | 1.6 | 3.2 | D66E/E80G/V83I/L136V/ | G2P |
| CL00025687 | 1.0 | 2.5 | 3.0 | G35S/D66E/V83I/A222T/ |  |
| CL00025689 | 1.0 | 2.7 | 0.3 | D66E/I77V/E80G/V83I/Q114H/A132E/G189R/ |  |
| CL00025717 | 1.0 | 1.1 | 1.7 | G120S/ |  |
| CL00025721 | 1.0 | 1.2 | 1.5 | A69I/ |  |
| CL00025728 | 1.0 | 1.4 | 1.4 | A69V/ |  |
| CL00025748 | 1.0 | 1.3 | 1.0 | D34E/ |  |
| CL00025754 | 1.0 | 1.0 | 0.7 | N74H/ |  |
| CL00025762 | 1.0 | 1.0 | 1.4 | G120T/ |  |
| CL00025791 | 1.0 | 1.1 | 3.1 | G120H/ |  |
| CL00025924 | 1.0 | 1.4 | 1.3 | A69C/ |  |
| CL00025935 | 1.0 | 1.2 | 1.3 | D34A/ |  |
| CL00025955 | 1.0 | 1.3 | 0.3 | G127A/ |  |
| CL00025958 | 1.0 | 1.2 | 1.2 | A69K/ |  |
| CL00025961 | 1.0 | 1.2 | 1.2 | A69Q/ |  |
| CL00025963 | 0.9 | 0.8 | 2.8 | G120R/ |  |
| CL00025984 | 1.0 | 1.5 | 2.2 | D34G/ |  |
| CL00026017 | 1.0 | 1.5 | 1.1 | E218T/ |  |

Figure 4B

| Colony Tracking Number | Activity Improvement<br><br>PF* AVG at pH7.2, 30°C, 30mins | Thermostability Improvement<br><br>PF* AVG at pH7.2, 30°C, 30mins after preincubation at pH7.2, 55.5°C for 10mins | pH Stability Improvement<br><br>PF* AVG at pH4.8, 30°C, 30mins | AA Mutations w.r.t. G1P (WT) | Alias |
|---|---|---|---|---|---|
| CL00026020 | 1.0 | 1.2 | 0.7 | A69T/ | |
| CL00026041 | 1.0 | 1.1 | 1.1 | D34Q/ | |
| CL00026052 | 1.0 | 2.0 | 0.6 | G120P/ | |
| CL00026054 | 1.0 | 1.6 | 1.1 | A184N/ | |
| CL00026061 | 1.0 | 1.0 | 1.8 | G120A/ | |
| CL00026088 | 1.0 | 1.4 | 0.3 | E218M/ | |
| CL00026089 | 1.0 | 1.8 | 0.2 | E218N/ | |
| CL00026102 | 1.0 | 2.1 | 3.9 | D34K/ | |
| CL00026104 | 1.0 | 1.1 | 1.1 | D34S/ | |
| CL00026114 | 1.0 | 1.4 | 0.1 | E218A/ | |
| CL00026241 | 1.0 | 1.4 | 0.7 | V76S | |
| CL00026289 | 1.0 | 1.4 | 5.4 | E244H | |
| CL00026296 | 1.0 | 1.5 | 2.1 | S162N | |
| CL00026297 | 1.0 | 1.1 | 1.1 | S162C | |
| CL00026308 | 1.0 | 0.6 | 2.8 | E244C | |
| CL00026310 | 1.0 | 1.2 | 2.3 | S188D | |
| CL00026313 | 1.0 | 1.1 | 2.8 | S188R | |
| CL00026320 | 1.0 | 1.5 | 1.3 | V76K | |
| CL00026328 | 1.0 | 1.5 | 2.1 | A50P | |
| CL00026344 | 1.0 | 1.4 | 2.8 | H139T | |
| CL00026349 | 1.0 | 1.4 | 0.7 | V76R | |
| CL00026369 | 1.0 | 1.4 | 1.8 | H139K | |
| CL00026396 | 1.0 | 1.8 | 5.2 | Q123K/R164K | |
| CL00026398 | 1.0 | 1.7 | 5.7 | E244K | |
| CL00026451 | 1.0 | 1.0 | 3.7 | S162H | |
| CL00026455 | 1.0 | 1.3 | 2.6 | E244S | |
| CL00026470 | 1.0 | 1.4 | 1.1 | Q70S | |
| CL00026476 | 1.0 | 0.7 | 2.4 | E244T | |
| CL00026535 | 1.0 | 1.2 | 5.9 | E244R | |
| CL00026540 | 1.0 | 0.9 | 1.1 | Q70N | |
| CL00026559 | 1.0 | 1.5 | 1.5 | Q70Y | |
| CL00026564 | 1.0 | 0.8 | 1.9 | V76E | |
| CL00026641 | 1.0 | 1.0 | 1.2 | V76L | |
| CL00026661 | 1.0 | 1.0 | 0.8 | V76A | |
| CL00026679 | 1.0 | 0.9 | 1.7 | E244G | |
| CL00026695 | 1.0 | 1.1 | 1.7 | S188N | |

Figure 4C

| Colony Tracking Number | Activity Improvement<br><br>PF* AVG at pH7.2, 30°C, 30mins | Thermostability Improvement<br><br>PF* AVG at pH7.2, 30°C, 30mins after preincubation at pH7.2, 55.5°C for 10mins | pH Stability Improvement<br><br>PF* AVG at pH4.8, 30°C, 30mins | AA Mutations w.r.t. G1P (WT) | Alias |
|---|---|---|---|---|---|
| CL00026696 | 1.0 | 1.4 | 0.1 | V76N | |
| CL00028441 | 1.0 | 2.2 | 6.9 | L81P | |
| CL00028451 | 1.0 | 2.0 | 6.2 | L81P/I84V | |
| CL00028468 | 1.0 | 1.2 | 1.0 | T62A/G79A/R164K/I193V | |
| CL00028526 | 1.0 | 2.2 | 7.1 | G79A/L81P | |
| CL00028549 | 1.0 | 1.5 | 1.8 | G79A/I84V/V122I | |
| CL00028564 | 1.0 | 2.2 | 5.8 | T62A/L81P/V122I/I193V | |
| CL00028574 | 1.0 | 2.2 | 7.0 | T62A/G79A/L81P | |
| CL00028598 | 1.0 | 1.0 | 1.2 | T62A/G79A | |
| CL00028616 | 1.0 | 2.3 | 7.5 | L81P/A185E | |
| CL00028623 | 1.0 | 2.2 | 6.1 | G79A/L81P/I84V/A155D | |
| CL00028629 | 1.0 | 1.7 | -0.1 | L68V/L81P/I84V/A155D/I193V | |
| CL00028657 | 1.0 | 2.0 | 6.2 | L81P/I84V/I193V | |
| CL00028669 | 1.0 | 1.6 | 0.5 | F32L/L81P/I84V/I193V | |
| CL00028670 | 1.0 | 2.0 | 2.0 | L68V/L81P/I84V/R164K | |
| CL00028687 | 1.0 | 1.8 | 1.7 | G79A | |
| CL00028741 | 1.0 | 2.0 | 2.8 | G79A/V122I/R164K | |
| CL00028745 | 1.0 | 1.5 | 1.3 | G79A/I84V | |
| CL00028752 | 1.0 | 1.4 | 0.2 | V122I/I193V/Q221H | |
| CL00028754 | 1.0 | 2.1 | 6.3 | L81P/V122I | |
| CL00028773 | 1.0 | 2.0 | 1.5 | T62A/G79A/L81P/I193V/Q221H | |
| CL00028835 | 1.0 | 1.0 | -0.1 | T62A/L68V/V122I/R164K | |
| CL00028844 | 1.0 | 2.1 | 5.1 | T62A/L81P/I84V | |
| CL00028864 | 1.0 | 1.4 | 0.9 | V122I | |
| CL00028867 | 1.0 | 2.0 | 2.5 | G79A/V122I | |
| CL00028868 | 1.0 | 1.9 | 1.1 | G79A/I193V | |

Figure 5     G2 Improvement

| Colony Tracking Number | Activity Improvement<br>PF* AVG at pH7.2, 30°C, 30mins | Thermostability Improvement<br>PF* AVG at pH7.2, 30°C, 30mins after preincubation at pH7.2, 55.5°C for 60mins | pH Stability Improvement<br>PF* AVG at pH4.8, 30°C, 30mins | Active mutations w.r.t. G2P | Alias |
|---|---|---|---|---|---|
| CL00025686 | 1.0 | 1.0 | 1.0 | | G2P |
| CL00028915 | 1.1 | 3.3 | 4.4 | D34K/A184N/G189R | |
| CL00028922 | 1.1 | 3.5 | 4.7 | D34K/A184N/G189R/E218T | |
| CL00028925 | 1.0 | 2.1 | 2.5 | D34K | |
| CL00028945 | 1.1 | 3.2 | 3.5 | D34K/A184N | |
| CL00028948 | 1.1 | 3.5 | 4.7 | D34K/I83V | |
| CL00028964 | 1.1 | 3.5 | 3.8 | D34K/A184N/E218T | |
| CL00028973 | 1.0 | 0.7 | 1.4 | I83V | |
| CL00028979 | 1.1 | 3.5 | 4.5 | D34K/I83V/A184N/G189R/E218T | |
| CL00029127 | 1.0 | 2.3 | 4.0 | D34K/I83V/G189R | |
| CL00029160 | 1.0 | 0.9 | 1.4 | R192M | |
| CL00029162 | 1.1 | 3.4 | 4.4 | D34K/I83V/G189R/E218T | |
| CL00029199 | 1.0 | 3.5 | 4.9 | D34K/I83V/A184N/G189R | G3P |
| CL00029214 | 1.0 | 2.9 | 4.2 | A184N/G189R | |
| CL00029220 | 1.0 | 2.9 | 3.9 | D34K/I83V/E218T | |

Figure 6 Validating Thermostability Profile of the Best Variants from Two Rounds of Enzyme Improvement
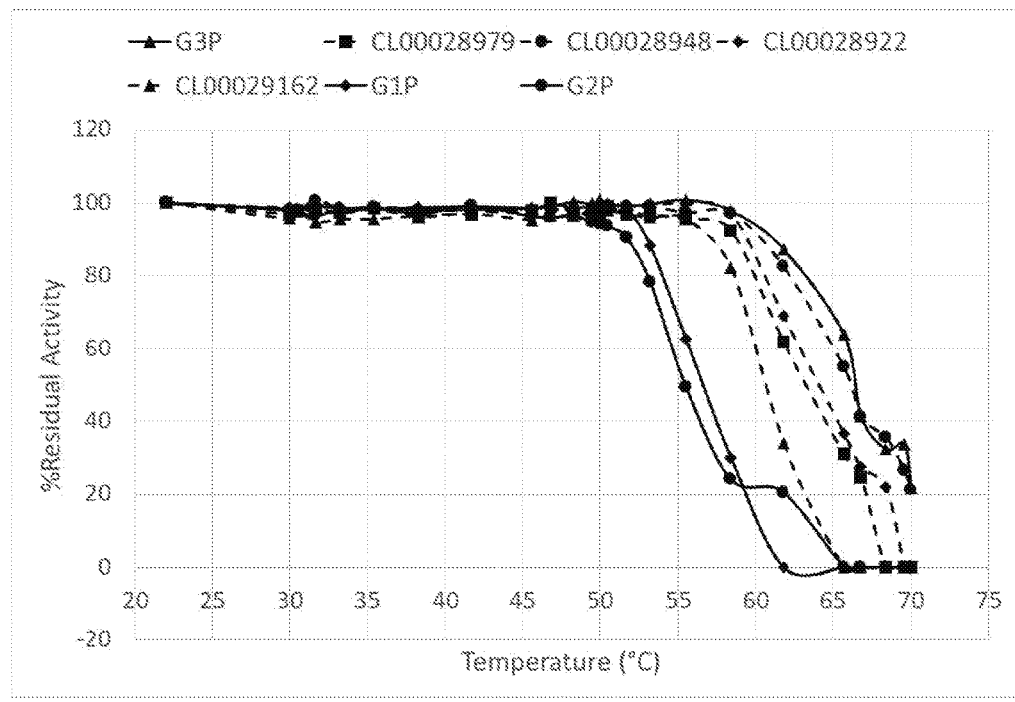

Figure 7 Sequence Alignment of G1P, G2P and G3P (Mutations Are Bolded and Underlined)

G1P: CL00023198 (SEQ ID NO:1)
G2P: CL00025686 (SEQ ID NO:33)
G3P: CL00029199 (SEQ ID NO:215)

```
            1                                              50
CL00023198  MILAHDVSGS GPLLVLLHGI TEDRRSWDPV DFTDGFTVVR VDLRGHGASA
CL00025686  MILAHDVSGS GPLLVLLHGI TEDRRSWDPV DFTDGFTVVR VDLRGHGASA
CL00029199  MILAHDVSGS GPLLVLLHGI TEDRRSWDPV DFTKGFTVVR VDLRGHGASA 51                                             100
CL00023198  AEEPYDIPTL ATDVHDTLAQ LAENDVIPGE LPVIVGHSMG GIVATAYGAL
CL00025686  AEEPYDIPTL ATDVHETLAQ LAENDVIPGG LPIIVGHSMG GIVATAYGAL
CL00029199  AEEPYDIPTL ATDVHETLAQ LAENDVIPGG LPVIVGHSMG GIVATAYGAL 101                                             150
CL00023198  FPARAIVNVD QPLQLAGMQG QVQQAEGMLR GADFPLFIHG MFAQMAGGLD
CL00025686  FPARAIVNVD QPLQLAGMQG QVQQAEGMLR GADFPVFIHG MFAQMAGGLD
CL00029199  FPARAIVNVD QPLQLAGMQG QVQQAEGMLR GADFPVFIHG MFAQMAGGLD 151                                             200
CL00023198  AEELARVNGI RSPRQDVVLG MWRPLLEDSP EELAALVSGL TRIPEDVPYL
CL00025686  AEELARVNGI RSPRQDVVLG MWRPLLEDSP EELAALVSGL TRIPEDVPYL
CL00029199  AEELARVNGI RSPRQDVVLG MWRPLLEDSP EELNALVSRL TRIPEDVPYL 201                                             250
CL00023198  VITGLDAGPE YAAWLQREIP QAVQEVWQPP THYPHLVDPA RFVERVEAFV
CL00025686  VITGLDAGPE YAAWLQREIP QAVQEVWQPP THYPHLVDPA RFVERVEAFV
CL00029199  VITGLDAGPE YAAWLQREIP QAVQEVWQPP THYPHLVDPA RFVERVEAFV

251
CL00023198  R
CL00025686  R
CL00029199  R
```

Figure 8    Beneficial Mutations at Each Position

| Position | Wild type residue | Particular variants | Position | Wild type residue | Particular variants |
|---|---|---|---|---|---|
| 17 | L | V | 122 | V | I |
| 32 | F | L | 123 | Q | K |
| 34 | D | A, E, G, K, Q, S | 127 | G | A |
| 35 | G | S | 132 | A | E |
| 41 | V | F | 136 | L | V |
| 50 | A | P | 139 | H | K, T |
| 62 | T | A | 155 | A | D |
| 66 | D | E | 162 | S | C, H, N |
| 68 | L | V | 164 | R | K |
| 69 | A | C, I, K, Q, T, V | 184 | A | N |
| 70 | Q | N, S, Y | 185 | A | E |
| 74 | N | H | 188 | S | D, N, R |
| 76 | V | A, E, K, L, N, R, S | 189 | G | R |
| 77 | I | V | 192 | R | M |
| 79 | G | A | 193 | I | V |
| 80 | E | G | 195 | E | A |
| 81 | L | P | 218 | E | A, M, N, T |
| 83 | V | I | 221 | Q | H |
| 84 | I | V | 222 | A | T |
| 114 | Q | H | 244 | E | C, G, H, K, R, S, T |
| 120 | G | A, H, P, R, S, T | | | |

Figure 9

>CL00025686 G2P amino acid sequence SEQ ID NO:33
MILAHDVSGSGPLLVLLHGITEDRRSWDPVDFTDGFTVVRVDLRGHGASAAEEPYDI
PTLATDVHETLAQLAENDVIPGGLPIIVGHSMGGIVATAYGALFPARAIVNVDQPLQL
AGMQGQVQQAEGMLRGADFPVFIHGMFAQMAGGLDAEELARVNGIRSPRQDVVLG
MWRPLLEDSPEELAALVSGLTRIPEDVPYLVITGLDAGPEYAAWLQREIPQAVQEVW
QPPTHYPHLVDPARFVERVEAFVR
>

>CL00025686 G2P nucleic acid sequence SEQ ID NO:34
ATGATCCTCGCCCACGACGTGTCGGGCTCCGGCCCGCTGCTGGTCCTCCTGCACG
GCATCACCGAAGACCGCCGCAGCTGGGATCCGGTCGATTTCACCGACGGCTTCAC
GGTCGTGCGGGTCGACCTGCGCGGGCACGGGGCATCAGCCGCCGAAGAACCGTA
CGACATCCCCACGCTCGCGACCGACGTGCACGAGACCCTCGCGCAGCTCGCCGA
GAACGACGTGATCCCCGGGGGCCTGCCGATCATCGTCGGCCACTCGATGGGCGG
GATCGTCGCGACGGCGTACGGCGCGCTCTTCCCCGCGCGGGCGATCGTCAACGTG
GACCAGCCTCTCCAGCTCGCGGGCATGCAGGGCCAGGTGCAGCAGGCGGAGGGG
ATGCTCCGCGGGGCGGACTTCCCGGTCTTCATCCACGGCATGTTCGCGCAGATGG
CGGGCGGCCTGGATGCCGAGGAGCTGGCGCGGGTGAATGGCATCCGGTCTCCGA
GGCAGGACGTCGTCCTCGGGATGTGGCGGCCGCTTCTCGAGGACTCACCCGAAG
AACTGGCGGCGCTCGTGAGCGGTCTGACGAGGATCCCGGAGGACGTCCCGTACC
TCGTGATCACGGGTCTCGATGCCGGGCCAGAGTACGCGGCGTGGCTGCAGCGGG
AGATCCCGCAGGCCGTCCAGGAGGTCTGGCAGCCGCCGACCCACTACCCGCACC
TCGTCGACCCGGCACGGTTCGTCGAGCGCGTCGAGGCTTTCGTCCGC
>

Figure 10

>CL00029199 G3P amino acid sequence SEQ ID NO:215
MILAHDVSGSGPLLVLLHGITEDRRSWDPVDFTKGFTVVRVDLRGHGASAAEEPYDI
PTLATDVHETLAQLAENDVIPGGLPVIVGHSMGGIVATAYGALFPARAIVNVDQPLQ
LAGMQGQVQQAEGMLRGADFPVFIHGMFAQMAGGLDAEELARVNGIRSPRQDVVL
GMWRPLLEDSPEELNALVSRLTRIPEDVPYLVITGLDAGPEYAAWLQREIPQAVQEV
WQPPTHYPHLVDPARFVERVEAFVR >CL00029199 G3P nucleic acid sequence SEQ ID NO:216
ATGATCCTCGCCCACGACGTGTCGGGCTCCGGCCCGCTGCTGGTCCTCCTGCACG
GCATCACCGAAGACCGCCGCAGCTGGGATCCGGTCGATTTCACCAAGGGCTTCA
CGGTCGTGCGGGTCGACCTGCGCGGGCACGGGGCATCAGCCGCCGAAGAACCGT
ACGACATCCCCACGCTCGCGACCGACGTGCACGAGACCCTCGCGCAGCTCGCCG
AGAACGACGTGATCCCCGGGGGCCTGCCGGTCATCGTCGGCCACTCGATGGGCG
GGATCGTCGCGACGGCGTACGGCGCGCTCTTCCCCGCGCGGGCGATCGTCAACGT
GGACCAGCCTCTCCAGCTCGCGGGCATGCAGGGCCAGGTGCAGCAGGCGGAGGG
GATGCTCCGCGGGGCGGACTTCCCGGTCTTCATCCACGGCATGTTCGCGCAGATG
GCGGGCGGCCTGGATGCCGAGGAGCTGGCGCGGGTGAATGGCATCCGGTCTCCG
AGGCAGGACGTCGTCCTCGGGATGTGGCGGCCGCTTCTCGAGGACTCACCCGAA
GAACTGAACGCGCTCGTGAGCCGCCTGACGAGGATCCCGGAGGACGTCCCGTAC
CTCGTGATCACGGGTCTCGATGCCGGGCCAGAGTACGCGGCGTGGCTGCAGCGG
GAGATCCCGCAGGCCGTCCAGGAGGTCTGGCAGCCGCCGACCCACTACCCGCAC
CTCGTCGACCCGGCACGGTTCGTCGAGCGCGTCGAGGCTTTCGTCCGC
>

Figure 11

>CL00023198 G1P amino acid sequence  SEQ ID NO:1
MILAHDVSGSGPLLVLLHGITEDRRSWDPVDFTDGFTVVRVDLRGHGASAAEEPYDI
PTLATDVHDTLAQLAENDVIPGELPVIVGHSMGGIVATAYGALFPARAIVNVDQPLQ
LAGMQGQVQQAEGMLRGADFPLFIHGMFAQMAGGLDAEELARVNGIRSPRQDVVL
GMWRPLLEDSPEELAALVSGLTRIPEDVPYLVITGLDAGPEYAAWLQREIPQAVQEV
WQPPTHYPHLVDPARFVERVEAFVR >CL00023198 G1P nucleic acid sequence SEQ ID NO:2
ATGATCCTCGCCCACGACGTGTCGGGCTCCGGCCCGCTGCTGGTCCTCCTGCACG
GCATCACCGAAGACCGCCGCAGCTGGGATCCGGTCGATTTCACCGACGGCTTCAC
GGTCGTGCGGGTCGACCTGCGCGGGCACGGGGCATCAGCCGCCGAAGAACCGTA
CGACATCCCCACGCTCGCGACCGACGTGCACGACACCCTCGCGCAGCTCGCCGA
GAACGACGTGATCCCCGGGGAACTGCCGGTGATCGTCGGCCACTCGATGGGCGG
GATCGTCGCGACGGCGTACGGCGCGCTCTTCCCCGCGCGGGCGATCGTCAACGTG
GACCAGCCTCTCCAGCTCGCGGGCATGCAGGGCCAGGTGCAGCAGGCGGAGGGG
ATGCTCCGCGGGGCGGACTTCCCGCTGTTCATCCACGGCATGTTCGCGCAGATGG
CGGGCGGCCTGGATGCCGAGGAGCTGGCGCGGGTGAATGGCATCCGGTCTCCGA
GGCAGGACGTCGTCCTCGGGATGTGGCGGCCGCTTCTCGAGGACTCACCCGAAG
AACTGGCGGCGCTCGTGAGCGGTCTGACGAGGATCCCGGAGGACGTCCCGTACC
TCGTGATCACGGGTCTCGATGCCGGGCCAGAGTACGCGGCGTGGCTGCAGCGGG
AGATCCCGCAGGCCGTCCAGGAGGTCTGGCAGCCGCCGACCCACTACCCGCACC
TCGTCGACCCGGCACGGTTCGTCGAGCGCGTCGAGGCTTTCGTCCGC

LACTONASE ENZYMES AND METHODS OF USING SAME

SEQUENCE LISTING

The instant application contains a Sequence Listing which has been submitted electronically in ASCII format and is hereby incorporated by reference in its entirety. Said ASCII copy, created on Aug. 2, 2017, is named 114095-5005-US_ST25.txt and is 367 kilobytes in size.

I. BACKGROUND OF THE INVENTION

Cell-to-cell communication in bacteria controls a broad range of activities, generally modulated by gene expression, that result in phenotypic changes and adaptation to environmental conditions during growth. The term "quorum sensing", or "QS" was coined to describe the ability of a population of unicellular bacteria to act as a single multicellular organism in a cell-density-dependent way using small diffusible molecules (see Amara et al., Chem. Rev. 2011, 195-208). There are a number of different classes of "quorum sensing molecules", QSMs, including oligopeptides, derivatives of dihydroxypentanedione (DPD), N-acyl homoserine lactones (AHLs), and other small molecules.

The signal molecules are produced and secreted during bacterial growth; as the population expands, the concentration of the QSMs increase. Once at a threshold level (e.g. the "quorum level"), these induce phenotypic effects by regulating QS-dependent target gene expression. For example, altered gene expression leads to pigmentation, biofilm formation, and virulence gene expression causing release of proteases, lytic enzymes, and exotoxins.

Quorum quenching ("QQ") enzymes such as AHL degrading enzymes have been shown to attenuate bacterial infections in fish (see Cao et al., J. App. Environ. Microbio. 78(6):1899 (2012)). These enzymes also have been shown to be useful in control of biofilm fouling of membranes, see Oh et. al., Environ. Science & Tech. 2012, 46:4877-4884 and Lade et al., Int. J. Biol. Sci. 2014 10:550.

The present invention provides novel AHL degrading enzymes and methods for use.

II. BRIEF SUMMARY OF THE INVENTION

Accordingly, the present invention provides compositions comprising a variant lactonase enzyme comprising an amino acid substitution as compared to SEQ ID NO:1, wherein said amino acid substitution is at a position selected from 17, 32, 34, 35, 41, 50, 62, 66, 68, 69, 70, 74, 76, 77, 79, 80, 81, 83, 84, 114, 120, 122, 123, 127, 132, 136, 139, 155, 162, 164, 184, 185, 188, 189, 192, 193, 195, 218, 221, 222 and 244, wherein the variant lactonase enzyme retains lactonase activity and is at least 95% identical to SEQ ID NO:1.

In further aspects, the invention provides compositions of variant lactonase enzymes as compared to SEQ ID NO:1, wherein the amino acid substitution is selected from L17V, F32L, D34A, D34E, D34G, D34K, D34Q, D34S, G35S, V41F, A50P, T62A, D66E, L68V, A69C, A69I, A69K, A69Q, A69T, A69V, Q70N, Q70S, Q70Y, N74H, V76A, V76E, V76K, V76L, V76N, V76R, V76S, I77V, G79A, E80G, L81P, V83I, I84V, Q114H, G120A, G120H, G120P, G120R, G120S, G120T, V122I, Q123K, G127A, A132E, L136V, H139K, H139T, A155D, S162C, S162H, S162N, R164K, A184N, A185E, S188D, S188N, S188R, G189R, R192M, I193V, E195A, E218A, E218M, E218N, E218T, Q221H, A222T, E244C, E244G, E244H, E244K, E244R, E244S and E244T. In some cases, these variant lactonase enzymes retain lactonase activity. In some cases they are at least 95% identical to SEQ ID NO:1.

In an additional aspect, the variant enzyme comprises the amino acid substitutions D66E/E80G/V83I/L136V. In this aspect, the variant enzyme optionally further comprises an amino acid substitution selected from L17V, F32L, D34A, D34E, D34G, D34K, D34Q, D34S, G35S, V41F, A50P, T62A, L68V, A69C, A69I, A69K, A69Q, A69T, A69V, Q70N, Q70S, Q70Y, N74H, V76A, V76E, V76K, V76L, V76N, V76R, V76S, I77V, G79A, L81P, I84V, Q114H, G120A, G120H, G120P, G120R, G120S, G120T, V122I, Q123K, G127A, A132E, H139K, H139T, A155D, S162C, S162H, S162N, R164K, A184N, A185E, S188D, S188N, S188R, G189R, R192M, I193V, E195A, E218A, E218M, E218N, E218T, Q221H, A222T, E244C, E244G, E244H, E244K, E244R, E244S and E244T.

In a further aspect, the variant enzyme comprises the amino acid substitutions D34K/D66E/E80G/L136V/A184N/G189P. In this aspect, the variant enzyme optionally further comprises an amino acid substitution selected from L17V, F32L, G35S, V41F, A50P, T62A, L68V, A69C, A69I, A69K, A69Q, A69T, A69V, Q70N, Q70S, Q70Y, N74H, V76A, V76E, V76K, V76L, V76N, V76R, V76S, I77V, G79A, L81P, I84V, Q114H, G120A, G120H, G120P, G120R, G120S, G120T, V122I, Q123K, G127A, A132E, H139K, H139T, A155D, S162C, S162H, S162N, R164K, A185E, S188D, S188N, S188R, R192M, I193V, E195A, E218A, E218M, E218N, E218T, Q221H, A222T, E244C, E244G, E244H, E244K, E244R, E244S and E244T.

In an additional aspect, the variant enzyme has an amino acid substitution set selected from D66E/Q114H, G35S/V41F, G35S, G35S/E195A, G189R/E195A, L17V/G35S, L17V/G35S/I77V/L136V/G189R, L17V/G35S/D66E, L17V/D66E/L136V, A132E, G189R, L17V/D66E, G35S/Q114H, Q114H/G189R, D66E/V83I, D66E/E80G/V83I/L136V, G35S/D66E/V83I/A222T, D66E/I77V/E80G/V83I/Q114H/A132E/G189R, G120S, A69I, A69V, D34E, N74H, G120T, G120H, A69C, D34A, G127A, A69K, A69Q, G120R, D34G, E218T, A69T, D34Q, G120P, A184N, G120A, E218M, E218N, D34K, D34S, E218A, V76S, E244N, S162N, S162C, E244C, S188D, S188R, V76K, A50P, H139T, V76R, H139K, Q123K/R164K, E244K, S162H, E244S, Q70S, E244T, E244R, Q70N, Q70Y, V76E, V76L, V76A, E244G, S188N, V76N, L81P, L81P/I84V, T62A/G79A/R164K/I193V, G79A/L81P, G79A/I84V/V122I, T62A/L81P/V122I/I193V, T62A/G79A/L81P, T62A/G79A, L81P/A185E, G79A/L81P/I84V/A155D, L68V/L81P/I84V/A155D/I193V, L81P/I84V/I193V, F32L/L81P/I84V/I193V, L68V/L81P/I84V/R164K, G79A, G79A/V122I/R164K, G79A/I84V, V122I/I193V/Q221H, L81P/V122I, T62A/G79A/L81P/I193V/Q221H, T62A/L68V/V122I/R164K, T62A/L81P/I84V, V122I, G79A/V122I, G79A/I193V, D66E/E80G/V83I/L136V/D34K/A184N/G189R, D66E/E80G/V83I/L136V/D34K/A184N/G189R/E218T, D66E/E80G/V83I/L136V/D34K, D66E/E80G/V83I/L136V/D34K/A184N, D66E/E80G/L136V/D34K, D66E/E80G/V83I/L136V/D34K/A184N/E218T, D66E/E80G/L136V, D66E/E80G/L136V/D34K/A184N/G189R/E218T, D66E/E80G/L136V/D34K/G189R, D66E/E80G/V83I/L136V/R192M, D66E/E80G/L136V/D34K/G189R/E218T, D66E/E80G/L136V/D34K/A184N/G189R, D66E/E80G/V83I/L136V/A184N/G189R and D66E/E80G/L136V/D34K/E218T.

In a further aspect, the composition as above further comprises animal feed.

In an additional aspect, the invention provides nucleic acids encoding the variant lactonase enzymes herein.

In a further aspect, the invention provides expression vectors comprising the nucleic acids, and host cells comprising the expression vectors.

In an additional aspect, the invention provides culturing a host cell comprising an expression vector as above under conditions wherein said enzyme is produced, and recovering the variant enzyme.

III. BRIEF DESCRIPTION OF THE DRAWINGS

FIG. 1 depicts the thermoactivity profile of the G1P wild type lactonase of SEQ ID NO:1 as determined in Example 5.

FIG. 2 depicts the pH profile of the G1P wild type lactonase of SEQ ID NO:1 as determined in Example 5.

FIG. 3 depicts the thermostability profile of the G1P wild type lactonase of SEQ ID NO:1 as determined in Example 5.

Figure 12:
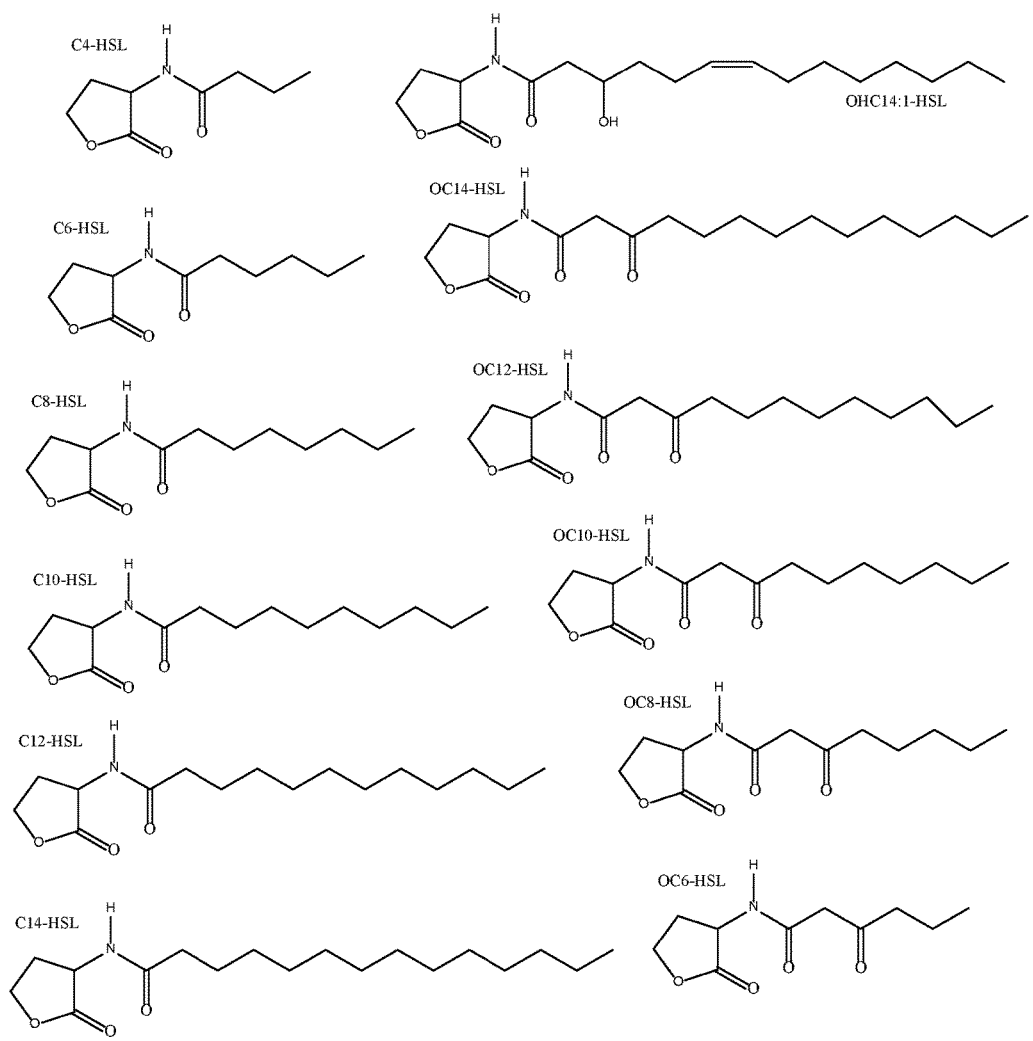

FIGS. 4A to 4C depict a table showing some of the first generation of variant lactonases, and their activity, pH and thermostability. CL00023198 is the G1P parent, whose amino acid sequence is SEQ ID NO:1 as shown in FIG. 7. The majority of the variants are single or double amino acid variants, as seen in the "AA Mutations" column, which shows the amino acid substitution (e.g. from D to E at position 66 and from Q to H at position 114 for CL00025408) as compared to G1P. The values of the table were determined as shown in Examples 6 to 8.

FIG. 5 depicts a table showing some of the second generation of variant lactonases, and their pH and thermostability. CL00025686 is the G2P parent, whose amino acid sequence is SEQ ID NO:33 as shown in FIG. 7. That is, all of the variants in FIG. 5 also contain the D66E/E80G/V83I/L136V G1P variants. The values of the table were determined as shown in Examples 5 to 9.

FIG. 6 depicts the thermostability profile of a number of variant lactonases including G2P and G3P, as determined in Example 9.

FIG. 7 shows the amino acid sequences and alignment of G1P, G2P and G3P.

FIG. 8 depicts a variant table showing some preferred variants in some embodiments of the invention. As described herein, these may be combined in any combination, and with variant sets as outlined herein.

FIG. 9 depicts the nucleic acid and amino acid sequences of the variant lactonase G2P.

FIG. 10 depicts the nucleic acid and amino acid sequences of the variant lactonase G3P.

FIG. 11 depicts the nucleic acid and amino acid sequences of the wild type lactonase enzyme, sometimes referred to herein as G1P.

FIG. 12 depicts some additional quorum sensing molecules and substrates.

IV. DETAILED DESCRIPTION OF THE INVENTION

A. Introduction

Bacteria communicate with each other by quorum sensing, using small diffusable molecules as signals, which trigger QS-dependent gene expression at threshold levels, which can lead to host organism bacterial infections, the formation of biofilms, etc. The concentration of these molecules is in the nanomolar to millimolar ranges, with diffusion ranges of from 4 to 80 mm, depending on the system.

Some of these events can be addresses by disruption of the quorum sensing system using quorum quenching enzymes, which break down these molecules. This type of interference with the quorum sensing system can replace traditional antibiotics and result in fewer side effects, as quorum quenching doesn't kill the bacteria or limit cell growth, but shuts down the expression of the pathogenic genes. This type of approach could be useful in agriculture to combat bacterial plant pathogens to be used as an alternative to pesticides, which carry obvious drawbacks. Similarly, this approach can be useful in aquaculture, where bacterial infections (particularly of *Aeromonas* spp. infections) in farmed fish could be treated without antibiotics that can be active in human consumers. In addition, most antibiotics that can kill *Aeromonas* spp. are banned from regular use in aquaculture, and in any event many *Aeromonas* spp. are resistant to commonly used antibiotics. *Aeromonas* infections in fish cause septicemia, resulting in fin and tail rot, as well as ulcerative syndrome in fish, resulting in losses over 100M USD due to *Aeromonas* infections. In addition, consuming fish infected with *Aeromonas* can cause intestinal or skin wound infections in humans.

As discussed herein, one of the major classes of QS molecules in gram-negative bacteria are the N-Acyl Homoserine Lactones (AHLs), which all comprise anhydro-cyclic esters, and generally contain different chain lengths and substituents. Lactonases are hydrolases that cleave the lactone ring of the AHL rendering them biologically inactive, as are prevented from binding to the target transcriptional regulators. A representative scheme is shown below:

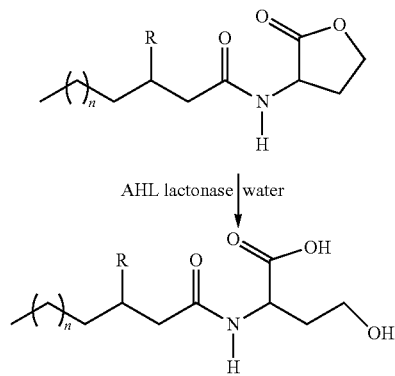

Generally, n is an integer of at least one and R is substituent. There are a number of possible AHL substrates, as different bacteria have different specificities. The general substrate used to test for lactonase activity is N-(3-Oxooctanoyl)-L-homoserine lactone, but a number of additional substrates can be used, including, but not limited to, those depicted in FIG. 12.

However, in general, native lactonases have limited pH ranges, limited thermoactivity ranges and limited thermostability ranges. As such, lactonase in feeds could be inactivated by temperature and/or the low pH in the gastrointestinal tract and thus can be difficult to exploit.

Accordingly, the present invention is directed to novel variant lactonase enzymes for use as antibacterial and antimicrobial agents for use in a variety of applications.

B. Definitions

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution D66E refers to a variant polypeptide, in this case a lactonase, in which the aspartic acid at position 66 is replaced with glutamic acid. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233– or E233#, E233( ) or E233del designates a deletion of glutamic acid at position 233. Additionally, EDA233– or EDA233# designates a deletion of the sequence GluAspAla that begins at position 233.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. In the present case, some embodiments utilize G1P, G2P or G3P as parent polypeptides, with the former being preferred.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about five amino acid modifications compared to the parent. As described below, in some embodiments the parent polypeptide is a wild type sequence, for example the wild type lactonase designated "G1P" herein, which is a lactonase from *Microbacterium testaceum*. As further discussed below, the protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it. Thus, by "variant lactonase" herein is meant a novel lactonase that has at least one amino acid modification in the amino acid sequence as compared to a parent lactonase enzyme. As discussed herein, in some cases the parent lactonase is a second or higher generation of variant; that is, as shown in FIG. 6, the G2P lactonase has 4 amino acid substitutions as compared to the wild type G1P parent. However, as shown in FIG. 7, the G3P has 4 amino acid substitutions as compared to the G2P parent, but a total of 8 amino acid substitutions as compared to the G1P. Unless otherwise noted or as will be obvious from the context, the variant lactonases of the invention generally are compared to the wild type G1P sequence. Additionally, unless otherwise noted, the variant lactonases of the invention are enzymatically active, that is, there is detectable lactonase activity using the lactonase assay described in Example 6, using an assay without temperature treatment.

As used herein, "protein" herein is meant at least two covalently attached amino acids, which includes proteins, polypeptides, oligopeptides and peptides. The peptidyl group generally comprise naturally occurring amino acids and peptide bonds. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Aspartic Acid 66 (also referred to as Asp66 or D66) is a residue at position 66 in the G1P parental enzyme.

By "non-naturally occurring modification" as used herein is meant an amino acid modification that is not found in the parent (e.g. G1P) enzyme.

By "amino acid" and "amino acid identity" as used herein is meant one of the 20 naturally occurring amino acids that are coded for by DNA and RNA.

By "position" as used herein is meant a location in the sequence of a protein. In general, the position number (which is more fully discussed below) is relative to the first amino acid of the mature lactonase sequence, e.g. excluding the signal peptide.

By "lactonase" herein is meant a protein with lactonase activity. By "lactonase activity" herein is meant that the enzyme catalyzes the hydrolysis of N-(3-Oxooctanoyl)-L-homoserine lactone which releases a proton, which is then detected using a pH sensitive colorimetric assay, the MOPS/BTB assay, wherein the release of protons upon hydrolysis of the substrate alters the pH of the weakly buffered assay and thus the protonation state of the pH sensitive dye BTB; see Yang et al., Anal. Biochem. 356(2006):297-299, hereby expressly incorporated by reference and specifically for the assay described therein. Enzymes having detectable activity in the assay outlined below and in Examples 6 are considered lactonases herein.

By "identity" in reference to two sequences herein is meant that the same amino acid is at the same position considering the alignment. The degree of identity between an amino acid sequence of the present invention ("invention sequence") and the parent amino acid sequence referred to in the claims (e.g. for G1P, SEQ ID NO:1) is calculated as the number of exact matches in an alignment of the two sequences, divided by the length of the "invention sequence," or the length of the SEQ ID NO:1, whichever is the shortest. The result is expressed in percent identity as calculated below.

For purposes of the present invention, the mature polypeptide disclosed in SEQ ID NO:1 is used to determine the corresponding amino acid residue in another lactonase of the present invention. The amino acid sequence of another lactonase is aligned with the mature polypeptide disclosed in SEQ ID NO:1, and based on the alignment, the amino acid position number corresponding to any amino acid residue in the mature polypeptide disclosed in SEQ ID NO:1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another lactonase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 51 1-518; Katoh and Toh, 2007, Bioinformatics 23: 372-374; Katoh et at, 2009, Methods in Molecular Biology 537: 39-64; Katoh and Toh, 2010, Bioinformatics 26: 1899-1900), EMBOSS EMMA employing ClustalW (1.83 or later; Thompson et al., 1994, Nucleic Acids Research 22: 4673-4680), and EMBL-EBI employing Clustal Omega (Sievers and Higgins, 2014, Methods Mol Biol. 2014; 1079:105-16), using their respective default parameters.

When the other enzyme has diverged from the polypeptide of SEQ ID NO:1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, Nucleic Acids Res. 25: 3389-3402). Even greater sensitivity can be achieved if the family or superfamily for the polypeptide has one or more representatives in the protein structure databases. Programs such as GenTHREADER (Jones, 1999, J. Mol. Biol. 287: 797-815; McGuffin and Jones, 2003, Bioinformatics 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, J. Mol. Biol. 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, Proteins 33: 88-96) or combinatorial extension (Shindyalov and Bourne, 1998, Protein Engineering 11: 739-747), and implementation of these algorithms can additionally be utilized to query structure databases with a structure of interest in order to discover possible structural homologs (e.g., Holm and Park, 2000, Bioinformatics 16: 566-567).

In describing the variants of the present invention, the nomenclature described below is adapted for ease of reference. The standardly accepted IUPAC single letter or three letter amino acid abbreviation is employed.

For an amino acid substitution, the following nomenclature is used herein: Original amino acid, position, substituted amino acid. Accordingly, the substitution of valine at position 83 with isoleucine is designated as "Val83Ile" or "V83I". Multiple mutations are separated by forward slash marks ("/"), e.g., "D66E/E80G/V83I/L136V", representing substitutions at positions 66, 80, 83 and 136, respectively. Note however that the order of recitation of the variants is irrelevant; "D66E/E80G/V83I/L136V" is the same variant as "L136V/E80G/D66E/V83I".

The term "isolated" as used herein refers to a polypeptide which is at least 20% pure, preferably at least 40% pure, more preferably at least 60% pure, even more preferably at least 80% pure, most preferably at least 90% pure, and even most preferably at least 95 to 98% pure, as determined by SDS-PAGE. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

By "recombinant enzyme" herein is meant that the enzyme is produced by recombinant techniques and that nucleic acid encoding the variant enzyme of the invention is operably linked to at least one exogeneous (e.g. not native to the parent lactonase) sequence, including, for examples, promoters, terminators, signal sequences, etc., as are more fully outlined below.

The term "nucleic acid construct" refers to a nucleic acid molecule, either single-stranded or double-stranded, which is isolated from a naturally occurring gene or is modified to contain segments of nucleic acids in a manner that would not otherwise exist in nature or which is synthetic, and which comprises one or more control sequences.

The term "operably linked" refers to a configuration in which a control sequence is placed at an appropriate position relative to the coding sequence of a polynucleotide such that the control sequence directs expression of the coding sequence.

V. LACTONASES OF THE INVENTION

Accordingly, the present invention provides variant lactonases with improved activity that can be used in a variety of applications, including animal and human nutritional and feed products, and for use as a pesticide in crop plants, with the use in feed stocks for fish of particular interest in some embodiments.

In general, the variant lactonases of the invention have modified, improved biochemical properties as compared to the wild type parental lactonase, "Lactonase G1P" or "G1P" (e.g. "generation 1 parent"), SEQ ID NO:1 herein, as shown in FIG. 7. The biochemical properties of the variant lactonases that can be improved herein include, but are not limited to, pH activity, pH stability, thermostability, specific activity, formulation stability (including liquid, solid and pellets), performance in fish and animals, and/or fish feed.

The variant lactonases of the invention have one or more improved properties as compared to G1P. By "improved" herein is meant a desirable change of at least one biochemical property. "Improved function" can be measured as a percentage increase or decrease of a particular activity, or as a "fold" change, with increases of desirable properties (e.g. pH stability, thermostability) or decreases of undesirable properties (e.g. protease sensitivity). That is, a variant lactonase may have a 10% increase in thermostability as compared to G1P. Alternatively, a variant lactonase may have a 2-fold increase in pH stability. In general, percentage changes are used to describe changes in biochemical activity of less than 100%, and fold-changes are used to describe changes in biochemical activity of greater than 100% (as compared to the parental enzyme, in many cases G1P). In the present invention, percentage changes (usually increases) of biochemical activity of at least about 10%, 20%, 30%, 40%, 50%, 60%, 70%, 80%, 90%, 95%, 98% and 99% can be accomplished. In the present invention, a "fold increase" (or decrease) is measured as compared to the starting or parent enzyme. For example, as shown in the Figures, G2P has a 2.5 fold increase in temperature tolerance as compared to G1P: this is calculated by [(activity of variant)/(activity of parent)]. In many embodiments, the improvement is at least one and a half fold (1.5 fold), 2 fold, 3 fold, 4 fold, 5 fold, 6 fold, 7 fold, 8 fold, 9 fold, or 10 fold or higher.

In general, improvements are measured as compared to the G1P enzyme (the wild type) using a lactonase activity assay, under conditions that challenge the variant lactonase against the G1P enzyme.

A. Lactonase Activity

The variant lactonases can be tested in a variety of ways, however, all variant lactonases will retain lactonase activity at some level, as discussed herein. The basic lactonase assay is run as shown in Example 5 and as follows: after challenge under the appropriate conditions of temperature, pH, etc. (discussed below), the sample is brought to a final concentration of 0.05M Tris-HCl, pH 7.2. The substrate, N-(3-Oxooctanoyl)-L-homoserine lactone substrate ($C_{12}H_{19}NO_4$, FW: 241.3), prepared in 4% DMSO to a final concentration of 8 mM substrate in the reaction, pH 7.2. The reaction is incubated at 30° C. (for baseline activity, other temperatures such as 50° C. and 60° C. to assay general thermoactivity), 200 rpm for 30 minutes. The reaction is then quenched with 75 µl of quenching reagent containing 3.5 M NaOH:2 M hydroxylamine hydrochloride:: 1:1. Following quenching 75 µl of coloring reagent was added. The coloring reagent is freshly prepared by mixing adding equal volumes of 10% FeCl3 in 4 M HCl to 95% EtOH. After shaking the plates for 1-2 minutes, they are subjected to centrifugation at 4000 rpm for 2 minutes. The plate absorbance is then read at 530 nm, as an indication of the release of protons as a result of the reaction; see Yang et. al., supra, incorporated by reference herein for the assay and assay conditions.

The enzyme may be a purified sample, a fermentation sample, or a raw sample.

The variant lactonases of the invention can have an improvement one or more of a number of biochemical properties, including, but not limited to, pH activity, pH stability, thermostability, specific activity, formulation stability (including liquid, solid and pellets), performance in animals and/or animal feed.

B. Thermostability

In many embodiments, the variant lactonases of the invention have increased thermostability, particularly under the conditions used to produce animal feeds, for example, which frequently use high temperatures during the pelleting process for periods of time that should inactivate wild type lactonases. "Thermostability" in this context means that the variant enzymes are more stable than the parent lactonase (e.g. G1P) under the same thermal challenge conditions, that is, the activity of the variant is higher than that of the G1P under identical conditions (generally using the lactonase assay as outlined herein and as shown in Example 7).

In one embodiment, the variant lactonases are more stable than the parent lactonase when exposed to temperatures of 50° C., 55° C., 55.5° C., 58° C. and/or 60° C. for a period of time, generally ranging from about 1, 2, 3, 4, 5, 6, 7, 8, 9 or 10 minutes or longer, depending on the ultimate conditions for the use of the variant lactonase, with some embodiments utilizing thermal challenge times of 5 minutes to 10 minutes, 5 minutes to 15 minutes, 5 minutes to 60 minutes, 10 minutes to 60 minutes all finding use in the present invention. In some embodiments, a challenge of 55.5° C. and 10 minutes is used, and in some embodiments a challenge of 55.5° C. and 60 minutes is used.

Accordingly, in some embodiments the variant lactonases have increased thermostability as compared to a parent lactonase, particularly G1P, for at least 5 minutes at 50° C., at least 5-10 minutes at 55° C., at least 5-10 minutes at 55.5° C. and in some embodiments at least 60 minutes at 55.5° C.

In addition, pH can be a consideration for thermostability as well. Accordingly, in some embodiments the variant lactonases have increased thermostability as compared to a parent lactonase for at least 5-10 to 60 minutes at 55.5° C. at pH 7.2.

Accordingly, as shown in FIGS. 4, 5 and 6, a number of variant lactonases of the invention exhibit increased thermostability.

C. pH Stability

In many embodiments, the variant lactonases of the invention have increased pH stability at lower pHs. "Increased pH stability" in this context means that the variant enzymes are more stable than the parent lactonase (e.g. G1P) under the same pH challenge conditions, that is, the activity of the variant is higher than that of the G1P under identical conditions (generally using the lactonase assay as outlined herein and as shown in Example 5).

VI. SPECIFIC VARIANT LACTONASES

Accordingly, the present invention provides a number of specific variant lactonases with improved activity, specifically thermal stability and/or pH stability, and in particular thermal stability at particular pHs as outlined herein.

In some embodiments, the variant lactonase has one or more amino acid substitutions at a position (relative to G1P) selected from 17, 32, 34, 35, 41, 50, 62, 66, 68, 69, 70, 74, 76, 77, 79, 80, 81, 83, 84, 114, 120, 122, 123, 127, 132, 136, 139, 155, 162, 164, 184, 185, 188, 189, 192, 193, 195, 218, 221, 222 and 244. In some embodiments, the variant lactonase has from 1, 2, 3, 4, 5, 6, 7, 8, 9, 10, 11, 12, 13, 14, 15, 16, 17, 18, 19 or 20 amino acid substitutions selected from these positions, with from 1 to 10 finding use in some embodiments.

As will be appreciated by those in the art, the variant lactonase can have a number of amino acid substitutions as compared to G1P, although to be considered a variant lactonase it must still possess detectable activity in a lactonase assay as described herein, and it must be sufficiently identical to G1P to align in a sequence alignment program as discussed herein.

In some embodiments, the variant lactonase has one or more amino acid substitutions selected from L17V, F32L, D34A, D34E, D34G, D34K, D34Q, D34S, G35S, V41F, A50P, T62A, D66E, L68V, A69C, A69I, A69K, A69Q, A69T, A69V, Q70N, Q70S, Q70Y, N74H, V76A, V76E, V76K, V76L, V76N, V76R, V76S, I77V, G79A, E80G, L81P, V83I, I84V, Q114H, G120A, G120H, G120P, G120R, G120S, G120T, V122I, Q123K, G127A, A132E, L136V, H139K, H139T, A155D, S162C, S162H, S162N, R164K, A184N, A185E, S188D, S188N, S188R, G189R, R192M, I193V, E195A, E218A, E218M, E218N, E218T, Q221H, A222T, E244C, E244G, E244H, E244K, E244R, E244S and E244T. In some embodiments, the variant lactonase has from 1, 2, 3, 4, 5, 6, 7, 8, 9, 10, 11, 12, 13, 14, 15, 16, 17, 18, 19 or 20 amino acid substitutions selected from these positions, with from 1 to 10 finding use in some embodiments.

In some embodiments, the variant lactonase has an amino acid substitution of the leucine at position 17 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is L17V.

In some embodiments, the variant lactonase has an amino acid substitution of the phenylalanine at position 32 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, alanine, isoleucine, methionine, tryptophan valine and tyrosine, with some embodiments not utilizing cysteine (due to possible disulfide formation) or proline (due to steric effects). In some embodiments, the amino acid substitution is F32L.

In some embodiments, the variant lactonase has an amino acid substitution of the aspartic acid at position 34 of SEQ ID NO:1. In some embodiments, the substitution is with any of the other 19 naturally occurring amino acids, namely glutamine, serine, leucine, threonine, asparagine, lysine, arginine, histidine, glutamic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is selected from D34A, D34E, D34G, D34K, D34Q and D34S.

In some embodiments, the variant lactonase has an amino acid substitution of the glycine at position 35 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is G35S.

In some embodiments, the variant lactonase has an amino acid substitution of the valine at position 41 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, alanine, isoleucine, methionine, phenylalanine, tryptophan and tyrosine, with some embodiments not utilizing cysteine (due to possible disulfide formation) or proline (due to steric effects). In some embodiments, the amino acid substitution is V41F.

In some embodiments, the variant lactonase has an amino acid substitution of the alanine at position 50 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, isoleucine, methionine, phenylalanine, tryptophan valine and tyrosine, with some embodiments not utilizing cysteine (due to possible disulfide formation) or proline (due to steric effects). In some embodiments, the amino acid substitution is A50P.

In some embodiments, the variant lactonase has an amino acid substitution of the threonine at position 62 of SEQ ID NO:1. In some embodiments, the substitution is with any of the other 19 naturally occurring amino acids, namely glutamine, serine, leucine, asparagine, lysine, arginine, histidine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is T62A.

In some embodiments, the variant lactonase has an amino acid substitution of the aspartic acid at position 66 of SEQ ID NO:1. In some embodiments, the substitution is with any of the other 19 naturally occurring amino acids, namely glutamine, serine, leucine, threonine, asparagine, lysine, arginine, histidine, glutamic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is D66E.

In some embodiments, the variant lactonase has an amino acid substitution of the leucine at position 68 of SEQ ID NO:1. In some embodiments, the substitution is with any of the other 19 naturally occurring amino acids, namely glutamine, serine, threonine, asparagine, lysine, arginine, histidine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is L68V.

In some embodiments, the variant lactonase has an amino acid substitution of the alanine at position 69 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, isoleucine, methionine, phenylalanine, tryptophan, valine and tyrosine, with some embodiments not utilizing cysteine (due to possible disulfide formation) or proline (due to steric effects). In some embodiments, the amino acid substitution is selected from A69C, A69I, A69K, A69Q, A69T and A69V.

In some embodiments, the variant lactonase has an amino acid substitution of the glutamine at position 70 of SEQ ID NO:1. In some embodiments, the substitution is with any of the other 19 naturally occurring amino acids, namely serine, leucine, threonine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is selected from Q70N, Q70S and Q70Y.

In some embodiments, the variant lactonase has an amino acid substitution of the asparagine at position 74 of SEQ ID NO:1. In some embodiments, the substitution is with any of the other 19 naturally occurring amino acids, namely glutamine, serine, leucine, threonine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is N74H.

In some embodiments, the variant lactonase has an amino acid substitution of the valine at position 76 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, alanine, isoleucine, methionine, phenylalanine, tryptophan and tyrosine, with some embodiments not utilizing cysteine (due to possible disulfide formation) or proline (due to steric effects). In some embodiments, the amino acid substitution is selected from V76A, V76E, V76K, V76L, V76N, V76R and V76S.

In some embodiments, the variant lactonase has an amino acid substitution of the isoleucine at position 77 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, alanine, methionine, phenylalanine, tryptophan valine and tyrosine, with some embodiments not utilizing cysteine (due to possible disulfide formation) or proline (due to steric effects). In some embodiments, the amino acid substitution is I77V.

In some embodiments, the variant lactonase has an amino acid substitution of the glycine at position 79 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is G79A.

In some embodiments, the variant lactonase has an amino acid substitution of the glutamic acid at position 80 of SEQ ID NO:1. In some embodiments, the substitution is with any of the other 19 naturally occurring amino acids, namely glutamine, serine, leucine, threonine, asparagine, lysine, arginine, histidine, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is E80G.

In some embodiments, the variant lactonase has an amino acid substitution of the leucine at position 81 of SEQ ID NO:1. In some embodiments, the substitution is with any of the other 19 naturally occurring amino acids, namely glutamine, serine, threonine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is L81P.

In some embodiments, the variant lactonase has an amino acid substitution of the valine at position 83 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, alanine, isoleucine, methionine, phenylalanine, tryptophan and tyrosine, with some embodiments not utilizing cysteine (due to possible disulfide formation) or proline (due to steric effects). In some embodiments, the amino acid substitution is V83I.

In some embodiments, the variant lactonase has an amino acid substitution of the isoleucine at position 84 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, alanine, methionine, phenylalanine, tryptophan, valine and tyrosine, with some embodiments not utilizing cysteine (due to possible disulfide formation) or proline (due to steric effects). In some embodiments, the amino acid substitution is I84V.

In some embodiments, the variant lactonase has an amino acid substitution of the glutamine at position 114 of SEQ ID NO:1. In some embodiments, the substitution is with any of the other 19 naturally occurring amino acids, namely serine, leucine, threonine, asparagine, lysine, arginine, histidine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is Q114H.

In some embodiments, the variant lactonase has an amino acid substitution of the glycine at position 120 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is selected from G120A, G120H, G120P, G120R, G120S and G120T.

In some embodiments, the variant lactonase has an amino acid substitution of the valine at position 122 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, alanine, isoleucine, methionine, phenylalanine, tryptophan and tyrosine, with some embodiments not utilizing cysteine (due to possible disulfide formation) or proline (due to steric effects). In some embodiments, the amino acid substitution is V122I.

In some embodiments, the variant lactonase has an amino acid substitution of the glutamine at position 17 of SEQ ID NO:1. In some embodiments, the substitution is with any of the other 19 naturally occurring amino acids, namely serine, leucine, threonine, asparagine, lysine, arginine, histidine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is Q123K.

In some embodiments, the variant lactonase has an amino acid substitution of the glycine at position 127 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is G127A.

In some embodiments, the variant lactonase has an amino acid substitution of the alanine at position 132 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, isoleucine, methionine, phenylalanine, tryptophan valine and tyrosine, with some embodiments not utilizing cysteine (due to possible disulfide formation) or proline (due to steric effects). In some embodiments, the amino acid substitution is A132E.

In some embodiments, the variant lactonase has an amino acid substitution of the leucine at position 136 of SEQ ID NO:1. In some embodiments, the substitution is with any of the other 19 naturally occurring amino acids, namely glutamine, serine, threonine, asparagine, lysine, arginine, histidine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is L136V.

In some embodiments, the variant lactonase has an amino acid substitution of the histidine at position 139 of SEQ ID NO:1. In some embodiments, the substitution is with any of the other 19 naturally occurring amino acids, namely glutamine, serine, leucine, threonine, asparagine, lysine, arginine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is selected from H139K and H139T.

In some embodiments, the variant lactonase has an amino acid substitution of the alanine at position 155 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, isoleucine, methionine, phenylalanine, tryptophan valine and tyrosine, with some embodiments not utilizing cysteine (due to possible disulfide formation) or proline (due to steric effects). In some embodiments, the amino acid substitution is A155D.

In some embodiments, the variant lactonase has an amino acid substitution of the serine at position 162 of SEQ ID NO:1. In some embodiments, the substitution is with any of the other 19 naturally occurring amino acids, namely glutamine, leucine, threonine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is selected from A162C, A162H and A162N.

In some embodiments, the variant lactonase has an amino acid substitution of the arginine at position 164 of SEQ ID NO:1. In some embodiments, the substitution is with any of the other 19 naturally occurring amino acids, namely glutamine, serine, leucine, threonine, asparagine, lysine, histidine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is R164K.

In some embodiments, the variant lactonase has an amino acid substitution of the alanine at position 184 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, isoleucine, methionine, phenylalanine, tryptophan, valine and tyrosine, with some embodiments not utilizing cysteine (due to possible disulfide formation) or proline (due to steric effects). In some embodiments, the amino acid substitution is A184N.

In some embodiments, the variant lactonase has an amino acid substitution of the alanine at position 185 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, isoleucine, methionine, phenylalanine, tryptophan valine and tyrosine, with some embodiments not utilizing cysteine (due to possible disulfide formation) or proline (due to steric effects). In some embodiments, the amino acid substitution is A185E.

In some embodiments, the variant lactonase has an amino acid substitution of the serine at position 188 of SEQ ID NO:1. In some embodiments, the substitution is with any of the other 19 naturally occurring amino acids, namely glutamine, leucine, threonine, asparagine, lysine, arginine, histidine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is selected from S188D, S188N and S188R.

In some embodiments, the variant lactonase has an amino acid substitution of the glycine at position 189 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is G189R.

In some embodiments, the variant lactonase has an amino acid substitution of the arginine at position 192 of SEQ ID NO:1. In some embodiments, the substitution is with any of the other 19 naturally occurring amino acids, namely glutamine, serine, leucine, threonine, asparagine, lysine, histidine, glutamic acid, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is R192M.

In some embodiments, the variant lactonase has an amino acid substitution of the isoleucine at position 193 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, alanine, methionine, phenylalanine, tryptophan valine and tyrosine, with some embodiments not utilizing cysteine (due to possible disulfide formation) or proline (due to steric effects). In some embodiments, the amino acid substitution is I193V.

In some embodiments, the variant lactonase has an amino acid substitution of the glutamic acid at position 195 of SEQ ID NO:1. In some embodiments, the substitution is with any of the other 19 naturally occurring amino acids, namely glutamine, serine, leucine, threonine, asparagine, lysine, arginine, histidine, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is E195A.

In some embodiments, the variant lactonase has an amino acid substitution of the glutamic acid at position 218 of SEQ ID NO:1. In some embodiments, the substitution is with any of the other 19 naturally occurring amino acids, namely glutamine, serine, leucine, threonine, asparagine, lysine, arginine, histidine, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is selected from E218A, E218M, E218N and E218T.

In some embodiments, the variant lactonase has an amino acid substitution of the glutamine at position 221 of SEQ ID NO:1. In some embodiments, the substitution is with any of the other 19 naturally occurring amino acids, namely serine, leucine, threonine, asparagine, lysine, arginine, histidine, glutamic acid, aspartic acid, cysteine, glycine, proline, alanine, isoleucine, methionine, phenylalanine, tryptophan, valine and tyrosine, with some embodiments not utilizing cysteine (due to possible disulfide formation) or proline (due to steric effects). In some embodiments, the amino acid substitution is Q221H.

In some embodiments, the variant lactonase has an amino acid substitution of the alanine at position 222 of SEQ ID NO:1. In some embodiments, the substitution is with any of the other 19 naturally occurring amino acids, namely glutamine, serine, leucine, threonine, asparagine, lysine, arginine, histidine, glutamic acid, aspartic acid, cysteine, glycine, proline, isoleucine, methionine, phenylalanine, tryptophan, valine and tyrosine, with some embodiments not utilizing cysteine (due to possible disulfide formation) or proline (due to steric effects). In some embodiments, the amino acid substitution is A222T.

In some embodiments, the variant lactonase has an amino acid substitution of the glutamic acid at position 244 of SEQ ID NO:1. In some embodiments, the substitution is with any of the other 19 naturally occurring amino acids, namely glutamine, serine, leucine, threonine, asparagine, lysine, arginine, histidine, aspartic acid, cysteine, glycine, proline, alanine, isoleucine, methionine, phenylalanine, tryptophan valine and tyrosine, with some embodiments not utilizing cysteine (due to possible disulfide formation) or proline (due to steric effects). In some embodiments, the amino acid substitution is selected from E244C, E244G, E244H, E244K, E244R, E244S and E244T.

In some embodiments the variant lactonase comprises the G2P variants D66E/E80G/V83I/L136V and at least one of the additional single amino acid variants outline above, including, but not limited to, L17V, F32L, D34A, D34E, D34G, D34K, D34Q, D34S, G35S, V41F, A50P, T62A, L68V, A69C, A69I, A69K, A69Q, A69T, A69V, Q70N, Q70S, Q70Y, N74H, V76A, V76E, V76K, V76L, V76N, V76R, V76S, I77V, G79A, L81P, I84V, Q114H, G120A, G120H, G120P, G120R, G120S, G120T, V122I, Q123K, G127A, A132E, H139K, H139T, A155D, S162C, S162H, S162N, R164K, A184N, A185E, S188D, S188N, S188R, G189R, R192M, I193V, E195A, E218A, E218M, E218N, E218T, Q221H, A222T, E244C, E244G, E244H, E244K, E244R, E244S and E244T. In this embodiment, the variant lactonase can have from 1, 2, 3, 4, 5 or 6 additional amino acid variants.

In some embodiments the variant lactonase comprises the G3P variants D34K/I83V/A184N/G189R and at least one of the additional single amino acid variants outline above, including, but not limited to L17V, F32L, G35S, V41F, A50P, T62A, D66E, L68V, A69C, A69I, A69K, A69Q, A69T, A69V, Q70N, Q70S, Q70Y, N74H, V76A, V76E, V76K, V76L, V76N, V76R, V76S, I77V, G79A, E80G, L81P, I84V, Q114H, G120A, G120H, G120P, G120R, G120S, G120T, V122I, Q123K, G127A, A132E, L136V, H139K, H139T, A155D, S162C, S162H, S162N, R164K, A185E, S188D, S188N, S188R, R192M, I193V, E195A, E218A, E218M, E218N, E218T, Q221H, A222T, E244C, E244G, E244H, E244K, E244R, E244S and E244T. In this embodiment, the variant lactonase can have from 1, 2, 3, 4, 5 or 6 additional amino acid variants.

In some embodiments the variant lactonase comprises the G2P and G3P variants D34K/D66E/E80G/I83V/L136V/A184N/G189R and at least one of the additional single amino acid variants outline above, including, but not limited to L17V, F32L, G35S, V41F, A50P, T62A, L68V, A69C, A69I, A69K, A69Q, A69T, A69V, Q70N, Q70S, Q70Y, N74H, V76A, V76E, V76K, V76L, V76N, V76R, V76S, I77V, G79A, L81P, I84V, Q114H, G120A, G120H, G120P, G120R, G120S, G120T, V122I, Q123K, G127A, A132E, H139K, H139T, A155D, S162C, S162H, S162N, R164K, A185E, S188D, S188N, S188R, R192M, I193V, E195A, E218A, E218M, E218N, E218T, Q221H, A222T, E244C, E244G, E244H, E244K, E244R, E244S and E244T. In this embodiment, the variant lactonase can have from 1, 2, 3, 4, 5 or 6 additional amino acid variants.

In some embodiments the variant lactonase comprises the G2P and G3P variants D34K/D66E/E80G/V83I/L136V/A184N/G189R and at least one of the additional single amino acid variants outline above, including, but not limited to L17V, F32L, G35S, V41F, A50P, T62A, L68V, A69C, A69I, A69K, A69Q, A69T, A69V, Q70N, Q70S, Q70Y, N74H, V76A, V76E, V76K, V76L, V76N, V76R, V76S, I77V, G79A, L81P, I84V, Q114H, G120A, G120H, G120P, G120R, G120S, G120T, V122I, Q123K, G127A, A132E, H139K, H139T, A155D, S162C, S162H, S162N, R164K, A185E, S188D, S188N, S188R, R192M, I193V, E195A, E218A, E218M, E218N, E218T, Q221H, A222T, E244C, E244G, E244H, E244K, E244R, E244S and E244T. In this embodiment, the variant lactonase can have from 1, 2, 3, 4, 5 or 6 additional amino acid variants.

In some embodiments the variant lactonase comprises the G2P and G3P variants D34K/D66E/E80G/V83I/L136V/ A184N/G189R and can have additional amino acid substitutions at other positions. In this embodiment, the variant lactonase can have from 1, 2, 3, 4, 5 or 6 additional amino acid variants; again, in this embodiment, the variant lactonase retains detectable activity in the lactonase assay as outlined herein.

In some embodiments the variant lactonase comprises the G2P and G3P variants D34K/D66E/E80G/I83V/L136V/ A184N/G189R and can have additional amino acid substitutions at other positions. In this embodiment, the variant lactonase can have from 1, 2, 3, 4, 5 or 6 additional amino acid variants; again, in this embodiment, the variant lactonase retains detectable activity in the lactonase assay as outlined herein.

Some particular embodiments of the present invention are lactonase variants as compared to SEQ ID NO:1 having an amino acid substitution set selected from D66E/Q114H, G35S/V41F, G35S, G35S/E195A, G189R/E195A, L17V/ G35S, L17V/G35S/I77V/L136V/G189R, L17V/G35S/ D66E, L17V/D66E/L136V, A132E, G189R, L17V/D66E, G35S/Q114H, Q114H/G189R, D66E/V83I, D66E/E80G/ V83I/L136V, G35S/D66E/V83I/A222T, D66E/I77V/E80G/ V83I/Q114H/A132E/G189R, G120S, A69I, A69V, D34E, N74H, G120T, G120H, A69C, D34A, G127A, A69K, A69Q, G120R, D34G, E218T, A69T, D34Q, G120P, A184N, G120A, E218M, E218N, D34K, D34S, E218A, V76S, E244H, S162N, S162C, E244C, S188D, S188R, V76K, A50P, H139T, V76R, H139K, Q123K/R164K, E244K, S162H, E244S, Q70S, E244T, E244R, Q70N, Q70Y, V76E, V76L, V76A, E244G, S188N, V76N, L81P, L81P/I84V, T62A/G79A/R164K/I193V, G79A/L81P, G79A/I84V/V122I, T62A/L81P/V122I/I193V, T62A/ G79A/L81P, T62A/G79A, L81P/A185E, G79A/L81P/I84V/ A155D, L68V/L81P/I84V/A155D/I193V, L81P/I84V/ I193V, F32L/L81P/I84V/I193V, L68V/L81P/I84V/R164K, G79A, G79A/V122I/R164K, G79A/I84V, V122I/I193V/ Q221H, L81P/V122I, T62A/G79A/L81P/I193V/Q221H, T62A/L68V/V122I/R164K, T62A/L81P/I84V, V122I, G79A/V122I, G79A/I193V, D66E/E80G/V83I/L136V/ D34K/A184N/G189R, D66E/E80G/V83I/L136V/D34K/ A184N/G189R/E218T, D66E/E80G/V83I/L136V/D34K, D66E/E80G/V83I/L136V/D34K/A184N, D66E/E80G/ L136V/D34K, D66E/E80G/V83I/L136V/D34K/A184N/ E218T, D66E/E80G/L136V, D66E/E80G/L136V/D34K/ A184N/G189R/E218T, D66E/E80G/L136V/D34K/G189R, D66E/E80G/V83I/L136V/R192M, D66E/E80G/L136V/ D34K/G189R/E218T, D66E/E80G/L136V/D34K/A184N/ G189R, D66E/E80G/V83I/L136V/A184N/G189R and D66E/E80G/L136V/D34K/E218T.

VII. NUCLEIC ACIDS OF THE INVENTION

The present invention additional provides nucleic acids encoding the variant lactonases of the invention. As will be appreciated by those in the art, due to the degeneracy of the genetic code, an extremely large number of nucleic acids may be made, all of which encode the variant lactonases of the present invention. Thus, having identified a particular amino acid sequence, those skilled in the art could make any number of different nucleic acids, by simply modifying the sequence of one or more codons in a way which does not change the amino acid sequence of the protein. Thus, providing the amino acid sequence allows the generation of a very large number of different nucleic acid sequences encoding the proteins.

In some embodiments, specific variant lactonases are encoded by specific nucleic acid sequences, as are listed in the sequence listing.

As is known in the art, the nucleic acids encoding variant lactonases of the invention can be incorporated into expression vectors as is known in the art, and depending on the host cells used to produce the lactonases of the invention. Generally, the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with bacteria and *fungi* finding use in many embodiments.

A. Preparation of Variants

The nucleic acids encoding the variant lactonases of the invention can be prepared using any mutagenesis procedure known in the art, such as site-directed mutagenesis and synthetic gene construction as are well known in the art.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips. A preferred technique is GenScript®.

i) Regulatory Sequences

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* lactonase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell can be used.

In some embodiments, terminators for filamentous fungal host cells are obtained from the genes for *Aspergillus nidulans* anthranilate synthase, *Aspergillus niger* lactonase, *Aspergillus niger* alpha-glucosidase, *Aspergillus oryzae* TAKA amylase, and *Fusarium oxysporum* trypsin-like protease.

In some embodiments, terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence can also be an mRNA stabilizer region downstream of a promoter and upstream of the coding sequence of a gene which increases expression of the gene.

Examples of suitable mRNA stabilizer regions are obtained from a *Bacillus thuringiensis* crylllA gene (WO 94/25612) and a *Bacillus subtilis* SP82 gene (Hue et al., 1995, Journal of Bacteriology 177: 3465-3471).

The control sequence can also be a leader, a nontranslated region of an mRNA that is important for translation by the host cell. The leader sequence is operably linked to the 5'-terminus of the polynucleotide encoding the variant. Any leader that is functional in the host cell may be used.

In some embodiments, leaders for filamentous fungal host cells are obtained from the genes for *Aspergillus oryzae* TAKA amylase and *Aspergillus nidulans* triose phosphate isomerase.

In some embodiments, suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence can also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

In some embodiments, polyadenylation sequences for filamentous fungal host cells are obtained from the genes for *Aspergillus nidulans* anthranilate synthase, *Aspergillus niger* lactonase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant glucoamhylase being expressed into the cell's secretory pathway. The 5'-end of the coding sequence of the polynucleotide may inherently contain a signal peptide coding sequence naturally linked in translation reading frame with the segment of the coding sequence that encodes the variant glucoamhylase. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant glucoamhylase. However, any signal peptide coding sequence that directs the expressed variant into the secretory pathway of a host cell may be used.

Effective signal peptide coding sequences for filamentous fungal host cells are the signal peptide coding sequences obtained from the genes for *Aspergillus niger* neutral amylase, *Aspergillus niger* lactonase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous *fungi*, the *Aspergillus niger* lactonase promoter, *Aspergillus oryzae* TAKA alpha-amylase promoter, and *Aspergillus oryzae* lactonase promoter can be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

1. Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector can be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used. Vectors contemplated for use with the methods of the invention include both integrating and non-integrating vectors.

In some embodiments, the vector contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

In some embodiments, the vector contains an element(s) that permits integration of the vector into the host cell's genome or autonomous replication of the vector in the cell independent of the genome.

For integration into the host cell genome, the vector can rely on the polynucleotide's sequence encoding the variant or any other element of the vector for integration into the genome by homologous or non-homologous recombination. Alternatively, the vector can contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector can further comprise an origin of replication enabling the vector to replicate autonomously in the host cell in question. The origin of replication can be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, Gene 98: 61-67; Cullen et al., 1987, Nucleic Acids Res. 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention can be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

2. Codon Optimization

Codon optimization can be employed with any of the variant lactonase polypeptides of the present invention, in order to optimize expression in the host cell employed. Such methods are well known in the art and described in, for example, WO 2007/142954. In heterologous expression systems, optimization steps can improve the ability of the host to produce the desired variant lactonase polypeptides. Protein expression is governed by a host of factors including those that affect transcription, mRNA processing, and stability and initiation of translation. The polynucleotide optimization steps can include steps to improve the ability of the host to produce the foreign protein as well as steps to assist the researcher in efficiently designing expression constructs. Optimization strategies can include, for example, the modification of translation initiation regions, alteration of mRNA structural elements, and the use of different codon biases. The following paragraphs discuss potential problems that may result in reduced heterologous protein expression, and techniques that may overcome these problems.

In some embodiments, reduced heterologous protein expression results from a rare codon-induced translational pause. A rare codon-induced translational pause includes the presence of codons in the polynucleotide of interest that are rarely used in the host organism can have a negative effect on protein translation due to their scarcity in the available tRNA pool. One method of improving optimal translation in the host organism includes performing includes performing codon optimization which can result in rare host codons being modified in the synthetic polynucleotide sequence.

In some embodiments, reduced heterologous protein expression results from by alternate translational initiation. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes modifying putative internal RBS sequences from an optimized polynucleotide sequence.

In some embodiments, reduced heterologous protein expression occurs through repeat-induced polymerase slippage. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage includes altering extended repeats of G or C nucleotides.

In some embodiments, reduced heterologous protein expression occurs through interfering secondary structures. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

In some embodiments, restriction sites can effect heterologous protein expression. By modifying restriction sites that could interfere with subsequent sub-cloning of transcription units into host expression vectors a polynucleotide sequence can be optimized.

Optimizing a DNA sequence can negatively or positively affect gene expression or protein production. For example, modifying a less-common codon with a more common codon may affect the half life of the mRNA or alter its structure by introducing a secondary structure that interferes with translation of the message. It may therefore be necessary, in certain instances, to alter the optimized message.

AUG or a portion of a gene can be optimized. In some embodiments, the desired modulation of expression is achieved by optimizing essentially the entire gene. In other embodiments, the desired modulation will be achieved by optimizing part but not all of the gene.

The codon usage of any coding sequence can be adjusted to achieve a desired property, for example high levels of expression in a specific cell type. The starting point for such an optimization may be a coding sequence with 100% common codons, or a coding sequence which contains a mixture of common and non-common codons.

Two or more candidate sequences that differ in their codon usage can be generated and tested to determine if they possess the desired property. Candidate sequences can be evaluated by using a computer to search for the presence of regulatory elements, such as silencers or enhancers, and to search for the presence of regions of coding sequence which could be converted into such regulatory elements by an alteration in codon usage. Additional criteria can include enrichment for particular nucleotides, e.g., A, C, G or U, codon bias for a particular amino acid, or the presence or absence of particular mRNA secondary or tertiary structure. Adjustment to the candidate sequence can be made based on a number of such criteria.

Promising candidate sequences are constructed and then evaluated experimentally. Multiple candidates may be evaluated independently of each other, or the process can be iterative, either by using the most promising candidate as a new starting point, or by combining regions of two or more candidates to produce a novel hybrid. Further rounds of modification and evaluation can be included.

Modifying the codon usage of a candidate sequence can result in the creation or destruction of either a positive or negative element. In general, a positive element refers to any element whose alteration or removal from the candidate sequence could result in a decrease in expression of the therapeutic protein, or whose creation could result in an increase in expression of a therapeutic protein. For example, a positive element can include an enhancer, a promoter, a downstream promoter element, a DNA binding site for a positive regulator (e.g., a transcriptional activator), or a sequence responsible for imparting or modifying an mRNA secondary or tertiary structure. A negative element refers to any element whose alteration or removal from the candidate sequence could result in an increase in expression of the therapeutic protein, or whose creation would result in a decrease in expression of the therapeutic protein. A negative element includes a silencer, a DNA binding site for a negative regulator (e.g., a transcriptional repressor), a transcriptional pause site, or a sequence that is responsible for imparting or modifying an mRNA secondary or tertiary structure. In general, a negative element arises more frequently than a positive element. Thus, any change in codon usage that results in an increase in protein expression is more likely to have arisen from the destruction of a negative element rather than the creation of a positive element. In addition, alteration of the candidate sequence is more likely to destroy a positive element than create a positive element. In some embodiments, a candidate sequence is chosen and modified so as to increase the production of a therapeutic protein. The candidate sequence can be modified, e.g., by sequentially altering the codons or by randomly altering the codons in the candidate sequence. A modified candidate sequence is then evaluated by determining the level of expression of the resulting therapeutic protein or by evaluating another parameter, e.g., a parameter correlated to the level of expression. A candidate sequence which produces an increased level of a therapeutic protein as compared to an unaltered candidate sequence is chosen.

In some embodiments, one or a group of codons can be modified, e.g., without reference to protein or message structure and tested. Alternatively, one or more codons can be chosen on a message-level property, e.g., location in a region of predetermined, e.g., high or low GC content, location in a region having a structure such as an enhancer or silencer, location in a region that can be modified to introduce a structure such as an enhancer or silencer, location in a region having, or predicted to have, secondary or tertiary structure, e.g., intra-chain pairing, inter-chain pairing, location in a region lacking, or predicted to lack, secondary or tertiary structure, e.g., intra-chain or inter-chain pairing. A particular modified region is chosen if it produces the desired result.

Methods which systematically generate candidate sequences are useful. For example, one or a group, e.g., a contiguous block of codons, at various positions of a synthetic nucleic acid sequence can be modified with common codons (or with non common codons, if for example, the starting sequence has been optimized) and the resulting sequence evaluated. Candidates can be generated by optimizing (or de-optimizing) a given "window" of codons in the sequence to generate a first candidate, and then moving the window to a new position in the sequence, and optimizing (or de-optimizing) the codons in the new position under the window to provide a second candidate. Candidates can be evaluated by determining the level of expression they provide, or by evaluating another parameter, e.g., a parameter correlated to the level of expression. Some parameters can be evaluated by inspection or computationally, e.g., the possession or lack thereof of high or low GC content; a sequence element such as an enhancer or silencer; secondary or tertiary structure, e.g., intra-chain or inter-chain paring.

In some embodiments, the optimized nucleic acid sequence can express the variant lactonase polypeptide of the invention, at a level which is at least 110%, 150%, 200%, 500%, 1,000%, 5,000% or even 10,000% of that expressed by nucleic acid sequence that has not been optimized.

Staring with the amino acid sequence of a variant lactonase, a candidate DNA sequence can be designed. During the design of the synthetic DNA sequence, the frequency of codon usage can be compared to the codon usage of the host expression organism and rare host codons can be modified in the synthetic sequence. Additionally, the synthetic candidate DNA sequence can be modified in order to remove undesirable enzyme restriction sites and add or alter any desired signal sequences, linkers or untranslated regions. The synthetic DNA sequence can be analyzed for the presence of secondary structure that may interfere with the translation process, such as G/C repeats and stem-loop structures. Before the candidate DNA sequence is synthesized, the optimized sequence design can be checked to verify that the sequence correctly encodes the desired amino acid sequence. Finally, the candidate DNA sequence can be synthesized using DNA synthesis techniques, such as those known in the art.

In some embodiments, the general codon usage in a host organism, such as any of those described herein, can be utilized to optimize the expression of the heterologous polynucleotide sequence in the host organism. The percentage and distribution of codons that rarely would be considered as preferred for a particular amino acid in the host expression system can be evaluated. Values of 5% and 10% usage can be used as cutoff values for the determination of rare codons.

VIII. HOST CELLS AND PRODUCTION STRAINS

As will be appreciated by those in the art, there are a wide variety of production host organisms for the recombinant production of the variant lactonases of the invention, including, but not limited to bacterial cells and fungal cells including yeast. In addition, while the G1P parent lactonase is unglycoslyated, glycosylation by production in yeast and *fungi* does not adversely affect the lactonase activity.

The present invention also relates to recombinant host cells, comprising a polynucleotide encoding a variant glucoamlyase of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source. In some embodiments, the host cell exhibits transitory expression of the variant glucoamlyase. In some embodiments, the host cell is a stably transfected host or a host cell that stably (i.e., permanently) expresses the variant lactonase. In some embodiments, the host cell is a production host cell.

The host cell can be any cell useful in the recombinant production of a variant, e.g., a prokaryote or a eukaryote. Such host cells include but are not limited to bacterial, fungal, and yeast cells. The host cell can also be a eukaryote, such as a plant, yeast or fungal cell.

The host cell can be a fungal cell. "*Fungi*" as used herein includes the phyla *Ascomycota, Basidiomycota, Chytridiomycota*, and *Zygomycota* as well as the *Oomycota* and all mitosporic *fungi* (as defined by Hawksworth et al., In, Ainsworth and Bisby's Dictionary of The *Fungi*, 8th edition, 1995, CAB International, University Press, Cambridge, UK).

The fungal host cell can be a yeast cell. "Yeast" as used herein includes ascosporogenous yeast (*Endomycetales*), basidiosporogenous yeast, and yeast belonging to the *Fungi Imperfecti* (*Blastomycetes*). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous *fungi*" include all filamentous forms of the subdivision *Eumycota* and *Oomycota* (as defined by Hawksworth et al., 1995, supra). The filamentous *fungi* are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium*

*queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al, 1984, *Proc. Natl. Acad. Sci. USA* 81: 1470-1474, and Christensen et al., 1988, *BiolTechnology* 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, *Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

IX. COMPOSITIONS

The present invention also provides compositions comprising a variant lactonase. In some embodiments, the composition comprises a carrier and/or an excipient. In some embodiments, the compositions are enriched in such a variant lactonase polypeptide of the present invention. The term "enriched" indicates that the lactonase activity of the composition has been increased, e.g., with an enrichment factor of at least 1. In some embodiments, the compositions are formulated to provide desirable characteristics such as low color, low odor and acceptable storage stability.

In some embodiments, the composition comprises a variant lactonase polypeptide of the present invention as the major enzymatic component, e.g., a mono-component composition. This composition can be used as an additive to fish feed stocks.

X. METHODS OF PRODUCTION

The present invention also relates to methods of producing a variant lactonase polypeptide, comprising: (a) cultivating a host cell of the present invention under conditions suitable for expression of the variant lactonase polypeptide; and (b) optionally recovering the variant lactonase polypeptide.

The host cells are cultivated in a nutrient medium suitable for production of the variant lactonase polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the variant lactonase polypeptide is secreted into the nutrient medium, the variant lactonase polypeptide can be recovered directly from the medium. If the variant is not secreted, it can be recovered from cell lysates.

The variant lactonase polypeptide can be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant lactonase polypeptide.

The variant lactonase polypeptide can be recovered using methods known in the art. For example, the variant lactonase polypeptide can be recovered from the nutrient medium by conventional procedures including, but not limited to, collection, centrifugation, filtration, extraction, spray-drying, evaporation, or precipitation.

The variant can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant. In a particular embodiment variant lactonase of the invention is not recovered and the host cell is a yeast host cell. In particular, the yeast is a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell. In some embodiments, the yeast is *Saccharomyces cerevisiae*.

XI. LACTONASE FORMULATIONS AND USES

As discussed herein, the use of lactonase in animal feeds has a number of benefits, including antibacterial properties, as well as the improvement to the intestinal biome, resulting in general health benefits. In some embodiments, the variant lactonases of the invention are formulated and added to feed or can be made as a component of the feed. In the former case, the feed stock addition of lactonase can be done by formulating the lactonase on a carrier feed such as wheat flour.

As will be appreciated by those in the art, the formulation of the variant lactonases of the invention depends on its end use and the associated conditions. Suitable formulations for the variant lactonases of the invention include liquid formulations, dried formulations (including spray dried formulations), powdered formulations, granular formulations, and pelleted formulations.

In some embodiments, the enzyme composition (i.e., polypeptide compositions) of the present invention can be in any form suitable for use, such as, for example, a crude fermentation broth with or without cells removed, a cell lysate with or without cellular debris, a semi-purified or purified enzyme composition, or a host cell, as a source of the enzymes.

In some embodiments, the enzyme composition can be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In some embodiments, the dosage of the polypeptide composition of the invention and other conditions under which the composition is used may be determined on the basis of methods known in the art.

In one embodiment, the lactonases are added to animal feed stock and pelleted as is known in the art, such that the feed is formed with lactonase in it. In other embodiments, the lactonase can be sprayed or dosed in a liquid form into animal feed.

XII. EXAMPLES

A. Example 1: Gene Synthesis and Cloning

The starting gene of lactonase (UniProKB accession number: C6L862) was synthesized by GenScript. The synthesized gene was cloned into the pET-20b(+) vector (Novagen EMD Millipore, USA: catalogue #69739).

B. Example 2: Mutant Collection Design and Construction

In the first generation of improvement, the starting lactonase gene was used as the parent (G1P). To improve the thermostability and pH tolerance of G1P, 4 mutant collections were designed based on G1P protein sequence. The design includes one to multiple specific mutations per variant. The mutant collections were constructed using the QuickChange® Lightning kit (Agilent Technologies, Santa Clara, Calif.) and subsequently cloned into the pET-20b (+) vector (Novagen EMD Millipore, USA: catalogue #69739).

In the second generation of improvement, one improved variant from the first generation was used as the generation 2 parent (G2P). To further improve the thermostability and pH tolerance of G2P, one mutant collections were designed based on the favorable mutations identified in the first generation. The design includes one to multiple specific mutations per variant. The mutant collections were subsequently constructed using the QuickChange® Lightning kit (Agilent Technologies, Santa Clara, Calif.).

C. Example 3: Preparation of HTP Lactonase-Containing Wet Cell Pellets

BL21(DE3) E. coli cells (ThermoFisher Scientific, USA: Catalogue # C6000-03) comprising recombinant lactonase-encoding genes from single colonies were inoculated into individual wells of 96 wells shallow microtiter plates holding 180 µl LB containing 1% glucose and 100 µg/mL ampicillin The cultures were grown overnight at 30° C., 200 rpm and 85% humidity. 20 µL of the overnight culture from each well was transferred into the corresponding wells of 96 deep well plates containing 380 mL Terrific Broth (TB) and 100 µg/mL ampicillin The deep-well plates were incubated for 2.5-3.0 hours (OD600 0.6-0.8) at 37° C., 250 rpm and 85% humidity. The cell cultures were then induced by IPTG to a final concentration of 1 mM and incubated overnight under the same conditions as originally used. The cells were then pelleted using centrifugation at 4000 rpm for 10 min at 4° C. The supernatants were discarded and the pellets frozen at −80° C. prior to lysis.

D. Example 4: Lysis of the HTP Lactonase Plates

150 µL of B-PER bacterial protein extraction reagent (ThermoFisher Scientific, USA: Catalogue #78248) was added to the cell paste in each well as described above. The cells were lysed at room temperature for 1.5 hours with shaking on a bench top shaker. The plate was then centrifuged for 10 min at 4000 rpm and 4° C. The clear supernatants were used to perform biochemical assays to determine activity, pH tolerance and thermostability.

E. Example 5: Initial Screening of Candidates: Activity/pH/Thermostability Profile 1. Thermoactivity Profile:

For the thermo activity profile of G1P, the lysate from Example 4 was 40-fold diluted using 0.05M Tris-HCl, pH 7.2. In 96 well shallow microtiter plates, 25 µl of the diluted lysate was added to 25 µl of N-(3-Oxooctanoyl)-L-homoserine lactone substrate (C12H19NO4, FW: 241.3) prepared in 4% DMSO to a final concentration of 8 mM substrate in reaction, pH 7.2. The reaction was incubated at 30° C., 50° C., and 60° C., 200 rpm for 30 minutes. The reaction was quenched with 75 µl of quenching reagent containing 3.5 M NaOH: 2 M hydroxylamine hydrochloride:: 1:1. Following quenching 75 µl of coloring reagent was added. The coloring reagent was freshly prepared by mixing adding equal volumes of 10% FeCl3 in 4 M HCl to 95% EtOH. After shaking the plates for 1-2 minutes, they were subjected to centrifugation at 4000 rpm for 2 minutes. The plates absorbance was then read at 530 nm. The results are shown in FIG. 1.

2. pH Profile:

For the pH profile of G1P, the lysate from Example 4 was 40-fold diluted at 0.05M buffers, pH 3-8 (pH 3: citrate, pH 4 and 5: sodium acetate, pH 6: sodium phosphate, pH land 8: Tris-HCl). In 96 well shallow microtiter plates, 25 µl of the diluted lysate was added to 25 µl of N-(3-Oxooctanoyl)-L-homoserine lactone substrate ($C_{12}H_{19}NO_4$, FW: 241.3) prepared in 4% DMSO to a final concentration of 8 mM substrate in reaction at their respective pH buffers. The reaction was incubated at 30° C., 200 rpm for 30 minutes. The reaction was quenched with 75 µl of quenching reagent containing 3.5 M NaOH:2 M hydroxylamine hydrochloride: 1:1. Following quenching 75 µl of coloring reagent was added. The coloring reagent was freshly prepared by mixing adding equal volumes of 10% $FeCl_3$ in 4 M HCl to 95% EtOH. After shaking the plates for 1-2 minutes, they were subjected to centrifugation at 4000 rpm for 2 minutes. The plates absorbance was then read at 530 nm. The results are shown in FIG. 2.

3. Thermostability Profile:

The lysate from Example 4 was 40-fold diluted using 0.05M Tris-HCl, pH 7.2. 70 µl of the diluted lysate was transferred to PCR plates and heated at 30-70° C. in thermocyclers for 10 minutes. Post challenge, 25 µl of the diluted lysate was added to 25 µl of N-(3-Oxooctanoyl)-L-homoserine lactone substrate (C12H19NO4, FW: 241.3) prepared in 4% DMSO to a final concentration of 8 mM substrate in reaction, pH 7.2. The reaction was incubated at 30° C., 200 rpm for 30 minutes. The reaction was quenched with 75 µl of quenching reagent containing 3.5 M NaOH:2 M hydroxylamine hydrochloride: 1:1. Following quenching 75 µl of coloring reagent was added. The coloring reagent was freshly prepared by mixing adding equal volumes of 10% FeCl3 in 4 M HCl to 95% EtOH. After shaking the plates for 1-2 minutes, they were subjected to centrifugation at 4000 rpm for 2 minutes. The plates absorbance was then read at 530 nm. The results are shown in FIG. 3.

F. Example 6: Untreated Enzymatic Assay

For the untreated assay, the lysate from Example 4 was 40-fold diluted using 0.05M Tris-HCl, pH 7.2. In 96 well shallow microtiter plates, 25 µl of the diluted lysate was added to 25 µl of N-(3-Oxooctanoyl)-L-homoserine lactone substrate ($C_{12}H_{19}NO_4$, FW: 241.3) prepared in 4% DMSO to a final concentration of 8 mM substrate in reaction, pH 7.2. The reaction was incubated at 30° C., 200 rpm for 30 minutes. The reaction was quenched with 75 µl of quenching reagent containing 3.5 M NaOH: 2 M hydroxylamine hydrochloride:: 1:1. Following quenching 75 µl of coloring reagent was added. The coloring reagent was freshly prepared by mixing adding equal volumes of 10% FeCl3 in 4 M HCl to 95% EtOH. After shaking the plates for 1-2 minutes, they were subjected to centrifugation at 4000 rpm for 2 minutes. The plates absorbance was then read at 530 nm. The enzyme activity of variant was compared to the parent under the same conditions to determine activity improvement. The results are shown in FIGS. 4-5.

G. Example 7: Enzymatic Assay with Temperature Challenge

The lysate from Example 4 was 40-fold diluted using 0.05M Tris-HCl, pH 7.2. 70 µl of the diluted lysate was transferred to PCR plates and heated at 55.5° C. for 10 minutes in thermocyclers for screening of generation 1 (G1) and generation 2 (G2) variants respectively. Post challenge, 25 µl of the diluted lysate was added to 25 µl of N-(3-Oxooctanoyl)-L-homoserine lactone substrate ($C_{12}H_{19}NO_4$, FW: 241.3) prepared in 4% DMSO to a final concentration of 8 mM substrate in reaction, pH 7.2. The reaction was incubated at 30° C., 200 rpm for 30 minutes. The reaction was quenched with 75 µl of quenching reagent containing 3.5 M NaOH: 2 M hydroxylamine hydrochloride:: 1:1. Following quenching 75 µl of coloring reagent was added. The coloring reagent was freshly prepared by mixing adding equal volumes of 10% FeCl3 in 4 M HCl to 95% EtOH. After shaking the plates for 1-2 minutes, they were subjected to centrifugation at 4000 rpm for 2 minutes. The plates absorbance was then read at 530 nm. The enzyme activity of variant was compared to the parent under the same conditions to determine activity improvement. The results are shown in FIGS. 4-5.

H. Example 8: Enzymatic Assay with pH Challenge

For the pH challenge assay, the lysate from Example 4 was 40-fold diluted using 0.1M sodium acetate, pH 4.8. In 96 well shallow microtiter plates, 25 µl of the diluted lysate was added to 25 µl of N-(3-Oxooctanoyl)-L-homoserine lactone substrate ($C_{12}H_{19}NO_4$, FW: 241.3) prepared in 4% DMSO to a final concentration of 8 mM substrate in reaction, pH 4.8. The reaction was incubated at 30° C., 200 rpm for 30 minutes. The reaction was quenched with 75 µl of quenching reagent containing 3.5 M NaOH: 2 M hydroxylamine hydrochloride:: 1:1. Following quenching 75 µl of coloring reagent was added. The coloring reagent was freshly prepared by mixing adding equal volumes of 10% FeCl3 in 4 M HCl to 95% EtOH. After shaking the plates for 1-2 minutes, they were subjected to centrifugation at 4000 rpm for 2 minutes. The plates absorbance was then read at 530 nm. The enzyme activity of variant was compared to the parent under the same conditions to determine activity improvement. The results are shown in FIGS. 4-5.

I. Example 9: Validating Thermostability Profile of the Best Variants from Two Rounds of Enzyme Improvement The lysate from example 4 was 40-fold diluted using 0.05M Tris-HCl, pH 7.2. 70 µl of the diluted lysate was transferred to PCR plates and heated at 30-70° C. in thermocyclers for 10 minutes. Post challenge, 25 µl of the diluted lysate was added to 25 µl of N-(3-Oxooctanoyl)-L-homoserine lactone substrate ($C_{12}H_{19}NO_4$, FW: 241.3) prepared in 4% DMSO to a final concentration of 8 mM substrate in reaction, pH 7.2. The reaction was incubated at 30° C., 200 rpm for 30 minutes. The reaction was quenched with 75 µl of quenching reagent containing 3.5 M NaOH: 2 M hydroxylamine hydrochloride:: 1:1. Following quenching 75 µl of coloring reagent was added. The coloring reagent was freshly prepared by mixing adding equal volumes of 10% FeCl3 in 4 M HCl to 95% EtOH. After shaking the plates for 1-2 minutes, they were subjected to centrifugation at 4000 rpm for 2 minutes. The plate absorbance was then read at 530 nm. Residual activity calculation was done by comparing the activity to the enzyme left at room temperature for 10 minutes. The results are shown in FIG. 6.

What is claimed is:

1. A composition comprising a variant lactonase enzyme comprising an amino acid substitution as compared to SEQ ID NO:1, wherein said amino acid substitution is at a position selected from 17, 32, 34, 35, 41, 50, 62, 66, 68, 69, 70, 74, 76, 77, 79, 80, 81, 83, 84, 114, 120, 122, 123, 127, 132, 136, 139, 155, 162, 164, 184, 185, 188, 189, 192, 193, 195, 218, 221, 222 and 244, wherein said variant lactonase enzyme retains lactonase activity and is at least 95% identical to SEQ ID NO:1.

2. A composition according to claim 1 wherein said amino acid substitution is selected from L17V, F32L, D34A, D34E, D34G, D34K, D34Q, D34S, G35S, V41F, A50P, T62A, D66E, L68V, A69C, A69I, A69K, A69Q, A69T, A69V, Q70N, Q70S, Q70Y, N74H, V76A, V76E, V76K, V76L, V76N, V76R, V76S, I77V, G79A, E80G, L81P, V83I, I84V, Q114H, G120A, G120H, G120P, G120R, G120S, G120T, V122I, Q123K, G127A, A132E, L136V, H139K, H139T, A155D, S162C, S162H, S162N, R164K, A184N, A185E, S188D, S188N, S188R, G189R, R192M, I193V, E195A, E218A, E218M, E218N, E218T, Q221H, A222T, E244C, E244G, E244H, E244K, E244R, E244S and E244T.

3. A composition according to claim 1 wherein said variant enzyme comprises the amino acid substitutions D66E/E80G/V83I/L136V.

4. A composition according to claim 3 wherein said variant enzyme further comprises an amino acid substitution selected from L17V, F32L, D34A, D34E, D34G, D34K, D34Q, D34S, G35S, V41F, A50P, T62A, L68V, A69C, A69I, A69K, A69Q, A69T, A69V, Q70N, Q70S, Q70Y, N74H, V76A, V76E, V76K, V76L, V76N, V76R, V76S, I77V, G79A, L81P, I84V, Q114H, G120A, G120H, G120P, G120R, G120S, G120T, V122I, Q123K, G127A, A132E, H139K, H139T, A155D, S162C, S162H, S162N, R164K, A184N, A185E, S188D, S188N, S188R, G189R, R192M, I193V, E195A, E218A, E218M, E218N, E218T, Q221H, A222T, E244C, E244G, E244H, E244K, E244R, E244S and E244T.

5. A composition according to claim 1 wherein said variant enzyme comprises the amino acid substitutions D34K/D66E/E80G/L136V/A184N/G189P.

6. A composition according to claim 5 wherein said variant enzyme further comprises an amino acid substitution selected from L17V, F32L, G35S, V41F, A50P, T62A, L68V, A69C, A69I, A69K, A69Q, A69T, A69V, Q70N, Q70S, Q70Y, N74H, V76A, V76E, V76K, V76L, V76N, V76R, V76S, I77V, G79A, L81P, I84V, Q114H, G120A, G120H, G120P, G120R, G120S, G120T, V122I, Q123K, G127A, A132E, H139K, H139T, A155D, S162C, S162H, S162N, R164K, A185E, S188D, S188N, S188R, R192M, I193V, E195A, E218A, E218M, E218N, E218T, Q221H, A222T, E244C, E244G, E244H, E244K, E244R, E244S and E244T.

7. A composition according to claim 1 wherein said variant enzyme has an amino acid substitution set selected from D66E/Q114H, G35S/V41F, G35S, G35S/E195A, G189R/E195A, L17V/G35S, L17V/G35S/I77V/L136V/G189R, L17V/G35S/D66E, L17V/D66E/L136V, A132E, G189R, L17V/D66E, G35S/Q114H, Q114H/G189R, D66E/V83I, D66E/E80G/V83I/L136V, G35S/D66E/V83I/A222T, D66E/I77V/E80G/V83I/Q114H/A132E/G189R, G120S, A69I, A69V, D34E, N74H, G120T, G120H, A69C, D34A, G127A, A69K, A69Q, G120R, D34G, E218T, A69T, D34Q, G120P, A184N, G120A, E218M, E218N, D34K, D34S, E218A, V76S, E244H, S162N, S162C, E244C, S188D, S188R, V76K, A50P, H139T, V76R, H139K, Q123K/R164K, E244K, S162H, E244S, Q70S, E244T, E244R, Q70N, Q70Y, V76E, V76L, V76A, E244G, S188N, V76N, L81P, L81P/I84V, T62A/G79A/R164K/I193V, G79A/L81P, G79A/I84V/V122I, T62A/L81P/V122I/I193V, T62A/G79A/L81P, T62A/G79A, L81P/A185E, G79A/L81P/I84V/A155D, L68V/L81P/I84V/A155D/I193V, L81P/I84V/I193V, F32L/L81P/I84V/I193V, L68V/L81P/I84V/R164K, G79A, G79A/V122I/R164K, G79A/I84V, V122I/I193V/Q221H, L81P/V122I, T62A/G79A/L81P/I193V/Q221H, T62A/L68V/V122I/R164K, T62A/L81P/I84V, V122I, G79A/V122I, G79A/I193V, D66E/E80G/V83I/L136V/D34K/A184N/G189R, D66E/E80G/V83I/L136V/D34K/A184N/G189R/E218T, D66E/E80G/V83I/L136V/D34K, D66E/E80G/V83I/L136V/D34K/A184N, D66E/E80G/L136V/D34K, D66E/E80G/V83I/L136V/D34K/A184N/E218T, D66E/E80G/L136V, D66E/E80G/L136V/D34K/A184N/G189R/E218T, D66E/E80G/L136V/D34K/G189R, D66E/E80G/V83I/L136V/R192M, D66E/E80G/L136V/D34K/G189R/E218T, D66E/E80G/L136V/D34K/A184N/G189R, D66E/E80G/V83I/L136V/A184N/G189R and D66E/E80G/L136V/D34K/E218T.

8. A composition according to claim 1 further comprising animal feed.

9. A nucleic acid encoding the variant lactonase enzyme of claim 1.

10. An expression vector comprising the nucleic acid of claim 9.

11. A host cell comprising the expression vector of claim 10.

12. A method of making a variant lactonase enzyme comprising culturing the host cell of claim 11 under conditions wherein said enzyme is produced, and recovering said enzyme.

* * * * *

SEQUENCE LISTING

```
<160> NUMBER OF SEQ ID NOS: 220

<210> SEQ ID NO 1
<211> LENGTH: 251
<212> TYPE: PRT
<213> ORGANISM: Artificial Sequence
<220> FEATURE:
<223> OTHER INFORMATION: Synthetic Lactonase (CL00023198 G1P)

<400> SEQUENCE: 1

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
```

```
            20                  25                  30
Thr Asp Gly Phe Thr Val Val Arg Val Asp Leu Arg Gly His Gly Ala
             35                  40                  45

Ser Ala Ala Glu Glu Pro Tyr Asp Ile Pro Thr Leu Ala Thr Asp Val
 50                  55                  60

His Asp Thr Leu Ala Gln Leu Ala Glu Asn Asp Val Ile Pro Gly Glu
 65                  70                  75                  80

Leu Pro Val Ile Val Gly His Ser Met Gly Gly Ile Val Ala Thr Ala
                 85                  90                  95

Tyr Gly Ala Leu Phe Pro Ala Arg Ala Ile Val Asn Val Asp Gln Pro
             100                 105                 110

Leu Gln Leu Ala Gly Met Gln Gly Gln Val Gln Gln Ala Glu Gly Met
         115                 120                 125

Leu Arg Gly Ala Asp Phe Pro Leu Phe Ile His Gly Met Phe Ala Gln
     130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                 165                 170                 175

Glu Asp Ser Pro Glu Glu Leu Ala Ala Leu Val Ser Gly Leu Thr Arg
             180                 185                 190

Ile Pro Glu Asp Val Pro Tyr Leu Val Ile Thr Gly Leu Asp Ala Gly
         195                 200                 205

Pro Glu Tyr Ala Ala Trp Leu Gln Arg Glu Ile Pro Gln Ala Val Gln
     210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                 245                 250

<210> SEQ ID NO 2
<211> LENGTH: 753
<212> TYPE: DNA
<213> ORGANISM: Artificial Sequence
<220> FEATURE:
<223> OTHER INFORMATION: Synthetic Lactonase  (CL00023198 G1P)

<400> SEQUENCE: 2
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgaccccgca     720
cggttcgtcg agcgcgtcga ggctttcgtc cgc                                  753
```

<210> SEQ ID NO 3
<211> LENGTH: 251
<212> TYPE: PRT
<213> ORGANISM: Artificial Sequence
<220> FEATURE:
<223> OTHER INFORMATION: Synthetic Lactonase (CL00025408)

<400> SEQUENCE: 3

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu His Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 4
<211> LENGTH: 753
<212> TYPE: DNA
<213> ORGANISM: Artificial Sequence
<220> FEATURE:
<223> OTHER INFORMATION: Synthetic Lactonase (CL00025408)

<400> SEQUENCE: 4
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga acgacgtgat ccccggggaa     240
ctgccggtga tcgtcggcca ctcgatgggc gggatcgtcg cgacggcgta cggcgcgctc     300

-continued

```
ttccccgcgc gggcgatcgt caacgtggac cagcctctcc acctcgcggg catgcagggc      360
caggtgcagc aggcggaggg gatgctccgc ggggcggact tcccgctgtt catccacggc      420
atgttcgcgc agatggcggg cggcctggat gccgaggagc tggcgcgggt gaatggcatc      480
cggtctccga ggcaggacgt cgtcctcggg atgtggcggc cgcttctcga ggactcaccc      540
gaagaactgg cggcgctcgt gagcggtctg acgaggatcc cggaggacgt cccgtacctc      600
gtgatcacgg gtctcgatgc cgggccagag tacgcggcgt ggctgcagcg ggagatcccg      660
caggccgtcc aggaggtctg gcagccgccg acccactacc cgcacctcgt cgacccggca      720
cggttcgtcg agcgcgtcga ggctttcgtc cgc                                   753
```

<210> SEQ ID NO 5
<211> LENGTH: 251
<212> TYPE: PRT
<213> ORGANISM: Artificial Sequence
<220> FEATURE:
<223> OTHER INFORMATION: Synthetic Lactonase (CL00025417)

<400> SEQUENCE: 5

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Ser Phe Thr Val Val Arg Phe Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 6
<211> LENGTH: 753
<212> TYPE: DNA
<213> ORGANISM: Artificial Sequence
<220> FEATURE:
<223> OTHER INFORMATION: Synthetic Lactonase (CL00025417)

<400> SEQUENCE: 6

```
atgatcctcg cccacgacgt gtcgggctcc ggcccgctgc tggtcctcct gcacggcatc      60
accgaagacc gccgcagctg ggatccggtc gatttcaccg actccttcac ggtcgtacgg     120
ttcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc      420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc gcacctcgt cgacccggca      720
cggttcgtcg agcgcgtcga ggctttcgtc cgc                                  753
```

<210> SEQ ID NO 7
<211> LENGTH: 251
<212> TYPE: PRT
<213> ORGANISM: Artificial Sequence
<220> FEATURE:
<223> OTHER INFORMATION: Synthetic Lactonase (CL00025481)

<400> SEQUENCE: 7

```
Met Ile Leu Ala His Asp Val Ser Gly Ser Gly Pro Leu Leu Val Leu
 1               5                  10                  15

Leu His Gly Ile Thr Glu Asp Arg Arg Ser Trp Asp Pro Val Asp Phe
            20                  25                  30

Thr Asp Ser Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205
```

Pro Glu Tyr Ala Ala Trp Leu Gln Arg Glu Ile Pro Gln Ala Val Gln
                210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 8
<211> LENGTH: 753
<212> TYPE: DNA
<213> ORGANISM: Artificial Sequence
<220> FEATURE:
<223> OTHER INFORMATION: Synthetic Lactonase (CL00025481)

<400> SEQUENCE: 8

| | |
|---|---|
| atgatcctcg cccacgacgt gtcgggctcc ggcccgctgc tggtcctcct gcacggcatc | 60 |
| accgaagacc gccgcagctg ggatccggtc gatttcaccg actccttcac ggtcgtgcgg | 120 |
| gtcgacctgc gcgggcacgg gcatcagcc gccgaagaac cgtacgacat ccccacgctc | 180 |
| gcgaccgacg tgcacgacac cctcgcgcag ctcgccgaga acgacgtgat ccccggggaa | 240 |
| ctgccggtga tcgtcggcca ctcgatgggc gggatcgtcg cgacggcgta cggcgcgctc | 300 |
| ttccccgcgc gggcgatcgt caacgtggac cagcctctcc agctcgcggg catgcagggc | 360 |
| caggtgcagc aggcggaggg gatgctccgc ggggcggact cccgctgttt catccacggc | 420 |
| atgttcgcgc agatggcggg cggcctggat gccgaggagc tggcgcgggt gaatggcatc | 480 |
| cggtctccga ggcaggacgt cgtcctcggg atgtggcggc gcttctcga ggactcaccc | 540 |
| gaagaactgg cggcgctcgt gagcggtctg acgaggatcc cggaggacgt cccgtacctc | 600 |
| gtgatcacgg gtctcgatgc cgggccagag tacgcggcgt ggctgcagcg ggagatcccg | 660 |
| caggccgtcc aggaggtctg gcagccgccg acccactacc cgcacctcgt cgacccggca | 720 |
| cggttcgtcg agcgcgtcga ggctttcgtc cgc | 753 |

<210> SEQ ID NO 9
<211> LENGTH: 251
<212> TYPE: PRT
<213> ORGANISM: Artificial Sequence
<220> FEATURE:
<223> OTHER INFORMATION: Synthetic Lactonase (CL00025500)

<400> SEQUENCE: 9

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Ser Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

```
Leu Arg Gly Ala Asp Phe Pro Leu Phe Ile His Gly Met Phe Ala Gln
        130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Ala Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 10
<211> LENGTH: 753
<212> TYPE: DNA
<213> ORGANISM: Artificial Sequence
<220> FEATURE:
<223> OTHER INFORMATION: Synthetic Lactonase (CL00025500)

<400> SEQUENCE: 10

```
atgatcctcg cccacgacgt gtcgggctcc ggcccgctgc tggtcctcct gcacggcatc      60
accgaagacc gccgcagctg ggatccggtc gatttcaccg actccttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240
ctgccggtga tcgtcggcca ctcgatgggg gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggccgacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgaccggca     720
cggttcgtcg agcgcgtcga ggctttcgtc cgc                                  753
```

<210> SEQ ID NO 11
<211> LENGTH: 251
<212> TYPE: PRT
<213> ORGANISM: Artificial Sequence
<220> FEATURE:
<223> OTHER INFORMATION: Synthetic Lactonase (CL00025535)

<400> SEQUENCE: 11

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45
```

```
Ser Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
 65                  70                  75                  80

Leu Pro Val Ile Val Gly His Ser Met Gly Gly Ile Val Ala Thr Ala
                 85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Arg Leu Thr Arg
            180                 185                 190

Ile Pro Ala Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 12
<211> LENGTH: 753
<212> TYPE: DNA
<213> ORGANISM: Artificial Sequence
<220> FEATURE:
<223> OTHER INFORMATION: Synthetic Lactonase (CL00025535)

<400> SEQUENCE: 12
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240 ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagccgcctg acgaggatcc cggccgacgt cccgtacctc     600
gtgatcaccg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753

<210> SEQ ID NO 13
<211> LENGTH: 251
```

<212> TYPE: PRT
<213> ORGANISM: Artificial Sequence
<220> FEATURE:
<223> OTHER INFORMATION: Synthetic Lactonase (CL00025550)

<400> SEQUENCE: 13

```
Met Ile Leu Ala His Asp Val Ser Gly Ser Gly Pro Leu Leu Val Leu
1               5                   10                  15

Val His Gly Ile Thr Glu Asp Arg Arg Ser Trp Asp Pro Val Asp Phe
            20                  25                  30

Thr Asp Ser Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 14
<211> LENGTH: 753
<212> TYPE: DNA
<213> ORGANISM: Artificial Sequence
<220> FEATURE:
<223> OTHER INFORMATION: Synthetic Lactonase (CL00025550)

<400> SEQUENCE: 14

```
atgatcctcg cccacgacgt gtcgggctcc ggcccgctgc tggtcctcgt ccacggcatc      60
accgaagacc gccgcagctg ggatccggtc gatttcaccg actccttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc      420
```

```
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc ggaggacgt cccgtacctc     600 gtgatcacgg tctcgatgc cgggccagag tacgcggcgt ggctgcagcg ggagatcccg     660
caggccgtcc aggaggtctg gcagccgccg acccactacc gcacctcgt cgacccggca     720 cggttcgtcg agcgcgtcga ggctttcgtc cgc                                 753
```

<210> SEQ ID NO 15
<211> LENGTH: 251
<212> TYPE: PRT
<213> ORGANISM: Artificial Sequence
<220> FEATURE:
<223> OTHER INFORMATION: Synthetic Lactonase (CL00025567)

<400> SEQUENCE: 15

```
Met Ile Leu Ala His Asp Val Ser Gly Ser Gly Pro Leu Leu Val Leu
1               5                   10                  15

Val His Gly Ile Thr Glu Asp Arg Arg Ser Trp Asp Pro Val Asp Phe
            20                  25                  30

Thr Asp Ser Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Val Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Arg Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 16
<211> LENGTH: 753
<212> TYPE: DNA
<213> ORGANISM: Artificial Sequence
<220> FEATURE:
<223> OTHER INFORMATION: Synthetic Lactonase (CL00025567)

<400> SEQUENCE: 16

```
atgatcctcg cccacgacgt gtcgggctcc ggcccgctgc tggtcctcgt ccacggcatc      60
accgaagacc gccgcagctg ggatccggtc gatttcaccg actccttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtggt ccccggggaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccggtctt catccacggc      420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagccgcctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc gcacctcgt cgaccgggca     720
cggttcgtcg agcgcgtcga ggctttcgtc cgc                                   753
```

<210> SEQ ID NO 17
<211> LENGTH: 251
<212> TYPE: PRT
<213> ORGANISM: Artificial Sequence
<220> FEATURE:
<223> OTHER INFORMATION: Synthetic Lactonase (CL00025583)

<400> SEQUENCE: 17

```
Met Ile Leu Ala His Asp Val Ser Gly Ser Gly Pro Leu Leu Val Leu
1               5                   10                  15

Val His Gly Ile Thr Glu Asp Arg Arg Ser Trp Asp Pro Val Asp Phe
            20                  25                  30

Thr Asp Ser Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220
```

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 18
<211> LENGTH: 753
<212> TYPE: DNA
<213> ORGANISM: Artificial Sequence
<220> FEATURE:
<223> OTHER INFORMATION: Synthetic Lactonase (CL00025583)

<400> SEQUENCE: 18
atgatcctcg cccacgacgt gtcgggctcc ggcccgctgc tggtcctcgt ccacggcatc      60
accgaagacc gccgcagctg ggatccggtc gatttcaccg actccttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc     420 atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc ggaggacgt cccgtacctc     600 gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                 753

<210> SEQ ID NO 19
<211> LENGTH: 251
<212> TYPE: PRT
<213> ORGANISM: Artificial Sequence
<220> FEATURE:
<223> OTHER INFORMATION: Synthetic Lactonase (CL00025594)

<400> SEQUENCE: 19

Met Ile Leu Ala His Asp Val Ser Gly Ser Gly Pro Leu Leu Val Leu
1               5                   10                  15

Val His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Glu Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
            165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
            245                 250

<210> SEQ ID NO 20
<211> LENGTH: 753
<212> TYPE: DNA
<213> ORGANISM: Artificial Sequence
<220> FEATURE:
<223> OTHER INFORMATION: Synthetic Lactonase (CL00025594)

<400> SEQUENCE: 20

```
atgatcctcg cccacgacgt gtcgggctcc ggcccgctgc tggtcctcgt ccacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga cgacgtgat ccccggggaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccggtcttc catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgaccggca    720
cggttcgtcg agcgcgtcga ggctttcgtc cgc                                 753
```

<210> SEQ ID NO 21
<211> LENGTH: 251
<212> TYPE: PRT
<213> ORGANISM: Artificial Sequence
<220> FEATURE:
<223> OTHER INFORMATION: Artificial Sequence (CL00025622)

<400> SEQUENCE: 21

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Glu Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 22
<211> LENGTH: 753
<212> TYPE: DNA
<213> ORGANISM: Artificial Sequence
<220> FEATURE:
<223> OTHER INFORMATION: Synthetic Lactonase (CL00025622)

<400> SEQUENCE: 22
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240 ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggaggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753

<210> SEQ ID NO 23
<211> LENGTH: 251
<212> TYPE: PRT
<213> ORGANISM: Artificial Sequence
<220> FEATURE:
<223> OTHER INFORMATION: Synthetic Lactonase (CL00025630)

<400> SEQUENCE: 23

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Arg Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 24
<211> LENGTH: 753
<212> TYPE: DNA
<213> ORGANISM: Artificial Sequence
<220> FEATURE:
<223> OTHER INFORMATION: Synthetic Lactonase (CL00025630)

<400> SEQUENCE: 24

```
atgatcctcg cccacgacgt gtcgggctcc ggcccgctgc tggtcctcct gcacggcatc      60
accgaagacc gccgcagctg ggatccggtc gatttcaccg acggcttcac ggtcgtacgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
```

```
gaagaactgg cggcgctcgt gagccgcctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 25
<211> LENGTH: 251
<212> TYPE: PRT
<213> ORGANISM: Artificial Sequence
<220> FEATURE:
<223> OTHER INFORMATION: Synthetic Lactonase (CL00025634)

<400> SEQUENCE: 25

```
Met Ile Leu Ala His Asp Val Ser Gly Ser Gly Pro Leu Leu Val Leu
1               5                   10                  15

Val His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 26
<211> LENGTH: 753
<212> TYPE: DNA
<213> ORGANISM: Artificial Sequence
<220> FEATURE:
<223> OTHER INFORMATION: Synthetic Lactonase (CL00025634)

<400> SEQUENCE: 26

```
atgatcctcg cccacgacgt gtcgggctcc ggcccgctgc tggtcctcgt ccacggcatc    60
accgaagacc gccgcagctg ggatccggtc gatttcaccg acggcttcac ggtcgtgcgg    120
```

```
gtcgacctgc gcgggcacgg ggcatcagcc gccgaagaac cgtacgacat ccccacgctc    180
gcgaccgacg tgcacgagac cctcgcgcag ctcgccgaga cgacgtgat ccccggggaa    240 ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact tcccgctgtt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753

<210> SEQ ID NO 27
<211> LENGTH: 251
<212> TYPE: PRT
<213> ORGANISM: Artificial Sequence
<220> FEATURE:
<223> OTHER INFORMATION: Synthetic Lactonase (CL00025635)

<400> SEQUENCE: 27

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Ser Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu His Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 28
<211> LENGTH: 753
<212> TYPE: DNA
<213> ORGANISM: Artificial Sequence
<220> FEATURE:
<223> OTHER INFORMATION: Synthetic Lactonase (CL00025635)

<400> SEQUENCE: 28

```
atgatcctcg cccacgacgt gtcgggctcc ggcccgctgc tggtcctcct gcacggcatc      60
accgaagacc gccgcagctg ggatccggtc gatttcaccg actccttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240
ctgccggtga tcgtcggcca ctcgatgggc gggatcgtcg cgacggcgta cggcgcgctc     300
ttccccgcgc gggcgatcgt caacgtggac cagcctctcc acctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc ggaggacgt cccgtacctc      600
gtgatcacgg tctcgatgc cgggccagag tacgcggcgt ggctgcagcg ggagatcccg     660
caggccgtcc aggaggtctg gcagccgccg acccactacc gcacctcgt cgacccggca     720
cggttcgtcg agcgcgtcga ggctttcgtc cgc                                 753
```

<210> SEQ ID NO 29
<211> LENGTH: 251
<212> TYPE: PRT
<213> ORGANISM: Artificial Sequence
<220> FEATURE:
<223> OTHER INFORMATION: Synthetic Lactonase (CL00025659)

<400> SEQUENCE: 29

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu His Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu

```
                165                 170                 175
Glu Asp Ser Pro Glu Glu Leu Ala Ala Leu Val Ser Arg Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 30
<211> LENGTH: 753
<212> TYPE: DNA
<213> ORGANISM: Artificial Sequence
<220> FEATURE:
<223> OTHER INFORMATION: Synthetic Lactonase (CL00025659)

<400> SEQUENCE: 30
atgatcctcg cccacgacgt gtcgggctcc ggcccgctgc tggtcctcct gcacggcatc        60
accgaagacc gccgcagctg ggatccggtc gatttcaccg acggcttcac ggtcgtgcgg       120
gtcgacctgc gcgggcacgg ggcatcagcc gccgaagaac cgtacgacat ccccacgctc       180
gcgaccgacg tgcacgacac cctcgcgcag ctcgccgaga cgacgtgat  ccccggggaa       240 ctgccggtga tcgtcggcca ctcgatgggc gggatcgtcg cgacggcgta cggcgcgctc       300
ttccccgcgc gggcgatcgt caacgtggac cagcctctcc acctcgcggg catgcagggc       360
caggtgcagc aggcggaggg gatgctccgc ggggcggact cccgctgtt  catccacggc       420 atgttcgcgc agatggcggg cggcctggat gccgaggagc tggcgcgggt gaatggcatc       480
cggtctccga gcaggacgt  cgtcctcggg atgtggcggc gcttctcga  ggactcaccc       540 gaagaactgg cggcgctcgt gagccgcctg acgaggatcc cggaggacgt cccgtacctc       600
gtgatcacgg gtctcgatgc cgggccagag tacgcggcgt ggctgcagcg ggagatcccg       660
caggccgtcc aggaggtctg gcagccgccg acccactacc cgcacctcgt cgacccggca       720
cggttcgtcg agcgcgtcga ggctttcgtc cgc                                    753

<210> SEQ ID NO 31
<211> LENGTH: 251
<212> TYPE: PRT
<213> ORGANISM: Artificial Sequence
<220> FEATURE:
<223> OTHER INFORMATION: Artificial Lactonase (CL00025666)

<400> SEQUENCE: 31

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Glu
65                  70                  75                  80

Leu Pro Ile Ile Val Gly His Ser Met Gly Gly Ile Val Ala Thr Ala
```

```
                    85                  90                  95
Tyr Gly Ala Leu Phe Pro Ala Arg Ala Ile Val Asn Val Asp Gln Pro
                100                 105                 110

Leu Gln Leu Ala Gly Met Gln Gly Gln Val Gln Gln Ala Glu Gly Met
            115                 120                 125

Leu Arg Gly Ala Asp Phe Pro Leu Phe Ile His Gly Met Phe Ala Gln
        130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 32
<211> LENGTH: 753
<212> TYPE: DNA
<213> ORGANISM: Artificial Sequence
<220> FEATURE:
<223> OTHER INFORMATION: Synthetic Lactonase (CL00025666)

<400> SEQUENCE: 32

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga cgacgtgat ccccggggaa      240
ctgccgatca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 33
<211> LENGTH: 251
<212> TYPE: PRT
<213> ORGANISM: Artificial Sequence
<220> FEATURE:
<223> OTHER INFORMATION: Synthetic Lactonase (CL00025686 G2P)

<400> SEQUENCE: 33

Met Ile Leu Ala His Asp Val Ser Gly Ser Gly Pro Leu Leu Val Leu

```
  1               5                  10                 15
Leu His Gly Ile Thr Glu Asp Arg Arg Ser Trp Asp Pro Val Asp Phe
          20                 25                 30
Thr Asp Gly Phe Thr Val Val Arg Val Asp Leu Arg Gly His Gly Ala
          35                 40                 45
Ser Ala Ala Glu Glu Pro Tyr Asp Ile Pro Thr Leu Ala Thr Asp Val
     50                 55                 60
His Glu Thr Leu Ala Gln Leu Ala Glu Asn Asp Val Ile Pro Gly Gly
 65                 70                 75                 80
Leu Pro Ile Ile Val Gly His Ser Met Gly Gly Ile Val Ala Thr Ala
                85                 90                 95
Tyr Gly Ala Leu Phe Pro Ala Arg Ala Ile Val Asn Val Asp Gln Pro
               100                105                110
Leu Gln Leu Ala Gly Met Gln Gly Gln Val Gln Ala Glu Gly Met
           115                120                125
Leu Arg Gly Ala Asp Phe Pro Val Phe Ile His Gly Met Phe Ala Gln
           130                135                140
Met Ala Gly Gly Leu Asp Ala Glu Glu Leu Ala Arg Val Asn Gly Ile
145                150                155                160
Arg Ser Pro Arg Gln Asp Val Val Leu Gly Met Trp Arg Pro Leu Leu
               165                170                175
Glu Asp Ser Pro Glu Glu Leu Ala Ala Leu Val Ser Gly Leu Thr Arg
           180                185                190
Ile Pro Glu Asp Val Pro Tyr Leu Val Ile Thr Gly Leu Asp Ala Gly
           195                200                205
Pro Glu Tyr Ala Ala Trp Leu Gln Arg Glu Ile Pro Gln Ala Val Gln
       210                215                220
Glu Val Trp Gln Pro Pro Thr His Tyr Pro His Leu Val Asp Pro Ala
225                230                235                240
Arg Phe Val Glu Arg Val Glu Ala Phe Val Arg
               245                250
```

<210> SEQ ID NO 34
<211> LENGTH: 753
<212> TYPE: DNA
<213> ORGANISM: Artificial Sequence
<220> FEATURE:
<223> OTHER INFORMATION: Synthetic Lactonase (CL00025686 G2P)

<400> SEQUENCE: 34

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga acgacgtgat ccccgggggc     240
ctgccgatca tcgtcggcca ctcgatgggc ggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccggtcttc atccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
```

```
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 35
<211> LENGTH: 251
<212> TYPE: PRT
<213> ORGANISM: Artificial Sequence
<220> FEATURE:
<223> OTHER INFORMATION: Synthetic Lactonase (CL00025687)

<400> SEQUENCE: 35

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Ser Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Glu Thr Leu Ala Gln Leu Ala Glu Asn Asp Val Ile Pro Gly Glu
65                  70                  75                  80

Leu Pro Ile Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Thr Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 36
<211> LENGTH: 753
<212> TYPE: DNA
<213> ORGANISM: Artificial Sequence
<220> FEATURE:
<223> OTHER INFORMATION: Synthetic Lactonase (CL00025687)

<400> SEQUENCE: 36

```
atgatcctcg cccacgacgt gtcgggctcc ggcccgctgc tggtcctcct gcacggcatc    60
accgaagacc gccgcagctg ggatccggtc gatttcaccg actccttcac ggtcgtgcgg   120
gtcgacctgc gcgggcacgg ggcatcagcc gccgaagaac cgtacgacat ccccacgctc   180
gcgaccgacg tgcacgagac cctcgcgcag ctcgccgaga acgacgtgat ccccggggaa   240
```

-continued

```
ctgccgatca tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact tcccgctgtt catccacggc    420
atgttcgcgc agatgcgggc ggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
cagaccgtcc aggaggtctg gcagccgccg acccactacc cgcacctcgt cgacccggca    720
cggttcgtcg agcgcgtcga ggctttcgtc cgc                                  753
```

<210> SEQ ID NO 37
<211> LENGTH: 251
<212> TYPE: PRT
<213> ORGANISM: Artificial Sequence
<220> FEATURE:
<223> OTHER INFORMATION: Synthetic Lactonase (CL00025689)

<400> SEQUENCE: 37

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Val Pro Gly Gly
65                  70                  75                  80

Leu Pro Ile Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu His Leu Ala Gly Met Gln Gly Gln Val Gln Gln Ala Glu Gly Met
        115                 120                 125

Leu Arg Gly Glu Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Arg Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 38

<211> LENGTH: 753
<212> TYPE: DNA
<213> ORGANISM: Artificial Sequence
<220> FEATURE:
<223> OTHER INFORMATION: Synthetic Lactonase (CL00025689)

<400> SEQUENCE: 38

```
atgatcctcg cccacgacgt gtcgggctcc ggcccgctgc tggtcctcct gcacggcatc      60
accgaagacc gccgcagctg ggatccggtc gatttcaccg acggcttcac ggtcgtacgg     120
gtcgacctgc gcgggcacgg ggcatcagcc gccgaagaac cgtacgacat ccccacgctc     180
gcgaccgacg tgcacgagac cctcgcgcag ctcgccgaga cgacgtggt ccccggggc      240
ctgccgatca tcgtcggcca ctcgatgggc gggatcgtcg cgacggcgta cggcgcgctc     300
ttccccgcgc gggcgatcgt caacgtggac cagcctctcc acctcgcggg catgcagggc     360
caggtgcagc aggcggaggg gatgctccgc ggggaggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagccgcctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc gcacctcgt cgacccggca     720
cggttcgtcg agcgcgtcga ggctttcgtc cgc                                  753
```

<210> SEQ ID NO 39
<211> LENGTH: 251
<212> TYPE: PRT
<213> ORGANISM: Artificial Sequence
<220> FEATURE:
<223> OTHER INFORMATION: Synthetic Lactonase (CL00025717)

<400> SEQUENCE: 39

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Ser Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190
```

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 40
<211> LENGTH: 753
<212> TYPE: DNA
<213> ORGANISM: Artificial Sequence
<220> FEATURE:
<223> OTHER INFORMATION: Synthetic Lactonase (CL00025717)

<400> SEQUENCE: 40

| | | |
|---|---|---|
| atgatcctcg cccacgacgt gtcgggctcc ggcccgctgc tggtcctcct gcacggcatc | 60 |
| accgaagacc gccgcagctg ggatccggtc gatttcaccg acggcttcac ggtcgtgcgg | 120 |
| gtcgacctgc gcgggcacgg ggcatcagcc gccgaagaac cgtacgacat ccccacgctc | 180 |
| gcgaccgacg tgcacgacac cctcgcgcag ctcgccgaga acgacgtgat ccccggggaa | 240 |
| ctgccggtga tcgtcggcca ctcgatgggc gggatcgtcg cgacggcgta cggcgcgctc | 300 |
| ttccccgcgc gggcgatcgt caacgtggac cagcctctcc agctcgcggg catgcagtct | 360 |
| caggtgcagc aggcggaggg gatgctccgc ggggcggact cccgctgttt catccacggc | 420 |
| atgttcgcgc agatggcggg cggcctggat gccgaggagc tggcgcgggt gaatggcatc | 480 |
| cggtctccga ggcaggacgt cgtcctcggg atgtggcggc cgcttctcga ggactcaccc | 540 |
| gaagaactgg cggcgctcgt gagcggtctg acgaggatcc cggaggacgt cccgtacctc | 600 |
| gtgatcacgg gtctcgatgc cgggccagag tacgcggcgt ggctgcagcg ggagatcccg | 660 |
| caggccgtcc aggaggtctg gcagccgccg acccactacc cgcacctcgt cgacccggca | 720 |
| cggttcgtcg agcgcgtcga ggctttcgtc cgc | 753 |

<210> SEQ ID NO 41
<211> LENGTH: 251
<212> TYPE: PRT
<213> ORGANISM: Artificial Sequence
<220> FEATURE:
<223> OTHER INFORMATION: Synthetic Lactonase (CL00025721)

<400> SEQUENCE: 41

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Asp Thr Leu Ile Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
                100                 105                 110

Leu Gln Leu Ala Gly Met Gln Gly Gln Val Gln Ala Glu Gly Met
         115                 120                 125

Leu Arg Gly Ala Asp Phe Pro Leu Phe Ile His Gly Met Phe Ala Gln
     130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 42
<211> LENGTH: 753
<212> TYPE: DNA
<213> ORGANISM: Artificial Sequence
<220> FEATURE:
<223> OTHER INFORMATION: Synthetic Lactonase (CL00025721)

<400> SEQUENCE: 42
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcattcag ctcgccgaga cgacgtgat ccccggggaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753

<210> SEQ ID NO 43
<211> LENGTH: 251
<212> TYPE: PRT
<213> ORGANISM: Artificial Sequence
<220> FEATURE:
<223> OTHER INFORMATION: Synthetic Lactonase (CL00025728)

<400> SEQUENCE: 43

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

```
Thr Asp Gly Phe Thr Val Val Arg Val Asp Leu Arg Gly His Gly Ala
        35                  40                  45
Ser Ala Ala Glu Glu Pro Tyr Asp Ile Pro Thr Leu Ala Thr Asp Val
 50                  55                  60
His Asp Thr Leu Val Gln Leu Ala Glu Asn Asp Val Ile Pro Gly Glu
 65                  70                  75                  80
Leu Pro Val Ile Val Gly His Ser Met Gly Gly Ile Val Ala Thr Ala
                 85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Ala Glu Gly Met
        115                 120                 125
Leu Arg Gly Ala Asp Phe Pro Leu Phe Ile His Gly Met Phe Ala Gln
130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Gly Leu Thr Arg
            180                 185                 190
Ile Pro Glu Asp Val Pro Tyr Leu Val Ile Thr Gly Leu Asp Ala Gly
        195                 200                 205
Pro Glu Tyr Ala Ala Trp Leu Gln Arg Glu Ile Pro Gln Ala Val Gln
    210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250

<210> SEQ ID NO 44
<211> LENGTH: 753
<212> TYPE: DNA
<213> ORGANISM: Artificial Sequence
<220> FEATURE:
<223> OTHER INFORMATION: Synthetic Lactonase (CL00025728)

<400> SEQUENCE: 44
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg gcatcagcc gccgaagaac cgtacgacat ccccacgctc     180
gcgaccgacg tgcacgacac cctcgttcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggtctccga gcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                    753
```

<210> SEQ ID NO 45
<211> LENGTH: 251
<212> TYPE: PRT
<213> ORGANISM: Artificial Sequence
<220> FEATURE:
<223> OTHER INFORMATION: Synthetic Lactonase (CL00025748)

<400> SEQUENCE: 45

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Glu Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 46
<211> LENGTH: 753
<212> TYPE: DNA
<213> ORGANISM: Artificial Sequence
<220> FEATURE:
<223> OTHER INFORMATION: Synthetic Lactonase (CL00025748)

<400> SEQUENCE: 46
atgatcctcg cccacgacgt gtcgggctcc ggcccgctgc tggtcctcct gcacggcatc      60
accgaagacc gccgcagctg ggatccggtc gatttcaccg agggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360

```
caggtgcagc aggcggaggg gatgctccgc ggggcggact tcccgctgtt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg tctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 47
<211> LENGTH: 251
<212> TYPE: PRT
<213> ORGANISM: Artificial Sequence
<220> FEATURE:
<223> OTHER INFORMATION: Synthetic Lactonase (CL00025754)

<400> SEQUENCE: 47

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu His Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 48
<211> LENGTH: 753
<212> TYPE: DNA
<213> ORGANISM: Artificial Sequence
<220> FEATURE:

<223> OTHER INFORMATION: Synthetic Lactonase (CL00025754)

<400> SEQUENCE: 48

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgagc atgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc      420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc gcacctcgt cgacccggca      720
cggttcgtcg agcgcgtcga ggctttcgtc cgc                                  753
```

<210> SEQ ID NO 49
<211> LENGTH: 251
<212> TYPE: PRT
<213> ORGANISM: Artificial Sequence
<220> FEATURE:
<223> OTHER INFORMATION: Synthetic Lactonase (CL00025762)

<400> SEQUENCE: 49

```
Met Ile Leu Ala His Asp Val Ser Gly Ser Gly Pro Leu Leu Val Leu
  1               5                  10                  15

Leu His Gly Ile Thr Glu Asp Arg Arg Ser Trp Asp Pro Val Asp Phe
             20                  25                  30

Thr Asp Gly Phe Thr Val Val Arg Val Asp Leu Arg Gly His Gly Ala
         35                  40                  45

Ser Ala Ala Glu Glu Pro Tyr Asp Ile Pro Thr Leu Ala Thr Asp Val
     50                  55                  60

His Asp Thr Leu Ala Gln Leu Ala Glu Asn Asp Val Ile Pro Gly Glu
 65                  70                  75                  80

Leu Pro Val Ile Val Gly His Ser Met Gly Gly Ile Val Ala Thr Ala
                 85                  90                  95

Tyr Gly Ala Leu Phe Pro Ala Arg Ala Ile Val Asn Val Asp Gln Pro
            100                 105                 110

Leu Gln Leu Ala Gly Met Gln Thr Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205
```

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 50
<211> LENGTH: 753
<212> TYPE: DNA
<213> ORGANISM: Artificial Sequence
<220> FEATURE:
<223> OTHER INFORMATION: Synthetic Lactonase (CL00025762)

<400> SEQUENCE: 50

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg gcatcagcc gccgaagaac cgtacgacat ccccacgctc     180
gcgaccgacg tgcacgacac cctcgcgcag ctcgccgaga cgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagact     360
caggtgcagc aggcggaggg gatgctccgc ggggcggact cccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                 753
```

<210> SEQ ID NO 51
<211> LENGTH: 251
<212> TYPE: PRT
<213> ORGANISM: Artificial Sequence
<220> FEATURE:
<223> OTHER INFORMATION: Synthetic Lactonase (CL00025791)

<400> SEQUENCE: 51

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln His Gln Val Gln Ala Glu Gly Met
            115                 120                 125

Leu Arg Gly Ala Asp Phe Pro Leu Phe Ile His Gly Met Phe Ala Gln
            130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
                195                 200                 205

Pro Glu Tyr Ala Ala Trp Leu Gln Arg Glu Ile Pro Gln Ala Val Gln
            210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 52
<211> LENGTH: 753
<212> TYPE: DNA
<213> ORGANISM: Artificial Sequence
<220> FEATURE:
<223> OTHER INFORMATION: Synthetic Lactonase (CL00025791)

<400> SEQUENCE: 52
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240 ctgccggtga tcgtcggcca ctcgatgggc gggatcgtcg cgacggcgta cggcgcgctc     300
ttccccgcgc gggcgatcgt caacgtggac cagcctctcc agctcgcggg catgcagcat     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753

<210> SEQ ID NO 53
<211> LENGTH: 251
<212> TYPE: PRT
<213> ORGANISM: Artificial Sequence
<220> FEATURE:
<223> OTHER INFORMATION: Synthetic Lactonase (CL00025924)

<400> SEQUENCE: 53

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
            35                  40                  45

```
Ser Ala Ala Glu Glu Pro Tyr Asp Ile Pro Thr Leu Ala Thr Asp Val
 50                  55                  60
His Asp Thr Leu Cys Gln Leu Ala Glu Asn Asp Val Ile Pro Gly Glu
 65                      70                  75                  80
Leu Pro Val Ile Val Gly His Ser Met Gly Gly Ile Val Ala Thr Ala
                     85                  90                  95
Tyr Gly Ala Leu Phe Pro Ala Arg Ala Ile Val Asn Val Asp Gln Pro
                100                 105                 110
Leu Gln Leu Ala Gly Met Gln Gly Gln Val Gln Ala Glu Gly Met
             115                 120                 125
Leu Arg Gly Ala Asp Phe Pro Leu Phe Ile His Gly Met Phe Ala Gln
         130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Gly Leu Thr Arg
            180                 185                 190
Ile Pro Glu Asp Val Pro Tyr Leu Val Ile Thr Gly Leu Asp Ala Gly
        195                 200                 205
Pro Glu Tyr Ala Ala Trp Leu Gln Arg Glu Ile Pro Gln Ala Val Gln
    210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250

<210> SEQ ID NO 54
<211> LENGTH: 753
<212> TYPE: DNA
<213> ORGANISM: Artificial Sequence
<220> FEATURE:
<223> OTHER INFORMATION: Synthetic Lactonase (CL00025924)

<400> SEQUENCE: 54
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctctgtcag ctcgccgaga cgacgtgat ccccggggaa      240 ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagg aggcggaggg gatgctccgc ggggcggact cccgctgttt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgaccggca    720 cggttcgtcg agcgcgtcga ggctttcgtc cgc                                 753

<210> SEQ ID NO 55
<211> LENGTH: 251
<212> TYPE: PRT
```

<213> ORGANISM: Artificial Sequence
<220> FEATURE:
<223> OTHER INFORMATION: Synthetic Lactonase (CL00025935)

<400> SEQUENCE: 55

```
Met Ile Leu Ala His Asp Val Ser Gly Ser Gly Pro Leu Leu Val Leu
1               5                   10                  15
Leu His Gly Ile Thr Glu Asp Arg Arg Ser Trp Asp Pro Val Asp Phe
            20                  25                  30
Thr Ala Gly Phe Thr Val Val Arg Val Asp Leu Arg Gly His Gly Ala
        35                  40                  45
Ser Ala Ala Glu Glu Pro Tyr Asp Ile Pro Thr Leu Ala Thr Asp Val
    50                  55                  60
His Asp Thr Leu Ala Gln Leu Ala Glu Asn Asp Val Ile Pro Gly Glu
65                  70                  75                  80
Leu Pro Val Ile Val Gly His Ser Met Gly Gly Ile Val Ala Thr Ala
                85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Gln Ala Glu Gly Met
        115                 120                 125
Leu Arg Gly Ala Asp Phe Pro Leu Phe Ile His Gly Met Phe Ala Gln
    130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Gly Leu Thr Arg
            180                 185                 190
Ile Pro Glu Asp Val Pro Tyr Leu Val Ile Thr Gly Leu Asp Ala Gly
        195                 200                 205
Pro Glu Tyr Ala Ala Trp Leu Gln Arg Glu Ile Pro Gln Ala Val Gln
    210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250
```

<210> SEQ ID NO 56
<211> LENGTH: 753
<212> TYPE: DNA
<213> ORGANISM: Artificial Sequence
<220> FEATURE:
<223> OTHER INFORMATION: Synthetic Lactonase (CL00025935)

<400> SEQUENCE: 56

```
atgatcctcg cccacgacgt gtcgggctcc ggcccgctgc tggtcctcct gcacggcatc     60
accgaagacc gccgcagctg ggatccggtc gatttcaccg cgggcttcac ggtcgtgcgg    120
gtcgacctgc gcgggcacgg ggcatcagcc gccgaagaac cgtacgacat ccccacgctc    180
gcgaccgacg tgcacgacac cctcgcgcag ctcgccgaga acgacgtgat ccccggggaa    240
ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcaga aggcggaggg gatgctccgc ggggcggact cccgctgttt catccacggc    420
atgttcgcgc agatggcggg cggcctggat gccgaggagc tggcgcgggt gaatggcatc    480
```

```
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg tctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 57
<211> LENGTH: 251
<212> TYPE: PRT
<213> ORGANISM: Artificial Sequence
<220> FEATURE:
<223> OTHER INFORMATION: Synthetic Lactonase (CL00025955)

<400> SEQUENCE: 57

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Ala Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 58
<211> LENGTH: 753
<212> TYPE: DNA
<213> ORGANISM: Artificial Sequence
<220> FEATURE:
<223> OTHER INFORMATION: Synthetic Lactonase (CL00025955)

<400> SEQUENCE: 58

```
atgatcctcg cccacgacgt gtcgggctcc ggcccgctgc tggtcctcct gcacggcatc    60
accgaagacc gccgcagctg ggatccggtc gatttcaccg acggcttcac ggtcgtgcgg   120
gtcgacctgc gcgggcacgg ggcatcagcc gccgaagaac cgtacgacat ccccacgctc   180
gcgaccgacg tgcacgacac cctcgcgcag ctcgccgaga cgacgtgat ccccggggaa    240
ctgccggtga tcgtcggcca ctcgatgggc gggatcgtcg cgacggcgta cggcgcgctc   300
ttccccgcgc gggcgatcgt caacgtggac cagcctctcc agctcgcggg catgcagggc   360
caggtgcagc aggcggaggc gatgctccgc ggggcggact cccgctgttt catccacggc   420
atgttcgcgc agatggcggg cggcctggat gccgaggagc tggcgcgggt gaatggcatc   480
cggtctccga ggcaggacgt cgtcctcggg atgtggcggc cgcttctcga ggactcaccc   540
gaagaactgg cggcgctcgt gagcggtctg acgaggatcc cggaggacgt cccgtacctc   600
gtgatcacgg gtctcgatgc cgggccagag tacgcggcgt ggctgcagcg ggagatcccg   660
caggccgtcc aggaggtctg gcagccgccg acccactacc cgcacctcgt cgacccggca   720
cggttcgtcg agcgcgtcga ggctttcgtc cgc                               753
```

<210> SEQ ID NO 59
<211> LENGTH: 251
<212> TYPE: PRT
<213> ORGANISM: Artificial Sequence
<220> FEATURE:
<223> OTHER INFORMATION: Synthetic Lactonase (CL00025958)

<400> SEQUENCE: 59

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Lys Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
```

```
                    225                 230                 235                 240
Arg Phe Val Glu Arg Val Glu Ala Phe Val Arg
                245                 250

<210> SEQ ID NO 60
<211> LENGTH: 753
<212> TYPE: DNA
<213> ORGANISM: Artificial Sequence
<220> FEATURE:
<223> OTHER INFORMATION: Synthetic Lactonase (CL00025958)

<400> SEQUENCE: 60
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg gcatcagcc gccgaagaac cgtacgacat ccccacgctc     180
gcgaccgacg tgcacgacac cctcaagcag ctcgccgaga cgacgtgat cccccggggaa     240 ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact ccccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg tctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                 753

<210> SEQ ID NO 61
<211> LENGTH: 251
<212> TYPE: PRT
<213> ORGANISM: Artificial Sequence
<220> FEATURE:
<223> OTHER INFORMATION: Synthetic Lactonase (CL00025961)

<400> SEQUENCE: 61

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Asp Thr Leu Gln Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
        130                 135                 140

Met Ala Gly Gly Leu Asp Ala Glu Glu Leu Ala Arg Val Asn Gly Ile
```

```
145                 150                 155                 160
Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 62
<211> LENGTH: 753
<212> TYPE: DNA
<213> ORGANISM: Artificial Sequence
<220> FEATURE:
<223> OTHER INFORMATION: Synthetic Lactonase (CL00025961)

<400> SEQUENCE: 62
atgatcctcg cccacgacgt gtcgggctcc ggcccgctgc tggtcctcct gcacggcatc     60
accgaagacc gccgcagctg ggatccggtc gatttcaccg acggcttcac ggtcgtgcgg    120
gtcgacctgc gcgggcacgg ggcatcagcc gccgaagaac cgtacgacat ccccacgctc    180
gcgaccgacg tgcacgacac cctccagcag ctcgccgaga cgacgtgat ccccggggaa     240 ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact cccgctgtt catccacggc      420 atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753

<210> SEQ ID NO 63
<211> LENGTH: 251
<212> TYPE: PRT
<213> ORGANISM: Artificial Sequence
<220> FEATURE:
<223> OTHER INFORMATION: Synthetic Lactonase (CL00025963)

<400> SEQUENCE: 63

Met Ile Leu Ala His Asp Val Ser Gly Ser Gly Pro Leu Leu Val Leu
1               5                  10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
```

```
                65                   70                  75                  80
Leu Pro Val Ile Val Gly His Ser Met Gly Gly Ile Val Ala Thr Ala
                    85                  90                  95

Tyr Gly Ala Leu Phe Pro Ala Arg Ala Ile Val Asn Val Asp Gln Pro
                100                 105                 110

Leu Gln Leu Ala Gly Met Gln Arg Gln Val Gln Ala Glu Gly Met
                115                 120                 125

Leu Arg Gly Ala Asp Phe Pro Leu Phe Ile His Gly Met Phe Ala Gln
        130                 135                 140

Met Ala Gly Gly Leu Asp Ala Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
                180                 185                 190

Ile Pro Glu Asp Val Pro Tyr Leu Val Ile Thr Gly Leu Asp Ala Gly
                195                 200                 205

Pro Glu Tyr Ala Ala Trp Leu Gln Arg Glu Ile Pro Gln Ala Val Gln
        210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 64
<211> LENGTH: 753
<212> TYPE: DNA
<213> ORGANISM: Artificial Sequence
<220> FEATURE:
<223> OTHER INFORMATION: Synthetic Lactonase (CL00025963)

<400> SEQUENCE: 64

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg    120
gtcgacctgc gcgggcacgg ggcatcagcc gccgaagaac cgtacgacat ccccacgctc    180
gcgaccgacg tgcacgacac cctcgcgcag ctcgccgaga cgacgtgat ccccggggaa    240
ctgccggtga tcgtcggcca ctcgatgggc gggatcgtcg cgacggcgta cggcgcgctc    300
ttccccgcgc gggcgatcgt caacgtggac cagcctctcc agctcgcggg catgcagcgt    360
caggtgcagg aggcggaggg gatgctccgc ggggcggact cccgctgtt catccacggc    420
atgttcgcgc agatggcggg cggcctggat gccgaggagc tggcgcgggt gaatggcatc    480
cggtctccga gcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                  753
```

<210> SEQ ID NO 65
<211> LENGTH: 251
<212> TYPE: PRT
<213> ORGANISM: Artificial Sequence
<220> FEATURE:
<223> OTHER INFORMATION: Synthetic Lactonase (CL00025984)

<400> SEQUENCE: 65

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Gly Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 66
<211> LENGTH: 753
<212> TYPE: DNA
<213> ORGANISM: Artificial Sequence
<220> FEATURE:
<223> OTHER INFORMATION: Synthetic Lactonase (CL00025984)

<400> SEQUENCE: 66
atgatcctcg cccacgacgt gtcgggctcc ggcccgctgc tggtcctcct gcacggcatc      60
accgaagacc gccgcagctg ggatccggtc gatttcaccg ggggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600

```
gtgatcacgg gtctcgatgc cgggccagag tacgcggcgt ggctgcagcg ggagatcccg      660
caggccgtcc aggaggtctg gcagccgccg acccactacc cgcacctcgt cgacccggca      720
cggttcgtcg agcgcgtcga ggctttcgtc cgc                                   753
```

<210> SEQ ID NO 67
<211> LENGTH: 251
<212> TYPE: PRT
<213> ORGANISM: Artificial Sequence
<220> FEATURE:
<223> OTHER INFORMATION: Synthetic Lactonase (CL00026017)

<400> SEQUENCE: 67

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Thr Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 68
<211> LENGTH: 753
<212> TYPE: DNA
<213> ORGANISM: Artificial Sequence
<220> FEATURE:
<223> OTHER INFORMATION: Synthetic Lactonase (CL00026017)

<400> SEQUENCE: 68

```
atgatcctcg cccacgacgt gtcgggctcc ggcccgctgc tggtcctcct gcacggcatc       60
accgaagacc gccgcagctg ggatccggtc gatttcaccg acggcttcac ggtcgtgcgg      120
```

```
gtcgacctgc gcgggcacgg ggcatcagcc gccgaagaac cgtacgacat ccccacgctc    180
gcgaccgacg tgcacgacac cctcgcgcag ctcgccgaga acgacgtgat ccccggggaa    240
ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact cccgctgttt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg gacgatcccg    660
caggccgtcc aggaggtctg gcagccgccg acccactacc cgcacctcgt cgacccggca    720
cggttcgtcg agcgcgtcga ggctttcgtc cgc    753
```

<210> SEQ ID NO 69
<211> LENGTH: 251
<212> TYPE: PRT
<213> ORGANISM: Artificial Sequence
<220> FEATURE:
<223> OTHER INFORMATION: Synthetic Lactonase (CL00026020)

<400> SEQUENCE: 69

```
Met Ile Leu Ala His Asp Val Ser Gly Ser Gly Pro Leu Leu Val Leu
 1               5                  10                  15

Leu His Gly Ile Thr Glu Asp Arg Arg Ser Trp Asp Pro Val Asp Phe
             20                  25                  30

Thr Asp Gly Phe Thr Val Val Arg Val Asp Leu Arg Gly His Gly Ala
         35                  40                  45

Ser Ala Ala Glu Glu Pro Tyr Asp Ile Pro Thr Leu Ala Thr Asp Val
     50                  55                  60

His Asp Thr Leu Thr Gln Leu Ala Glu Asn Asp Val Ile Pro Gly Glu
 65                  70                  75                  80

Leu Pro Val Ile Val Gly His Ser Met Gly Gly Ile Val Ala Thr Ala
                 85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 70
<211> LENGTH: 753
<212> TYPE: DNA
<213> ORGANISM: Artificial Sequence
<220> FEATURE:
<223> OTHER INFORMATION: Synthetic Lactonase (CL00026020)

<400> SEQUENCE: 70

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcactcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg tctcgatgc cgggccagag tacgcggcgt ggctgcagcg ggagatcccg     660
caggccgtcc aggaggtctg gcagccgccg acccactacc gcacctcgt cgacccggca     720
cggttcgtcg agcgcgtcga ggctttcgtc cgc                                  753
```

<210> SEQ ID NO 71
<211> LENGTH: 251
<212> TYPE: PRT
<213> ORGANISM: Artificial Sequence
<220> FEATURE:
<223> OTHER INFORMATION: Synthetic Lactonase (CL00026041)

<400> SEQUENCE: 71

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Gln Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175
```

Glu Asp Ser Pro Glu Glu Leu Ala Ala Leu Val Ser Gly Leu Thr Arg
                180                 185                 190

Ile Pro Glu Asp Val Pro Tyr Leu Val Ile Thr Gly Leu Asp Ala Gly
            195                 200                 205

Pro Glu Tyr Ala Ala Trp Leu Gln Arg Glu Ile Pro Gln Ala Val Gln
210                 215                 220

Glu Val Trp Gln Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 72
<211> LENGTH: 753
<212> TYPE: DNA
<213> ORGANISM: Artificial Sequence
<220> FEATURE:
<223> OTHER INFORMATION: Synthetic Lactonase (CL00026041)

<400> SEQUENCE: 72

```
atgatcctcg cccacgacgt gtcgggctcc ggcccgctgc tggtcctcct gcacggcatc      60
accgaagacc gccgcagctg ggatccggtc gatttcaccc agggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 73
<211> LENGTH: 251
<212> TYPE: PRT
<213> ORGANISM: Artificial Sequence
<220> FEATURE:
<223> OTHER INFORMATION: Synthetic Lactonase (CL00026052)

<400> SEQUENCE: 73

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
                100                 105                 110

Leu Gln Leu Ala Gly Met Gln Pro Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 74
<211> LENGTH: 753
<212> TYPE: DNA
<213> ORGANISM: Artificial Sequence
<220> FEATURE:
<223> OTHER INFORMATION: Synthetic Lactonase (CL00026052)

<400> SEQUENCE: 74

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg gcatcagcc gccgaagaac cgtacgacat ccccacgctc     180
gcgaccgacg tgcacgacac cctcgcgcag ctcgccgaga cgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagccg     360
caggtgcagc aggcggaggg gatgctccgc ggggcggact cccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 75
<211> LENGTH: 251
<212> TYPE: PRT
<213> ORGANISM: Artificial Sequence
<220> FEATURE:
<223> OTHER INFORMATION: Synthetic Lactonase (CL00026054)

<400> SEQUENCE: 75

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Glu Glu Pro Tyr Asp Ile Pro Thr Leu Ala Thr Asp Val
 50                  55                  60

His Asp Thr Leu Ala Gln Leu Ala Glu Asn Asp Val Ile Pro Gly Glu
 65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
 130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Asn Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
 210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 76
<211> LENGTH: 753
<212> TYPE: DNA
<213> ORGANISM: Artificial Sequence
<220> FEATURE:
<223> OTHER INFORMATION: Synthetic Lactonase (CL00026054)

<400> SEQUENCE: 76
atgatcctcg cccacgacgt gtcgggctcc ggcccgctgc tggtcctcct gcacggcatc        60
accgaagacc gccgcagctg ggatccggtc gatttcaccg acggcttcac ggtcgtgcgg       120
gtcgacctgc gcgggcacgg ggcatcagcc gccgaagaac cgtacgacat ccccacgctc       180
gcgaccgacg tgcacgacac cctcgcgcag ctcgccgaga acgacgtgat ccccggggaa       240
ctgccggtga tcgtcggcca ctcgatgggc gggatcgtcg cgacggcgta cggcgcgctc       300
ttccccgcgc gggcgatcgt caacgtggac cagcctctcc agctcgcggg catgcagggc       360
caggtgcagc aggcggaggg gatgctccgc ggggcggact tcccgctgtt catccacggc       420
atgttcgcgc agatggcggg cggcctggat gccgaggagc tggcgcgggt gaatggcatc       480
cggtctccga ggcaggacgt cgtcctcggg atgtggcggc cgcttctcga ggactcaccc       540
gaagaactga atgcgctcgt gagcggtctg acgaggatcc cggaggacgt cccgtacctc       600
gtgatcacgg gtctcgatgc cgggccagag tacgcggcgt ggctgcagcg ggagatcccg       660
caggccgtcc aggaggtctg gcagccgccg acccactacc cgcacctcgt cgacccggca       720
cggttcgtcg agcgcgtcga ggctttcgtc cgc        753

<210> SEQ ID NO 77
<211> LENGTH: 251
<212> TYPE: PRT
<213> ORGANISM: Artificial Sequence
<220> FEATURE:
<223> OTHER INFORMATION: Synthetic Lactonase (CL00026061)

<400> SEQUENCE: 77

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Ala Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 78
<211> LENGTH: 753
<212> TYPE: DNA
<213> ORGANISM: Artificial Sequence
<220> FEATURE:
<223> OTHER INFORMATION: Synthetic Lactonase (CL00026061)

<400> SEQUENCE: 78
atgatcctcg cccacgacgt gtcgggctcc ggcccgctgc tggtcctcct gcacggcatc        60
accgaagacc gccgcagctg ggatccggtc gatttcaccg acggcttcac ggtcgtgcgg       120
gtcgacctgc gcgggcacgg ggcatcagcc gccgaagaac cgtacgacat ccccacgctc       180
gcgaccgacg tgcacgacac cctcgcgcag ctcgccgaga cgacgtgat ccccggggaa        240

```
ctgccggtga tcgtcggcca ctcgatgggc gggatcgtcg cgacggcgta cggcgcgctc      300
ttccccgcgc gggcgatcgt caacgtggac cagcctctcc agctcgcggg catgcaggcg      360
caggtgcagc aggcggaggg gatgctccgc ggggcggact cccgctgtt catccacggc       420 atgttcgcgc agatggcggg cggcctggat gccgaggagc tggcgcgggt gaatggcatc      480
cggtctccga ggcaggacgt cgtcctcggg atgtggcggc cgcttctcga ggactcaccc      540
gaagaactgg cggcgctcgt gagcggtctg acgaggatcc cggaggacgt cccgtacctc      600
gtgatcacgg gtctcgatgc cgggccagag tacgcggcgt ggctgcagcg ggagatcccg      660
caggccgtcc aggaggtctg gcagccgccg acccactacc cgcacctcgt cgacccggca      720
cggttcgtcg agcgcgtcga ggctttcgtc cgc                                   753
```

<210> SEQ ID NO 79
<211> LENGTH: 251
<212> TYPE: PRT
<213> ORGANISM: Artificial Sequence
<220> FEATURE:
<223> OTHER INFORMATION: Synthetic Lactonase (CL00026088)

<400> SEQUENCE: 79

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Met Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 80
<211> LENGTH: 753

```
<212> TYPE: DNA
<213> ORGANISM: Artificial Sequence
<220> FEATURE:
<223> OTHER INFORMATION: Synthetic Lactonase (CL00026088)

<400> SEQUENCE: 80
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg tctcgatgc cgggccagag tacgcggcgt ggctgcagcg gatgatcccg     660
caggccgtcc aggaggtctg gcagccgccg acccactacc gcacctcgt cgacccggca     720
cggttcgtcg agcgcgtcga ggctttcgtc cgc                                  753

<210> SEQ ID NO 81
<211> LENGTH: 251
<212> TYPE: PRT
<213> ORGANISM: Artificial Sequence
<220> FEATURE:
<223> OTHER INFORMATION: Synthetic Lactonase (CL00026089)

<400> SEQUENCE: 81

Met Ile Leu Ala His Asp Val Ser Gly Ser Gly Pro Leu Leu Val Leu
1               5                   10                  15
Leu His Gly Ile Thr Glu Asp Arg Arg Ser Trp Asp Pro Val Asp Phe
            20                  25                  30
Thr Asp Gly Phe Thr Val Val Arg Val Asp Leu Arg Gly His Gly Ala
        35                  40                  45
Ser Ala Ala Glu Glu Pro Tyr Asp Ile Pro Thr Leu Ala Thr Asp Val
    50                  55                  60
His Asp Thr Leu Ala Gln Leu Ala Glu Asn Asp Val Ile Pro Gly Glu
65                  70                  75                  80
Leu Pro Val Ile Val Gly His Ser Met Gly Gly Ile Val Ala Thr Ala
                85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Ala Glu Gly Met
        115                 120                 125
Leu Arg Gly Ala Asp Phe Pro Leu Phe Ile His Gly Met Phe Ala Gln
    130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Leu Val Ser Gly Leu Thr Arg
            180                 185                 190
```

```
Ile Pro Glu Asp Val Pro Tyr Leu Val Ile Thr Gly Leu Asp Ala Gly
            195                 200                 205

Pro Glu Tyr Ala Ala Trp Leu Gln Arg Asn Ile Pro Gln Ala Val Gln
        210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 82
<211> LENGTH: 753
<212> TYPE: DNA
<213> ORGANISM: Artificial Sequence
<220> FEATURE:
<223> OTHER INFORMATION: Synthetic Lactonase (CL00026089)

<400> SEQUENCE: 82

```
atgatcctcg cccacgacgt gtcgggctcc ggcccgctgc tggtcctcct gcacggcatc     60
accgaagacc gccgcagctg ggatccggtc gatttcaccg acggcttcac ggtcgtgcgg    120
gtcgacctgc gcgggcacgg ggcatcagcc gccgaagaac cgtacgacat ccccacgctc    180
gcgaccgacg tgcacgacac cctcgcgcag ctcgccgaga acgacgtgat ccccggggaa    240
ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact cccgctgtt catccacggc     420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg gaatatcccg    660
caggccgtcc aggaggtctg gcagccgccg acccactacc cgcacctcgt cgacccggca    720
cggttcgtcg agcgcgtcga ggctttcgtc cgc                                  753
```

<210> SEQ ID NO 83
<211> LENGTH: 251
<212> TYPE: PRT
<213> ORGANISM: Artificial Sequence
<220> FEATURE:
<223> OTHER INFORMATION: Synthetic Lactonase (CL00026102)

<400> SEQUENCE: 83

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Lys Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110
```

```
Leu Gln Leu Ala Gly Met Gln Gly Gln Val Gln Ala Glu Gly Met
        115                 120                 125
Leu Arg Gly Ala Asp Phe Pro Leu Phe Ile His Gly Met Phe Ala Gln
    130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Leu Ala Ala Leu Val Ser Gly Leu Thr Arg
                180                 185                 190
Ile Pro Glu Asp Val Pro Tyr Leu Val Ile Thr Gly Leu Asp Ala Gly
            195                 200                 205
Pro Glu Tyr Ala Ala Trp Leu Gln Arg Glu Ile Pro Gln Ala Val Gln
        210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250
```

<210> SEQ ID NO 84
<211> LENGTH: 753
<212> TYPE: DNA
<213> ORGANISM: Artificial Sequence
<220> FEATURE:
<223> OTHER INFORMATION: Synthetic Lactonase (CL00026102)

<400> SEQUENCE: 84

```
atgatcctcg cccacgacgt gtcgggctcc ggcccgctgc tggtcctcct gcacggcatc      60
accgaagacc gccgcagctg ggatccggtc gatttcacca agggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 85
<211> LENGTH: 251
<212> TYPE: PRT
<213> ORGANISM: Artificial Sequence
<220> FEATURE:
<223> OTHER INFORMATION: Synthetic Lactonase (CL00026104)

<400> SEQUENCE: 85

```
Met Ile Leu Ala His Asp Val Ser Gly Ser Gly Pro Leu Leu Val Leu
1               5                   10                  15
Leu His Gly Ile Thr Glu Asp Arg Arg Ser Trp Asp Pro Val Asp Phe
            20                  25                  30
```

```
Thr Ser Gly Phe Thr Val Val Arg Val Asp Leu Arg His Gly Ala
        35                  40                  45
Ser Ala Glu Glu Pro Tyr Asp Ile Pro Thr Leu Ala Thr Asp Val
 50                  55                  60
His Asp Thr Leu Ala Gln Leu Ala Glu Asn Asp Val Ile Pro Gly Glu
 65                  70                  75                  80
Leu Pro Val Ile Val Gly His Ser Met Gly Gly Ile Val Ala Thr Ala
                     85                  90                  95
Tyr Gly Ala Leu Phe Pro Ala Arg Ala Ile Val Asn Val Asp Gln Pro
                100                 105                 110
Leu Gln Leu Ala Gly Met Gln Gly Gln Val Gln Gln Ala Glu Gly Met
            115                 120                 125
Leu Arg Gly Ala Asp Phe Pro Leu Phe Ile His Gly Met Phe Ala Gln
130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Gly Leu Thr Arg
                180                 185                 190
Ile Pro Glu Asp Val Pro Tyr Leu Val Ile Thr Gly Leu Asp Ala Gly
            195                 200                 205
Pro Glu Tyr Ala Ala Trp Leu Gln Arg Glu Ile Pro Gln Ala Val Gln
        210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250
```

<210> SEQ ID NO 86
<211> LENGTH: 753
<212> TYPE: DNA
<213> ORGANISM: Artificial Sequence
<220> FEATURE:
<223> OTHER INFORMATION: Synthetic Lactonase (CL00026104)

<400> SEQUENCE: 86

```
atgatcctcg cccacgacgt gtcgggctcc ggcccgctgc tggtcctcct gcacggcatc      60
accgaagacc gccgcagctg ggatccggtc gatttcacct ctggcttcac ggtcgtgcgg     120
gtcgacctgc gcgggcacgg gcatcagcc gccaagaac cgtacgacat ccccacgctc      180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

```
<210> SEQ ID NO 87
<211> LENGTH: 251
<212> TYPE: PRT
<213> ORGANISM: Artificial Sequence
<220> FEATURE:
<223> OTHER INFORMATION: Synthetic Lactonase (CL00026114)

<400> SEQUENCE: 87
```

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Ala Ile Pro Gln Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

```
<210> SEQ ID NO 88
<211> LENGTH: 753
<212> TYPE: DNA
<213> ORGANISM: Artificial Sequence
<220> FEATURE:
<223> OTHER INFORMATION: Synthetic Lactonase (CL00026114)

<400> SEQUENCE: 88
```

| | | | | | |
|---|---|---|---|---|---|
| atgatcctcg | cccacgacgt | gtcgggctcc | ggcccgctgc | tggtcctcct | gcacggcatc | 60 |
| accgaagacc | gccgcagctg | ggatccggtc | gatttcaccg | acggcttcac | ggtcgtgcgg | 120 |
| gtcgacctgc | gcgggcacgg | ggcatcagcc | gccgaagaac | cgtacgacat | ccccacgctc | 180 |
| gcgaccgacg | tgcacgacac | cctcgcgcag | ctcgccgaga | acgacgtgat | ccccggggaa | 240 |
| ctgccggtga | tcgtcggcca | ctcgatgggc | gggatcgtcg | cgacggcgta | cggcgcgctc | 300 |
| ttccccgcgc | gggcgatcgt | caacgtggac | cagcctctcc | agctcgcggg | catgcagggc | 360 |

```
caggtgcagc aggcggaggg gatgctccgc ggggcggact tcccgctgtt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggcgatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 89
<211> LENGTH: 251
<212> TYPE: PRT
<213> ORGANISM: Artificial Sequence
<220> FEATURE:
<223> OTHER INFORMATION: Synthetic Lactonase (CL00026241)

<400> SEQUENCE: 89

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Ser Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 90
<211> LENGTH: 753
<212> TYPE: DNA
<213> ORGANISM: Artificial Sequence
<220> FEATURE:
<223> OTHER INFORMATION: Synthetic Lactonase (CL00026241)

<400> SEQUENCE: 90

```
atgatcctcg cccacgacgt gtcgggctcc ggcccgctgc tggtcctcct gcacggcatc     60
accgaagacc gccgcagctg ggatccggtc gatttcaccg acggcttcac ggtcgtgcgg    120
gtcgacctgc gcgggcacgg ggcatcagcc gccgaagaac cgtacgacat ccccacgctc    180
gcgaccgacg tgcacgacac cctcgcgcag ctcgccgaga acgactctat ccccggggaa    240
ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact cccgctgtt catccacggc     420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc gcacctcgt cgacccggca     720
cggttcgtcg agcgcgtcga ggctttcgtc cgc                                 753
```

<210> SEQ ID NO 91
<211> LENGTH: 251
<212> TYPE: PRT
<213> ORGANISM: Artificial Sequence
<220> FEATURE:
<223> OTHER INFORMATION: Synthetic Lactonase (CL00026289)

<400> SEQUENCE: 91

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
```

```
                210             215              220
Glu Val Trp Gln Pro Pro Thr His Tyr Pro His Leu Val Asp Pro Ala
225                 230                 235                 240

Arg Phe Val His Arg Val Glu Ala Phe Val Arg
                245                 250

<210> SEQ ID NO 92
<211> LENGTH: 753
<212> TYPE: DNA
<213> ORGANISM: Artificial Sequence
<220> FEATURE:
<223> OTHER INFORMATION: Synthetic Lactonase (CL00026289)

<400> SEQUENCE: 92
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240 ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcc atcgcgtcga ggctttcgtc cgc                                  753

<210> SEQ ID NO 93
<211> LENGTH: 251
<212> TYPE: PRT
<213> ORGANISM: Artificial Sequence
<220> FEATURE:
<223> OTHER INFORMATION: Synthetic Lactonase (CL00026296)

<400> SEQUENCE: 93

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
```

```
      130                 135                 140
Met Ala Gly Gly Leu Asp Ala Glu Glu Leu Ala Arg Val Asn Gly Ile
145                 150                 155                 160

Arg Asn Pro Arg Gln Asp Val Val Leu Gly Met Trp Arg Pro Leu Leu
                165                 170                 175

Glu Asp Ser Pro Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
                195                 200                 205

Pro Glu Tyr Ala Ala Trp Leu Gln Arg Glu Ile Pro Gln Ala Val Gln
            210                 215                 220

Glu Val Trp Gln Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 94
<211> LENGTH: 753
<212> TYPE: DNA
<213> ORGANISM: Artificial Sequence
<220> FEATURE:
<223> OTHER INFORMATION: Synthetic Lactonase (CL00026296)

<400> SEQUENCE: 94

```
atgatcctcg cccacgacgt gtcgggctcc ggcccgctgc tggtcctcct gcacggcatc    60
accgaagacc gccgcagctg ggatccggtc gatttcaccg acggcttcac ggtcgtgcgg   120
gtcgacctgc gcgggcacgg ggcatcagcc gccgaagaac cgtacgacat ccccacgctc   180
gcgaccgacg tgcacgacac cctcgcgcag ctcgccgaga cgacgtgat ccccggggaa    240
ctgccggtga tcgtcggcca ctcgatgggc gggatcgtcg gacggcgta cggcgcgctc    300
ttccccgcgc gggcgatcgt caacgtggac cagcctctcc agctcgcggg catgcagggc   360
caggtgcagc aggcggaggg gatgctccgc ggggcggact tcccgctgtt catccacggc   420
atgttcgcgc agatggcggg cggcctggat gccgaggagc tggcgcgggt gaatggcatc   480
cggaatccga ggcaggacgt cgtcctcggg atgtggcggc cgcttctcga ggactcaccc   540
gaagaactgg cggcgctcgt gagcggtctg acgaggatcc cggaggacgt cccgtacctc   600
gtgatcacgg gtctcgatgc cgggccagag tacgcggcgt ggctgcagcg ggagatcccg   660
caggccgtcc aggaggtctg cagccgccg acccactacc cgcacctcgt cgacccggca   720
cggttcgtcg agcgcgtcga ggctttcgtc cgc                                 753
```

<210> SEQ ID NO 95
<211> LENGTH: 251
<212> TYPE: PRT
<213> ORGANISM: Artificial Sequence
<220> FEATURE:
<223> OTHER INFORMATION: Synthetic Lactonase (CL00026297)

<400> SEQUENCE: 95

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
```

```
                    50                  55                  60

His Asp Thr Leu Ala Gln Leu Ala Glu Asn Asp Val Ile Pro Gly Glu
 65                  70                  75                  80

Leu Pro Val Ile Val Gly His Ser Met Gly Gly Ile Val Ala Thr Ala
                     85                  90                  95

Tyr Gly Ala Leu Phe Pro Ala Arg Ala Ile Val Asn Val Asp Gln Pro
                100                 105                 110

Leu Gln Leu Ala Gly Met Gln Gly Gln Val Gln Ala Glu Gly Met
            115                 120                 125

Leu Arg Gly Ala Asp Phe Pro Leu Phe Ile His Gly Met Phe Ala Gln
            130                 135                 140

Met Ala Gly Gly Leu Asp Ala Glu Glu Leu Ala Arg Val Asn Gly Ile
145                 150                 155                 160

Arg Cys Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
                180                 185                 190

Ile Pro Glu Asp Val Pro Tyr Leu Val Ile Thr Gly Leu Asp Ala Gly
            195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 96
<211> LENGTH: 753
<212> TYPE: DNA
<213> ORGANISM: Artificial Sequence
<220> FEATURE:
<223> OTHER INFORMATION: Synthetic Lactonase (CL00026297)

<400> SEQUENCE: 96
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240 ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtgtccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753

<210> SEQ ID NO 97
<211> LENGTH: 251
<212> TYPE: PRT
<213> ORGANISM: Artificial Sequence
```

<220> FEATURE:
<223> OTHER INFORMATION: Synthetic Lactonase (CL00026308)

<400> SEQUENCE: 97

```
Met Ile Leu Ala His Asp Val Ser Gly Ser Gly Pro Leu Leu Val Leu
1               5                   10                  15
Leu His Gly Ile Thr Glu Asp Arg Arg Ser Trp Asp Pro Val Asp Phe
                20                  25                  30
Thr Asp Gly Phe Thr Val Val Arg Val Asp Leu Arg Gly His Gly Ala
            35                  40                  45
Ser Ala Ala Glu Glu Pro Tyr Asp Ile Pro Thr Leu Ala Thr Asp Val
    50                  55                  60
His Asp Thr Leu Ala Gln Leu Ala Glu Asn Asp Val Ile Pro Gly Glu
65                  70                  75                  80
Leu Pro Val Ile Val Gly His Ser Met Gly Gly Ile Val Ala Thr Ala
                85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Gln Ala Glu Gly Met
    115                 120                 125
Leu Arg Gly Ala Asp Phe Pro Leu Phe Ile His Gly Met Phe Ala Gln
130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Gly Leu Thr Arg
            180                 185                 190
Ile Pro Glu Asp Val Pro Tyr Leu Val Ile Thr Gly Leu Asp Ala Gly
    195                 200                 205
Pro Glu Tyr Ala Ala Trp Leu Gln Arg Glu Ile Pro Gln Ala Val Gln
210                 215                 220
Glu Val Trp Gln Pro Pro Thr His Tyr Pro His Leu Val Asp Pro Ala
225                 230                 235                 240
Arg Phe Val Cys Arg Val Glu Ala Phe Val Arg
                245                 250
```

<210> SEQ ID NO 98
<211> LENGTH: 753
<212> TYPE: DNA
<213> ORGANISM: Artificial Sequence
<220> FEATURE:
<223> OTHER INFORMATION: Synthetic Lactonase (CL00026308)

<400> SEQUENCE: 98

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
```

```
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtct gtcgcgtcga ggctttcgtc cgc                                 753
```

<210> SEQ ID NO 99
<211> LENGTH: 251
<212> TYPE: PRT
<213> ORGANISM: Artificial Sequence
<220> FEATURE:
<223> OTHER INFORMATION: Synthetic Lactonase (CL00026310)

<400> SEQUENCE: 99

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Asp Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 100
<211> LENGTH: 753
<212> TYPE: DNA
<213> ORGANISM: Artificial Sequence
<220> FEATURE:
<223> OTHER INFORMATION: Synthetic Lactonase (CL00026310)

<400> SEQUENCE: 100

```
atgatcctcg cccacgacgt gtcgggctcc ggcccgctgc tggtcctcct gcacggcatc     60
```

```
accgaagacc gccgcagctg ggatccggtc gatttcaccg acggcttcac ggtcgtgcgg    120
gtcgacctgc gcgggcacgg ggcatcagcc gccgaagaac cgtacgacat ccccacgctc    180
gcgaccgacg tgcacgacac cctcgcgcag ctcgccgaga cgacgtgat ccccggggaa     240 ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact cccgctgtt catccacggc     420 atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt ggatggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 101
<211> LENGTH: 251
<212> TYPE: PRT
<213> ORGANISM: Artificial Sequence
<220> FEATURE:
<223> OTHER INFORMATION: Synthetic Lactonase (CL00026313)

<400> SEQUENCE: 101

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Arg Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240
```

Arg Phe Val Glu Arg Val Glu Ala Phe Val Arg
            245                 250

<210> SEQ ID NO 102
<211> LENGTH: 753
<212> TYPE: DNA
<213> ORGANISM: Artificial Sequence
<220> FEATURE:
<223> OTHER INFORMATION: Synthetic Lactonase (CL00026313)

<400> SEQUENCE: 102

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc      420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gaggggtctg acgaggatcc ggaggacgt cccgtacctc      600
gtgatcacgg tctcgatgc cgggccagag tacgcggcgt ggctgcagcg ggagatcccg      660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 103
<211> LENGTH: 251
<212> TYPE: PRT
<213> ORGANISM: Artificial Sequence
<220> FEATURE:
<223> OTHER INFORMATION: Synthetic Lactonase (CL00026320)

<400> SEQUENCE: 103

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Lys Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

-continued

```
Arg Ser Pro Arg Gln Asp Val Val Leu Gly Met Trp Arg Pro Leu Leu
            165                 170                 175

Glu Asp Ser Pro Glu Leu Ala Ala Leu Val Ser Gly Leu Thr Arg
        180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
        210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
            245                 250
```

```
<210> SEQ ID NO 104
<211> LENGTH: 753
<212> TYPE: DNA
<213> ORGANISM: Artificial Sequence
<220> FEATURE:
<223> OTHER INFORMATION: Synthetic Lactonase (CL00026320)

<400> SEQUENCE: 104
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacaagat ccccggggaa      240 ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc gcttctcga ggactcaccc      540 gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

```
<210> SEQ ID NO 105
<211> LENGTH: 251
<212> TYPE: PRT
<213> ORGANISM: Artificial Sequence
<220> FEATURE:
<223> OTHER INFORMATION: Synthetic Lactonase (CL00026328)

<400> SEQUENCE: 105

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Pro Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80
```

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 106
<211> LENGTH: 753
<212> TYPE: DNA
<213> ORGANISM: Artificial Sequence
<220> FEATURE:
<223> OTHER INFORMATION: Synthetic Lactonase (CL00026328)

<400> SEQUENCE: 106

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcacct gccgaagaac cgtacgacat ccccacgctc     180
gcgaccgacg tgcacgacac cctcgcgcag ctcgccgaga cgacgtgat ccccggggaa      240
ctgccggtga tcgtcggcca ctcgatgggg gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 107
<211> LENGTH: 251
<212> TYPE: PRT
<213> ORGANISM: Artificial Sequence
<220> FEATURE:
<223> OTHER INFORMATION: Synthetic Lactonase (CL00026344)

<400> SEQUENCE: 107

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
50                      55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile Thr Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 108
<211> LENGTH: 753
<212> TYPE: DNA
<213> ORGANISM: Artificial Sequence
<220> FEATURE:
<223> OTHER INFORMATION: Synthetic Lactonase (CL00026344)

<400> SEQUENCE: 108
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcaga aggcggaggg gatgctccgc ggggcggact cccgctgtt catcacgggc     420 atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
```

```
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 109
<211> LENGTH: 251
<212> TYPE: PRT
<213> ORGANISM: Artificial Sequence
<220> FEATURE:
<223> OTHER INFORMATION: Synthetic Lactonase (CL00026349)

<400> SEQUENCE: 109

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Arg Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 110
<211> LENGTH: 753
<212> TYPE: DNA
<213> ORGANISM: Artificial Sequence
<220> FEATURE:
<223> OTHER INFORMATION: Synthetic Lactonase (CL00026349)

<400> SEQUENCE: 110

```
atgatcctcg cccacgacgt gtcgggctcc ggcccgctgc tggtcctcct gcacggcatc     60
accgaagacc gccgcagctg ggatccggtc gatttcaccg acggcttcac ggtcgtgcgg    120
gtcgacctgc gcgggcacgg ggcatcagcc gccgaagaac cgtacgacat ccccacgctc    180
```

```
gcgaccgacg tgcacgacac cctcgcgcag ctcgccgaga acgacaggat ccccggggaa    240
ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact cccgctgttt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                753
```

<210> SEQ ID NO 111
<211> LENGTH: 251
<212> TYPE: PRT
<213> ORGANISM: Artificial Sequence
<220> FEATURE:
<223> OTHER INFORMATION: Synthetic Lactonase (CL00026369)

<400> SEQUENCE: 111

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile Lys Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 112
<211> LENGTH: 753
<212> TYPE: DNA
<213> ORGANISM: Artificial Sequence
<220> FEATURE:
<223> OTHER INFORMATION: Synthetic Lactonase (CL00026369)

<400> SEQUENCE: 112

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttc catcaagggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc ggaggacgt cccgtacctc     600
gtgatcacgg tctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                 753
```

<210> SEQ ID NO 113
<211> LENGTH: 251
<212> TYPE: PRT
<213> ORGANISM: Artificial Sequence
<220> FEATURE:
<223> OTHER INFORMATION: Synthetic Lactonase (CL00026396)

<400> SEQUENCE: 113

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Lys Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Lys Gln Asp Val Val Leu Gly Met Trp Arg Pro Leu Leu
                165                 170                 175
```

```
Glu Asp Ser Pro Glu Leu Ala Ala Leu Val Ser Gly Leu Thr Arg
                180                 185                 190
Ile Pro Glu Asp Val Pro Tyr Leu Val Ile Thr Gly Leu Asp Ala Gly
            195                 200                 205
Pro Glu Tyr Ala Ala Trp Leu Gln Arg Glu Ile Pro Gln Ala Val Gln
        210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250
```

<210> SEQ ID NO 114
<211> LENGTH: 753
<212> TYPE: DNA
<213> ORGANISM: Artificial Sequence
<220> FEATURE:
<223> OTHER INFORMATION: Synthetic Lactonase (CL00026396)

<400> SEQUENCE: 114

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgaagc aggcggaggg gatgctccgc ggggcggact tcccgctgtt catccacggc     420
atgttcgcgc agatggcggg cggcctggat gccgaggagc tggcgcgggt gaatggcatc     480
cggtctccga agcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 115
<211> LENGTH: 251
<212> TYPE: PRT
<213> ORGANISM: Artificial Sequence
<220> FEATURE:
<223> OTHER INFORMATION: Synthetic Lactonase (CL00026398)

<400> SEQUENCE: 115

```
Met Ile Leu Ala His Asp Val Ser Gly Ser Gly Pro Leu Leu Val Leu
1               5                   10                  15
Leu His Gly Ile Thr Glu Asp Arg Arg Ser Trp Asp Pro Val Asp Phe
            20                  25                  30
Thr Asp Gly Phe Thr Val Val Arg Val Asp Leu Arg Gly His Gly Ala
        35                  40                  45
Ser Ala Ala Glu Glu Pro Tyr Asp Ile Pro Thr Leu Ala Thr Asp Val
    50                  55                  60
His Asp Thr Leu Ala Gln Leu Ala Glu Asn Asp Val Ile Pro Gly Glu
65                  70                  75                  80
Leu Pro Val Ile Val Gly His Ser Met Gly Gly Ile Val Ala Thr Ala
                85                  90                  95
```

Tyr Gly Ala Leu Phe Pro Ala Arg Ala Ile Val Asn Val Asp Gln Pro
             100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Lys Arg Val Glu Ala Phe Val Arg
                245                 250

<210> SEQ ID NO 116
<211> LENGTH: 753
<212> TYPE: DNA
<213> ORGANISM: Artificial Sequence
<220> FEATURE:
<223> OTHER INFORMATION: Synthetic Lactonase (CL00026398)

<400> SEQUENCE: 116

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtca agcgcgtcga ggctttcgtc cgc                                   753
```

<210> SEQ ID NO 117
<211> LENGTH: 251
<212> TYPE: PRT
<213> ORGANISM: Artificial Sequence
<220> FEATURE:
<223> OTHER INFORMATION: Synthetic Lactonase (CL00026451)

<400> SEQUENCE: 117

Met Ile Leu Ala His Asp Val Ser Gly Ser Gly Pro Leu Leu Val Leu
1               5                   10                  15

```
Leu His Gly Ile Thr Glu Asp Arg Arg Ser Trp Asp Pro Val Asp Phe
             20                  25                  30

Thr Asp Gly Phe Thr Val Val Arg Val Asp Leu Arg Gly His Gly Ala
         35                  40                  45

Ser Ala Ala Glu Glu Pro Tyr Asp Ile Pro Thr Leu Ala Thr Asp Val
     50                  55                  60

His Asp Thr Leu Ala Gln Leu Ala Glu Asn Asp Val Ile Pro Gly Glu
 65                  70                  75                  80

Leu Pro Val Ile Val Gly His Ser Met Gly Gly Ile Val Ala Thr Ala
                 85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg His Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 118
<211> LENGTH: 753
<212> TYPE: DNA
<213> ORGANISM: Artificial Sequence
<220> FEATURE:
<223> OTHER INFORMATION: Synthetic Lactonase (CL00026451)

<400> SEQUENCE: 118

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggcatccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
```
cggttcgtcg agcgcgtcga ggctttcgtc cgc 753

<210> SEQ ID NO 119
<211> LENGTH: 251
<212> TYPE: PRT
<213> ORGANISM: Artificial Sequence
<220> FEATURE:
<223> OTHER INFORMATION: Synthetic Lactonase (CL00026455)

<400> SEQUENCE: 119

```
Met Ile Leu Ala His Asp Val Ser Gly Ser Gly Pro Leu Leu Val Leu
1               5                   10                  15
Leu His Gly Ile Thr Glu Asp Arg Arg Ser Trp Asp Pro Val Asp Phe
            20                  25                  30
Thr Asp Gly Phe Thr Val Val Arg Val Asp Leu Arg Gly His Gly Ala
        35                  40                  45
Ser Ala Ala Glu Glu Pro Tyr Asp Ile Pro Thr Leu Ala Thr Asp Val
    50                  55                  60
His Asp Thr Leu Ala Gln Leu Ala Glu Asn Asp Val Ile Pro Gly Glu
65                  70                  75                  80
Leu Pro Val Ile Val Gly His Ser Met Gly Gly Ile Val Ala Thr Ala
                85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Gln Ala Glu Gly Met
        115                 120                 125
Leu Arg Gly Ala Asp Phe Pro Leu Phe Ile His Gly Met Phe Ala Gln
    130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Gly Leu Thr Arg
            180                 185                 190
Ile Pro Glu Asp Val Pro Tyr Leu Val Ile Thr Gly Leu Asp Ala Gly
        195                 200                 205
Pro Glu Tyr Ala Ala Trp Leu Gln Arg Glu Ile Pro Gln Ala Val Gln
    210                 215                 220
Glu Val Trp Gln Pro Pro Thr His Tyr Pro His Leu Val Asp Pro Ala
225                 230                 235                 240
Arg Phe Val Ser Arg Val Glu Ala Phe Val Arg
                245                 250
```

<210> SEQ ID NO 120
<211> LENGTH: 753
<212> TYPE: DNA
<213> ORGANISM: Artificial Sequence
<220> FEATURE:
<223> OTHER INFORMATION: Synthetic Lactonase (CL00026455)

<400> SEQUENCE: 120
atgatcctcg cccacgacgt gtcgggctcc ggcccgctgc tggtcctcct gcacggcatc    60
accgaagacc gccgcagctg ggatccggtc gatttcaccg acggcttcac ggtcgtgcgg   120
gtcgacctgc gcgggcacgg ggcatcagcc gccgaagaac cgtacgacat ccccacgctc   180
gcgaccgacg tgcacgacac cctcgcgcag ctcgccgaga acgacgtgat ccccggggaa   240
ctgccggtga tcgtcggcca ctcgatgggc gggatcgtcg cgacggcgta cggcgcgctc   300

```
ttccccgcgc gggcgatcgt caacgtggac cagcctctcc agctcgcggg catgcagggc    360
caggtgcagg aggcggaggg gatgctccgc ggggcggact tcccgctgtt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc ggaggacgt cccgtacctc     600 gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtct cgcgcgtcga ggctttcgtc cgc                                 753
```

<210> SEQ ID NO 121
<211> LENGTH: 251
<212> TYPE: PRT
<213> ORGANISM: Artificial Sequence
<220> FEATURE:
<223> OTHER INFORMATION: Synthetic Lactonase (CL00026470)

<400> SEQUENCE: 121

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg His Gly Ala
        35                  40                  45

Ser Ala Glu Glu Pro Tyr Asp Ile Pro Thr Leu Ala Thr Asp Val
    50                  55                  60

His Asp Thr Leu Ala Ser Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 122
<211> LENGTH: 753
<212> TYPE: DNA

<213> ORGANISM: Artificial Sequence
<220> FEATURE:
<223> OTHER INFORMATION: Synthetic Lactonase (CL00026470)

<400> SEQUENCE: 122

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgagt ctcgccgaga cgacgtgat ccccggggaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc      420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc gcacctcgt cgacccggca      720
cggttcgtcg agcgcgtcga ggctttcgtc cgc                                   753
```

<210> SEQ ID NO 123
<211> LENGTH: 251
<212> TYPE: PRT
<213> ORGANISM: Artificial Sequence
<220> FEATURE:
<223> OTHER INFORMATION: Synthetic Lactonase (CL00026476)

<400> SEQUENCE: 123

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
```

-continued

```
                195                 200                 205
Pro Glu Tyr Ala Ala Trp Leu Gln Arg Glu Ile Pro Gln Ala Val Gln
            210                 215                 220

Glu Val Trp Gln Pro Pro Thr His Tyr Pro His Leu Val Asp Pro Ala
225                 230                 235                 240

Arg Phe Val Thr Arg Val Glu Ala Phe Val Arg
                245                 250
```

<210> SEQ ID NO 124
<211> LENGTH: 753
<212> TYPE: DNA
<213> ORGANISM: Artificial Sequence
<220> FEATURE:
<223> OTHER INFORMATION: Synthetic Lactonase (CL00026476)

<400> SEQUENCE: 124

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtca ctcgcgtcga ggctttcgtc cgc                                  753
```

<210> SEQ ID NO 125
<211> LENGTH: 251
<212> TYPE: PRT
<213> ORGANISM: Artificial Sequence
<220> FEATURE:
<223> OTHER INFORMATION: Synthetic Lactonase (CL00026535)

<400> SEQUENCE: 125

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
```

```
              115                 120                 125
Leu Arg Gly Ala Asp Phe Pro Leu Phe Ile His Gly Met Phe Ala Gln
        130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Arg Arg Val Glu Ala Phe Val Arg
                245                 250
```

<210> SEQ ID NO 126
<211> LENGTH: 753
<212> TYPE: DNA
<213> ORGANISM: Artificial Sequence
<220> FEATURE:
<223> OTHER INFORMATION: Synthetic Lactonase (CL00026535)

<400> SEQUENCE: 126

```
atgatcctcg cccacgacgt gtcgggctcc ggcccgctgc tggtcctcct gcacggcatc     60
accgaagacc gccgcagctg ggatccggtc gatttcaccg acggcttcac ggtcgtgcgg    120
gtcgacctgc gcgggcacgg cgcatcagcc gccgaagaac cgtacgacat ccccacgctc    180
gcgaccgacg tgcacgacac cctcgcgcag ctcgccgaga cgacgtgat ccccggggaa    240
ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact tcccgctgtt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcc ggcgcgtcga ggctttcgtc cgc                                 753
```

<210> SEQ ID NO 127
<211> LENGTH: 251
<212> TYPE: PRT
<213> ORGANISM: Artificial Sequence
<220> FEATURE:
<223> OTHER INFORMATION: Synthetic Lactonase (CL00026540)

<400> SEQUENCE: 127

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
```

```
              35                  40                  45
Ser Ala Glu Glu Pro Tyr Asp Ile Pro Thr Leu Ala Thr Asp Val
 50                  55                  60

His Asp Thr Leu Ala Asn Leu Ala Glu Asn Asp Val Ile Pro Gly Glu
 65                  70                  75                  80

Leu Pro Val Ile Val Gly His Ser Met Gly Gly Ile Val Ala Thr Ala
                 85                  90                  95

Tyr Gly Ala Leu Phe Pro Ala Arg Ala Ile Val Asn Val Asp Gln Pro
                100                 105                 110

Leu Gln Leu Ala Gly Met Gln Gly Gln Val Gln Gln Ala Glu Gly Met
                115                 120                 125

Leu Arg Gly Ala Asp Phe Pro Leu Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
                180                 185                 190

Ile Pro Glu Asp Val Pro Tyr Leu Val Ile Thr Gly Leu Asp Ala Gly
                195                 200                 205

Pro Glu Tyr Ala Ala Trp Leu Gln Arg Glu Ile Pro Gln Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 128
<211> LENGTH: 753
<212> TYPE: DNA
<213> ORGANISM: Artificial Sequence
<220> FEATURE:
<223> OTHER INFORMATION: Synthetic Lactonase (CL00026540)

<400> SEQUENCE: 128
atgatcctcg cccacgacgt gtcgggctcc ggcccgctgc tggtcctcct gcacggcatc        60
accgaagacc gccgcagctg ggatccggtc gatttcaccg acggcttcac ggtcgtgcgg       120
gtcgacctgc gcgggcacgg ggcatcagcc gccgaagaac cgtacgacat ccccacgctc       180
gcgaccgacg tgcacgacac cctcgcgaat ctcgccgaga acgacgtgat ccccggggaa       240
ctgccggtga tcgtcggcca ctcgatgggc gggatcgtcg cgacggcgta cggcgcgctc       300
ttccccgcgc gggcgatcgt caacgtggac cagcctctcc agctcgcggg catgcagggc       360
caggtgcagc aggcggaggg gatgctccgc ggggcggact tcccgctgtt catccacggc       420
atgttcgcgc agatggcggg cggcctggat gccgaggagc tggcgcgggt gaatggcatc       480
cggtctccga ggcaggacgt cgtcctcggg atgtggcggc cgcttctcga ggactcaccc       540
gaagaactgg cggcgctcgt gagcggtctg acgaggatcc cggaggacgt cccgtacctc       600
gtgatcacgg gtctcgatgc cgggccagag tacgcggcgt ggctgcagcg ggagatcccg       660
caggccgtcc aggaggtctg gcagccgccg acccactacc cgcacctcgt cgacccggca       720
cggttcgtcg agcgcgtcga ggctttcgtc cgc                                    753

<210> SEQ ID NO 129
```

<211> LENGTH: 251
<212> TYPE: PRT
<213> ORGANISM: Artificial Sequence
<220> FEATURE:
<223> OTHER INFORMATION: Synthetic Lactonase (CL00026559)

<400> SEQUENCE: 129

```
Met Ile Leu Ala His Asp Val Ser Gly Ser Gly Pro Leu Leu Val Leu
1               5                   10                  15
Leu His Gly Ile Thr Glu Asp Arg Arg Ser Trp Asp Pro Val Asp Phe
            20                  25                  30
Thr Asp Gly Phe Thr Val Val Arg Val Asp Leu Arg Gly His Gly Ala
        35                  40                  45
Ser Ala Ala Glu Glu Pro Tyr Asp Ile Pro Thr Leu Ala Thr Asp Val
    50                  55                  60
His Asp Thr Leu Ala Tyr Leu Ala Glu Asn Asp Val Ile Pro Gly Glu
65                  70                  75                  80
Leu Pro Val Ile Val Gly His Ser Met Gly Gly Ile Val Ala Thr Ala
                85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Ala Glu Gly Met
        115                 120                 125
Leu Arg Gly Ala Asp Phe Pro Leu Phe Ile His Gly Met Phe Ala Gln
130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Gly Leu Thr Arg
            180                 185                 190
Ile Pro Glu Asp Val Pro Tyr Leu Val Ile Thr Gly Leu Asp Ala Gly
        195                 200                 205
Pro Glu Tyr Ala Ala Trp Leu Gln Arg Glu Ile Pro Gln Ala Val Gln
    210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250
```

<210> SEQ ID NO 130
<211> LENGTH: 753
<212> TYPE: DNA
<213> ORGANISM: Artificial Sequence
<220> FEATURE:
<223> OTHER INFORMATION: Synthetic Lactonase (CL00026559)

<400> SEQUENCE: 130

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgtat ctcgccgaga cgacgtgat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
```

```
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 131
<211> LENGTH: 251
<212> TYPE: PRT
<213> ORGANISM: Artificial Sequence
<220> FEATURE:
<223> OTHER INFORMATION: Synthetic Lactonase (CL00026564)

<400> SEQUENCE: 131

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Glu Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 132
<211> LENGTH: 753
<212> TYPE: DNA
<213> ORGANISM: Artificial Sequence
<220> FEATURE:
<223> OTHER INFORMATION: Synthetic Lactonase (CL00026564)

<400> SEQUENCE: 132

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgagat ccccggggaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc gcacctcgt cgacccggca     720
cggttcgtcg agcgcgtcga ggctttcgtc cgc                                  753
```

<210> SEQ ID NO 133
<211> LENGTH: 251
<212> TYPE: PRT
<213> ORGANISM: Artificial Sequence
<220> FEATURE:
<223> OTHER INFORMATION: Synthetic Lactonase (CL00026641)

<400> SEQUENCE: 133

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Leu Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220
```

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 134
<211> LENGTH: 753
<212> TYPE: DNA
<213> ORGANISM: Artificial Sequence
<220> FEATURE:
<223> OTHER INFORMATION: Synthetic Lactonase (CL00026641)

<400> SEQUENCE: 134
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacctgat ccccggggaa      240 ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc      420 atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753

<210> SEQ ID NO 135
<211> LENGTH: 251
<212> TYPE: PRT
<213> ORGANISM: Artificial Sequence
<220> FEATURE:
<223> OTHER INFORMATION: Synthetic Lactonase (CL00026661)

<400> SEQUENCE: 135

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Ala Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
            165                 170                 175

Glu Asp Ser Pro Glu Glu Leu Ala Ala Leu Val Ser Gly Leu Thr Arg
        180                 185                 190

Ile Pro Glu Asp Val Pro Tyr Leu Val Ile Thr Gly Leu Asp Ala Gly
            195                 200                 205

Pro Glu Tyr Ala Ala Trp Leu Gln Arg Glu Ile Pro Gln Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
            245                 250

<210> SEQ ID NO 136
<211> LENGTH: 753
<212> TYPE: DNA
<213> ORGANISM: Artificial Sequence
<220> FEATURE:
<223> OTHER INFORMATION: Synthetic Lactonase (CL00026661)

<400> SEQUENCE: 136

| | | | | | | |
|---|---|---|---|---|---|---|
| atgatcctcg | cccacgacgt | gtcgggctcc | ggcccgctgc | tggtcctcct | gcacggcatc | 60 |
| accgaagacc | gccgcagctg | ggatccggtc | gatttcaccg | acggcttcac | ggtcgtgcgg | 120 |
| gtcgacctgc | gcgggcacgg | ggcatcagcc | gccgaagaac | cgtacgacat | ccccacgctc | 180 |
| gcgaccgacg | tgcacgacac | cctcgcgcag | ctcgccgaga | cgacgctat | ccccggggaa | 240 |
| ctgccggtga | tcgtcggcca | ctcgatgggc | gggatcgtcg | cgacggcgta | cggcgcgctc | 300 |
| ttccccgcgc | gggcgatcgt | caacgtggac | cagcctctcc | agctcgcggg | catgcagggc | 360 |
| caggtgcagc | aggcggaggg | gatgctccgc | ggggcggact | cccgctgtt | catccacggc | 420 |
| atgttcgcgc | agatggcggg | cggcctggat | gccgaggagc | tggcgcgggt | gaatggcatc | 480 |
| cggtctccga | ggcaggacgt | cgtcctcggg | atgtggcggc | cgcttctcga | ggactcaccc | 540 |
| gaagaactgg | cggcgctcgt | gagcggtctg | acgaggatcc | cggaggacgt | cccgtacctc | 600 |
| gtgatcacgg | gtctcgatgc | cgggccagag | tacgcggcgt | ggctgcagcg | ggagatcccg | 660 |
| caggccgtcc | aggaggtctg | gcagccgccg | acccactacc | cgcacctcgt | cgacccggca | 720 |
| cggttcgtcg | agcgcgtcga | ggctttcgtc | cgc | | | 753 |

<210> SEQ ID NO 137
<211> LENGTH: 251
<212> TYPE: PRT
<213> ORGANISM: Artificial Sequence
<220> FEATURE:
<223> OTHER INFORMATION: Synthetic Lactonase (CL00026679)

<400> SEQUENCE: 137

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

```
His Asp Thr Leu Ala Gln Leu Ala Glu Asn Asp Val Ile Pro Gly Glu
 65                  70                  75                  80

Leu Pro Val Ile Val Gly His Ser Met Gly Gly Ile Val Ala Thr Ala
             85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
210                 215                 220

Glu Val Trp Gln Pro Pro Thr His Tyr Pro His Leu Val Asp Pro Ala
225                 230                 235                 240

Arg Phe Val Gly Arg Val Glu Ala Phe Val Arg
                245                 250
```

<210> SEQ ID NO 138
<211> LENGTH: 753
<212> TYPE: DNA
<213> ORGANISM: Artificial Sequence
<220> FEATURE:
<223> OTHER INFORMATION: Synthetic Lactonase (CL00026679)

<400> SEQUENCE: 138

```
atgatcctcg cccacgacgt gtcgggctcc ggcccgctgc tggtcctcct gcacggcatc    60
accgaagacc gccgcagctg ggatccggtc gatttcaccg acggcttcac ggtcgtgcgg   120
gtcgacctgc gcgggcacgg ggcatcagcc gccgaagaac cgtacgacat ccccacgctc   180
gcgaccgacg tgcacgacac cctcgcgcag ctcgccgaga cgacgtgat ccccggggaa    240
ctgccggtga tcgtcggcca ctcgatgggc gggatcgtcg cgacggcgta cggcgcgctc   300
ttccccgcgc gggcgatcgt caacgtggac cagcctctcc agctcgcggg catgcagggc   360
caggtgcagc aggcggaggg gatgctccgc ggggcggact cccgctgtt catccacggc    420
atgttcgcgc agatggcggg cggcctggat gccgaggagc tggcgcgggt gaatggcatc   480
cggtctccga ggcaggacgt cgtcctcggg atgtggcggc cgcttctcga ggactcaccc   540
gaagaactgg cggcgctcgt gagcggtctg acgaggatcc cggaggacgt cccgtacctc   600
gtgatcacgg gtctcgatgc cgggccagag tacgcggcgt ggctgcagcg ggagatcccg   660
caggccgtcc aggaggtctg gcagccgccg acccactacc cgcacctcgt cgacccggca   720
cggttcgtcg gcgcgtcga ggctttcgtc cgc                                 753
```

<210> SEQ ID NO 139
<211> LENGTH: 251
<212> TYPE: PRT
<213> ORGANISM: Artificial Sequence
<220> FEATURE:

<223> OTHER INFORMATION: Synthetic Lactonase (CL00026695)

<400> SEQUENCE: 139

| Met | Ile | Leu | Ala | His | Asp | Val | Ser | Gly | Ser | Gly | Pro | Leu | Leu | Val | Leu |
|---|---|---|---|---|---|---|---|---|---|---|---|---|---|---|---|
| 1 | | | | 5 | | | | | 10 | | | | | 15 | |

Leu His Gly Ile Thr Glu Asp Arg Arg Ser Trp Asp Pro Val Asp Phe
           20             25               30

Thr Asp Gly Phe Thr Val Val Arg Val Asp Leu Arg Gly His Gly Ala
        35                40             45

Ser Ala Ala Glu Glu Pro Tyr Asp Ile Pro Thr Leu Ala Thr Asp Val
50                   55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Asn Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 140
<211> LENGTH: 753
<212> TYPE: DNA
<213> ORGANISM: Artificial Sequence
<220> FEATURE:
<223> OTHER INFORMATION: Synthetic Lactonase (CL00026695)

<400> SEQUENCE: 140
atgatcctcg cccacgacgt gtcgggctcc ggcccgctgc tggtcctcct gcacggcatc   60
accgaagacc gccgcagctg ggatccggtc gatttcaccg acggcttcac ggtcgtgcgg  120
gtcgacctgc gcgggcacgg ggcatcagcc gccgaagaac cgtacgacat ccccacgctc  180
gcgaccgacg tgcacgacac cctcgcgcag ctcgccgaga acgacgtgat ccccggggaa  240
ctgccggtga tcgtcggcca ctcgatgggc gggatcgtcg cgacggcgta cggcgcgctc  300
ttccccgcgc gggcgatcgt caacgtggac cagcctctcc agctcgcggg catgcagggc  360
caggtgcagc aggcggaggg gatgctccgc ggggcggact cccgctgttt catccacggc  420
atgttcgcgc agatggcggg cggcctggat gccgaggagc tggcgcgggt gaatggcatc  480
cggtctccga ggcaggacgt cgtcctcggg atgtggcggc cgcttctcga ggactcaccc  540

```
gaagaactgg cggcgctcgt gaatggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 141
<211> LENGTH: 251
<212> TYPE: PRT
<213> ORGANISM: Artificial Sequence
<220> FEATURE:
<223> OTHER INFORMATION: Synthetic Lactonase (CL00026696)

<400> SEQUENCE: 141

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Asn Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 142
<211> LENGTH: 753
<212> TYPE: DNA
<213> ORGANISM: Artificial Sequence
<220> FEATURE:
<223> OTHER INFORMATION: Synthetic Lactonase (CL00026696)

<400> SEQUENCE: 142

```
atgatcctcg cccacgacgt gtcgggctcc ggcccgctgc tggtcctcct gcacggcatc     60
```

```
accgaagacc gccgcagctg ggatccggtc gatttcaccg acggcttcac ggtcgtgcgg      120
gtcgacctgc gcgggcacgg ggcatcagcc gccgaagaac cgtacgacat ccccacgctc      180
gcgaccgacg tgcacgacac cctcgcgcag ctcgccgaga acgacaatat ccccggggaa      240
ctgccggtga tcgtcggcca ctcgatgggc gggatcgtcg cgacggcgta cggcgcgctc      300
ttccccgcgc gggcgatcgt caacgtggac cagcctctcc agctcgcggg catgcagggc      360
caggtgcagc aggcggaggg gatgctccgc ggggcggact cccgctgtt catccacggc       420 atgttcgcgc agatggcggg cggcctggat gccgaggagc tggcgcgggt gaatggcatc      480
cggtctccga ggcaggacgt cgtcctcggg atgtggcggc cgcttctcga ggactcaccc      540
gaagaactgg cggcgctcgt gagcggtctg acgaggatcc cggaggacgt cccgtacctc      600
gtgatcacgg gtctcgatgc cgggccagag tacgcggcgt ggctgcagcg ggagatcccg      660
caggccgtcc aggaggtctg gcagccgccg acccactacc cgcacctcgt cgacccggca      720
cggttcgtcg agcgcgtcga ggctttcgtc cgc                                   753
```

<210> SEQ ID NO 143
<211> LENGTH: 251
<212> TYPE: PRT
<213> ORGANISM: Artificial Sequence
<220> FEATURE:
<223> OTHER INFORMATION: Synthetic Lactonase (CL00028441)

<400> SEQUENCE: 143

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Pro Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240
```

Arg Phe Val Glu Arg Val Glu Ala Phe Val Arg
                245                 250

<210> SEQ ID NO 144
<211> LENGTH: 753
<212> TYPE: DNA
<213> ORGANISM: Artificial Sequence
<220> FEATURE:
<223> OTHER INFORMATION: Synthetic Lactonase (CL00028441)

<400> SEQUENCE: 144

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240
cccccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg tctcgatgc cgggccagag tacgcggcgt ggctgcagcg ggagatcccg      660
caggccgtcc aggaggtctg gcagccgccg acccactacc cgcacctcgt cgacccggca     720
cggttcgtcg agcgcgtcga ggctttcgtc cgc                                   753
```

<210> SEQ ID NO 145
<211> LENGTH: 251
<212> TYPE: PRT
<213> ORGANISM: Artificial Sequence
<220> FEATURE:
<223> OTHER INFORMATION: Synthetic Lactonase (CL00028451)

<400> SEQUENCE: 145

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Pro Pro Val Val Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

```
Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 146
<211> LENGTH: 753
<212> TYPE: DNA
<213> ORGANISM: Artificial Sequence
<220> FEATURE:
<223> OTHER INFORMATION: Synthetic Lactonase (CL00028451)

<400> SEQUENCE: 146
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg gcatcagcc gccgaagaac cgtacgacat ccccacgctc     180
gcgaccgacg tgcacgacac cctcgcgcag ctcgccgaga acgacgtgat ccccggggaa     240
cccccggtgg tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc     420 atgttcgcgc agatggcggg cggcctggat gccgaggagc tggcgcgggt gaatggcatc     480
cggtctccga ggcaggacgt cgtcctcggg atgtggcggc gcttctcga ggactcaccc     540 gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                   753

<210> SEQ ID NO 147
<211> LENGTH: 251
<212> TYPE: PRT
<213> ORGANISM: Artificial Sequence
<220> FEATURE:
<223> OTHER INFORMATION: Synthetic Lactonase (CL00028468)

<400> SEQUENCE: 147

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Ala Asp Val
    50                  55                  60

His Asp Thr Leu Ala Gln Leu Ala Glu Asn Asp Val Ile Pro Ala Glu
65                  70                  75                  80
```

Leu Pro Val Ile Val Gly His Ser Met Gly Gly Ile Val Ala Thr Ala
            85                  90                  95

Tyr Gly Ala Leu Phe Pro Ala Arg Ala Ile Val Asn Val Asp Gln Pro
        100                 105                 110

Leu Gln Leu Ala Gly Met Gln Gly Gln Val Gln Ala Glu Gly Met
    115                 120                 125

Leu Arg Gly Ala Asp Phe Pro Leu Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Lys Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Val Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 148
<211> LENGTH: 753
<212> TYPE: DNA
<213> ORGANISM: Artificial Sequence
<220> FEATURE:
<223> OTHER INFORMATION: Synthetic Lactonase (CL00028468)

<400> SEQUENCE: 148

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcggccgacg tgcacgacac cctcgcgcag ctcgccgaga cgacgtgat ccccgccgaa      240 ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc      420 atgttcgcgc agatggcggg cggcctggat gccgaggagc tggcgcgggt gaatggcatc     480
cggtctccga agcaggacgt cgtcctcggg atgtggcggc cgcttctcga ggactcaccc     540
gaagaactgg cggcgctcgt gagcggtctg acgagggtcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 149
<211> LENGTH: 251
<212> TYPE: PRT
<213> ORGANISM: Artificial Sequence
<220> FEATURE:
<223> OTHER INFORMATION: Synthetic Lactonase (CL00028526)

<400> SEQUENCE: 149

| Met | Ile | Leu | Ala | His | Asp | Val | Ser | Gly | Ser | Gly | Pro | Leu | Leu | Val | Leu |
|---|---|---|---|---|---|---|---|---|---|---|---|---|---|---|---|
| 1 | | | | 5 | | | | | 10 | | | | | 15 | |

Leu His Gly Ile Thr Glu Asp Arg Arg Ser Trp Asp Pro Val Asp Phe
            20                    25                  30

Thr Asp Gly Phe Thr Val Val Arg Val Asp Leu Arg Gly His Gly Ala
          35                  40                    45

Ser Ala Ala Glu Glu Pro Tyr Asp Ile Pro Thr Leu Ala Thr Asp Val
50                  55                    60

His Asp Thr Leu Ala Gln Leu Ala Glu Asn Asp Val Ile Pro Ala Glu
65                  70              75              80

Pro Pro Val Ile Val Gly His Ser Met Gly Gly Ile Val Ala Thr Ala
                  85                  90              95

Tyr Gly Ala Leu Phe Pro Ala Arg Ala Ile Val Asn Val Asp Gln Pro
          100               105              110

Leu Gln Leu Ala Gly Met Gln Gly Gln Val Gln Gln Ala Glu Gly Met
          115               120              125

Leu Arg Gly Ala Asp Phe Pro Leu Phe Ile His Gly Met Phe Ala Gln
    130                 135              140

Met Ala Gly Gly Leu Asp Ala Glu Glu Leu Ala Arg Val Asn Gly Ile
145                  150              155              160

Arg Ser Pro Arg Gln Asp Val Val Leu Gly Met Trp Arg Pro Leu Leu
          165               170              175

Glu Asp Ser Pro Glu Glu Leu Ala Ala Leu Val Ser Gly Leu Thr Arg
          180               185              190

Ile Pro Glu Asp Val Pro Tyr Leu Val Ile Thr Gly Leu Asp Ala Gly
          195               200              205

Pro Glu Tyr Ala Ala Trp Leu Gln Arg Glu Ile Pro Gln Ala Val Gln
    210                 215              220

Glu Val Trp Gln Pro Pro Thr His Tyr Pro His Leu Val Asp Pro Ala
225                  230              235              240

Arg Phe Val Glu Arg Val Glu Ala Phe Val Arg
          245               250

<210> SEQ ID NO 150
<211> LENGTH: 753
<212> TYPE: DNA
<213> ORGANISM: Artificial Sequence
<220> FEATURE:
<223> OTHER INFORMATION: Synthetic Lactonase (CL00028526)

<400> SEQUENCE: 150

| atgatcctcg | cccacgacgt | gtcgggctcc | ggcccgctgc | tggtcctcct | gcacggcatc | 60 |
| accgaagacc | gccgcagctg | ggatccggtc | gatttcaccg | acggcttcac | ggtcgtgcgg | 120 |
| gtcgacctgc | gcgggcacgg | ggcatcagcc | gccgaagaac | cgtacgacat | ccccacgctc | 180 |
| gcgaccgacg | tgcacgacac | cctcgcgcag | ctcgccgaga | acgacgtgat | ccccgccgaa | 240 |
| ccccccggtga | tcgtcggcca | ctcgatgggc | gggatcgtcg | cgacggcgta | cggcgcgctc | 300 |
| ttccccgcgc | gggcgatcgt | caacgtggac | cagcctctcc | agctcgcggg | catgcagggc | 360 |
| caggtgcagc | aggcggaggg | gatgctccgc | ggggcggact | tcccgctgtt | catccacggc | 420 |
| atgttcgcgc | agatggcggg | cggcctggat | gccgaggagc | tggcgcgggt | gaatggcatc | 480 |
| cggtctccga | ggcaggacgt | cgtcctcggg | atgtggcggc | cgcttctcga | ggactcaccc | 540 |
| gaagaactgg | cggcgctcgt | gagcggtctg | acgaggatcc | cggaggacgt | cccgtacctc | 600 |
| gtgatcacgg | gtctcgatgc | cgggccagag | tacgcggcgt | ggctgcagcg | ggagatcccg | 660 |

```
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 151
<211> LENGTH: 251
<212> TYPE: PRT
<213> ORGANISM: Artificial Sequence
<220> FEATURE:
<223> OTHER INFORMATION: Synthetic Lactonase (CL00028549)

<400> SEQUENCE: 151

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Ala Glu
65                  70                  75                  80

Leu Pro Val Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Ile Gln Ala Glu Gly Met
        115                 120                 125

Leu Arg Gly Ala Asp Phe Pro Leu Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 152
<211> LENGTH: 753
<212> TYPE: DNA
<213> ORGANISM: Artificial Sequence
<220> FEATURE:
<223> OTHER INFORMATION: Synthetic Lactonase (CL00028549)

<400> SEQUENCE: 152

```
atgatcctcg cccacgacgt gtcgggctcc ggcccgctgc tggtcctcct gcacggcatc    60
accgaagacc gccgcagctg ggatccggtc gatttcaccg acggcttcac ggtcgtgcgg   120
gtcgacctgc gcgggcacgg ggcatcagcc gccgaagaac cgtacgacat ccccacgctc   180
```

-continued

```
gcgaccgacg tgcacgacac cctcgcgcag ctcgccgaga acgacgtgat ccccgccgaa    240
ctgccggtgg tcgtcggcca ctcgatgggc gggatcgtcg cgacggcgta cggcgcgctc    300
ttccccgcgc gggcgatcgt caacgtggac cagcctctcc agctcgcggg catgcagggc    360
cagatccagc aggcggaggg gatgctccgc ggggcggact cccgctgttt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

```
<210> SEQ ID NO 153
<211> LENGTH: 251
<212> TYPE: PRT
<213> ORGANISM: Artificial Sequence
<220> FEATURE:
<223> OTHER INFORMATION: Synthetic Lactonase (CL00028564)

<400> SEQUENCE: 153
```

```
Met Ile Leu Ala His Asp Val Ser Gly Ser Gly Pro Leu Leu Val Leu
 1               5                  10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Ala Asp Val
    50                  55                  60

His Asp Thr Leu Ala Gln Leu Ala Glu Asn Asp Val Ile Pro Gly Glu
65                  70                  75                  80

Pro Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Ile Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Val Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

-continued

```
<210> SEQ ID NO 154
<211> LENGTH: 753
<212> TYPE: DNA
<213> ORGANISM: Artificial Sequence
<220> FEATURE:
<223> OTHER INFORMATION: Synthetic Lactonase (CL00028564)

<400> SEQUENCE: 154
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcggccgacg tgcacgacac cctcgcgcag ctcgccgaga acgacgtgat ccccggggaa     240
cccccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
cagatccagc aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgagggtcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                 753

<210> SEQ ID NO 155
<211> LENGTH: 251
<212> TYPE: PRT
<213> ORGANISM: Artificial Sequence
<220> FEATURE:
<223> OTHER INFORMATION: Synthetic Lactonase (CL00028574)

<400> SEQUENCE: 155

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Ala Asp Val
    50                  55                  60

His Asp Thr Leu Ala Gln Leu Ala Glu Asn Asp Val Ile Pro Ala Glu
65                  70                  75                  80

Pro Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
            115                 120                 125

Leu Arg Gly Ala Asp Phe Pro Leu Phe Ile His Gly Met Phe Ala Gln
        130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
```

```
                180              185              190
Ile Pro Glu Asp Val Pro Tyr Leu Val Ile Thr Gly Leu Asp Ala Gly
            195                  200                  205

Pro Glu Tyr Ala Ala Trp Leu Gln Arg Glu Ile Pro Gln Ala Val Gln
            210                  215                  220

Glu Val Trp Gln Pro Pro Thr His Tyr Pro His Leu Val Asp Pro Ala
225                  230                  235                  240

Arg Phe Val Glu Arg Val Glu Ala Phe Val Arg
                245                  250

<210> SEQ ID NO 156
<211> LENGTH: 753
<212> TYPE: DNA
<213> ORGANISM: Artificial Sequence
<220> FEATURE:
<223> OTHER INFORMATION: Synthetic Lactonase (CL00028574)

<400> SEQUENCE: 156
```

| | | | | |
|---|---|---|---|---|
| atgatcctcg cccacgacgt gtcgggctcc ggcccgctgc tggtcctcct gcacggcatc | | | | 60 |
| accgaagacc gccgcagctg ggatccggtc gatttcaccg acggcttcac ggtcgtgcgg | | | | 120 |
| gtcgacctgc gcgggcacgg gcatcagcc gccgaagaac cgtacgacat ccccacgctc | | | | 180 |
| gcggccgacg tgcacgacac cctcgcgcag ctcgccgaga cgacgtgat ccccgccgaa | | | | 240 |
| cccccggtga tcgtcggcca ctcgatgggc gggatcgtcg cgacggcgta cggcgcgctc | | | | 300 |
| ttccccgcgc gggcgatcgt caacgtggac cagcctctcc agctcgcggg catgcagggc | | | | 360 |
| caggtgcagc aggcggaggg gatgctccgc ggggcggact tcccgctgtt catccacggc | | | | 420 |
| atgttcgcgc agatggcggg cggcctggat gccgaggagc tggcgcgggt gaatggcatc | | | | 480 |
| cggtctccga ggcaggacgt cgtcctcggg atgtggcggc cgcttctcga ggactcaccc | | | | 540 |
| gaagaactgg cggcgctcgt gagcggtctg acgaggatcc ggaggacgt cccgtacctc | | | | 600 |
| gtgatcacgg gtctcgatgc cgggccagag tacgcggcgt ggctgcagcg ggagatcccg | | | | 660 |
| caggccgtcc aggaggtctg gcagccgccg acccactacc cgcacctcgt cgacccggca | | | | 720 |
| cggttcgtcg agcgcgtcga ggctttcgtc cgc | | | | 753 |

```
<210> SEQ ID NO 157
<211> LENGTH: 251
<212> TYPE: PRT
<213> ORGANISM: Artificial Sequence
<220> FEATURE:
<223> OTHER INFORMATION: Synthetic Lactonase (CL00028598)

<400> SEQUENCE: 157

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Ala Asp Val
        50                  55                  60

His Asp Thr Leu Ala Gln Leu Ala Glu Asn Asp Val Ile Pro Ala Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
```

```
            100                 105                 110
Leu Gln Leu Ala Gly Met Gln Gly Gln Val Gln Gln Ala Glu Gly Met
            115                 120                 125

Leu Arg Gly Ala Asp Phe Pro Leu Phe Ile His Gly Met Phe Ala Gln
        130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 158
<211> LENGTH: 753
<212> TYPE: DNA
<213> ORGANISM: Artificial Sequence
<220> FEATURE:
<223> OTHER INFORMATION: Synthetic Lactonase (CL00028598)

<400> SEQUENCE: 158

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcggccgacg tgcacgacac cctcgcgcag ctcgccgaga cgacgtgat ccccgccgaa      240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact ccccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgaccggca      720
cggttcgtcg agcgcgtcga ggctttcgtc cgc                                   753
```

<210> SEQ ID NO 159
<211> LENGTH: 251
<212> TYPE: PRT
<213> ORGANISM: Artificial Sequence
<220> FEATURE:
<223> OTHER INFORMATION: Synthetic Lactonase (CL00028616)

<400> SEQUENCE: 159

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
```

```
                  20                  25                  30
Thr Asp Gly Phe Thr Val Val Arg Val Asp Leu Arg Gly His Gly Ala
                35                  40                  45
Ser Ala Ala Glu Glu Pro Tyr Asp Ile Pro Thr Leu Ala Thr Asp Val
    50                  55                  60
His Asp Thr Leu Ala Gln Leu Ala Glu Asn Asp Val Ile Pro Gly Glu
65                  70                  75                  80
Pro Pro Val Ile Val Gly His Ser Met Gly Gly Ile Val Ala Thr Ala
                85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Gln Ala Glu Gly Met
        115                 120                 125
Leu Arg Gly Ala Asp Phe Pro Leu Phe Ile His Gly Met Phe Ala Gln
    130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Glu Leu Val Ser Gly Leu Thr Arg
            180                 185                 190
Ile Pro Glu Asp Val Pro Tyr Leu Val Ile Thr Gly Leu Asp Ala Gly
        195                 200                 205
Pro Glu Tyr Ala Ala Trp Leu Gln Arg Glu Ile Pro Gln Ala Val Gln
    210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250

<210> SEQ ID NO 160
<211> LENGTH: 753
<212> TYPE: DNA
<213> ORGANISM: Artificial Sequence
<220> FEATURE:
<223> OTHER INFORMATION: Synthetic Lactonase (CL00028616)

<400> SEQUENCE: 160
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccggggaa     240
cccccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgttc atccacggc      420 atgttcgcgc agatggcggg cggcctggat gccgaggagc tggcgcgggt gaatggcatc     480
cggtctccga gcaggacgt cgtcctcggg atgtggcggc cgttctcga ggactcaccc       540 gaagaactgg cggagctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgaccggca      720 cggttcgtcg agcgcgtcga ggctttcgtc cgc                                  753
```

<210> SEQ ID NO 161
<211> LENGTH: 251
<212> TYPE: PRT
<213> ORGANISM: Artificial Sequence
<220> FEATURE:
<223> OTHER INFORMATION: Synthetic Lactonase (CL00028623)

<400> SEQUENCE: 161

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Ala Glu
65                  70                  75                  80

Pro Pro Val Val Val Gly His Ser Met Gly Gly Ile Val Ala Thr Ala
                85                  90                  95

Tyr Gly Ala Leu Phe Pro Ala Arg Ala Ile Val Asn Val Asp Gln Pro
                100                 105                 110

Leu Gln Leu Ala Gly Met Gln Gly Gln Val Gln Ala Glu Gly Met
            115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Asp Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
                180                 185                 190

Ile Pro Glu Asp Val Pro Tyr Leu Val Ile Thr Gly Leu Asp Ala Gly
            195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 162
<211> LENGTH: 753
<212> TYPE: DNA
<213> ORGANISM: Artificial Sequence
<220> FEATURE:
<223> OTHER INFORMATION: Synthetic Lactonase (CL00028623)

<400> SEQUENCE: 162

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccgccgaa     240
cccccggtgg tcgtcggcca ctcgatgggc gggatcgtcg cgacggcgta cggcgcgctc     300
```

```
ttccccgcgc gggcgatcgt caacgtggac cagcctctcc agctcgcggg catgcagggc    360
caggtgcagc aggcggaggg gatgctccgc ggggcggact tcccgctgtt catccacggc    420
atgttcgcgc agatggcggg cggcctggat gccgaggagc tggatcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 163
<211> LENGTH: 251
<212> TYPE: PRT
<213> ORGANISM: Artificial Sequence
<220> FEATURE:
<223> OTHER INFORMATION: Synthetic Lactonase (CL00028629)

<400> SEQUENCE: 163

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Asp Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Asp Thr Val Ala Gln Leu Ala Glu Asn Asp Val Ile Pro Gly Glu
65                  70                  75                  80

Pro Pro Val Val Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Asp Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Val Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 164
<211> LENGTH: 753
<212> TYPE: DNA
<213> ORGANISM: Artificial Sequence
<220> FEATURE:
<223> OTHER INFORMATION: Synthetic Lactonase (CL00028629)

<400> SEQUENCE: 164

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cgtcgcgcag ctcgccgaga cgacgtgat ccccggggaa      240
ccccggtgg tcgtcggcca ctcgatgggc gggatcgtcg cgacggcgta cggcgcgctc      300
ttccccgcgc gggcgatcgt caacgtggac cagcctctcc agctcgcggg catgcagggc     360
caggtgcagc aggcggaggg gatgctccgc ggggcggact cccgctgtt catccacggc      420
atgttcgcgc agatggcggg cggcctggat gccgaggagc tggatcgggt gaatggcatc     480
cggtctccga ggcaggacgt cgtcctcggg atgtggcggc cgcttctcga ggactcaccc     540
gaagaactgg cggcgctcgt gagcggtctg acgagggtcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc gcacctcgt cgacccggca      720
cggttcgtcg agcgcgtcga ggctttcgtc cgc                                  753
```

<210> SEQ ID NO 165
<211> LENGTH: 251
<212> TYPE: PRT
<213> ORGANISM: Artificial Sequence
<220> FEATURE:
<223> OTHER INFORMATION: Synthetic Lactonase (CL00028657)

<400> SEQUENCE: 165

```
Met Ile Leu Ala His Asp Val Ser Gly Ser Gly Pro Leu Leu Val Leu
  1               5                  10                  15

Leu His Gly Ile Thr Glu Asp Arg Arg Ser Trp Asp Pro Val Asp Phe
             20                  25                  30

Thr Asp Gly Phe Thr Val Val Arg Val Asp Leu Arg Gly His Gly Ala
         35                  40                  45

Ser Ala Ala Glu Glu Pro Tyr Asp Ile Pro Thr Leu Ala Thr Asp Val
     50                  55                  60

His Asp Thr Leu Ala Gln Leu Ala Glu Asn Asp Val Ile Pro Gly Glu
 65                  70                  75                  80

Pro Pro Val Val Gly His Ser Met Gly Gly Ile Val Ala Thr Ala
                 85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Val Pro Glu Asp Val Pro Tyr Leu Val Ile Thr Gly Leu Asp Ala Gly
        195                 200                 205
```

Pro Glu Tyr Ala Ala Trp Leu Gln Arg Glu Ile Pro Gln Ala Val Gln
        210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 166
<211> LENGTH: 753
<212> TYPE: DNA
<213> ORGANISM: Artificial Sequence
<220> FEATURE:
<223> OTHER INFORMATION: Synthetic Lactonase (CL00028657)

<400> SEQUENCE: 166
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg gcatcagcc gccgaagaac cgtacgacat ccccacgctc     180
gcgaccgacg tgcacgacac cctcgcgcag ctcgccgaga cgacgtgat ccccggggaa     240 cccccggtgg tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc     420 atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgagggtcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753

<210> SEQ ID NO 167
<211> LENGTH: 251
<212> TYPE: PRT
<213> ORGANISM: Artificial Sequence
<220> FEATURE:
<223> OTHER INFORMATION: Synthetic Lactonase (CL00028669)

<400> SEQUENCE: 167

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Leu
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Pro Pro Val Val Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
            165                 170                 175

Glu Asp Ser Pro Glu Glu Leu Ala Ala Leu Val Ser Gly Leu Thr Arg
            180                 185                 190

Val Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
            245                 250

<210> SEQ ID NO 168
<211> LENGTH: 753
<212> TYPE: DNA
<213> ORGANISM: Artificial Sequence
<220> FEATURE:
<223> OTHER INFORMATION: Synthetic Lactonase (CL00028669)

<400> SEQUENCE: 168
atgatcctcg cccacgacgt gtcgggctcc ggcccgctgc tggtcctcct gcacggcatc      60
accgaagacc gccgcagctg ggatccggtc gatctgaccg acggcttcac ggtcgtgcgg     120
gtcgacctgc gcgggcacgg ggcatcagcc ccgaagaac cgtacgacat ccccacgctc      180
gcgaccgacg tgcacgacac cctcgcgcag ctcgccgaga cgacgtgat ccccggggaa      240 ccccccggtgg tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact cccgctgtt catccacggc      420 atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgagggtcc cggaggacgt cccgtacctc    600
gtgatcacgg tctcgatgc cgggccagag tacgcggcgt ggctgcagcg ggagatcccg     660
caggccgtcc aggaggtctg gcagccgccg acccactacc cgcacctcgt cgaccggca     720 cggttcgtcg agcgcgtcga ggctttcgtc cgc                                 753

<210> SEQ ID NO 169
<211> LENGTH: 251
<212> TYPE: PRT
<213> ORGANISM: Artificial Sequence
<220> FEATURE:
<223> OTHER INFORMATION: Synthetic Lactonase (CL00028670)

<400> SEQUENCE: 169

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

```
Ser Ala Ala Glu Glu Pro Tyr Asp Ile Pro Thr Leu Ala Thr Asp Val
 50                  55                  60

His Asp Thr Val Ala Gln Leu Ala Glu Asn Asp Val Ile Pro Gly Glu
 65                  70                  75                  80

Pro Pro Val Val Val Gly His Ser Met Gly Gly Ile Val Ala Thr Ala
                 85                  90                  95

Tyr Gly Ala Leu Phe Pro Ala Arg Ala Ile Val Asn Val Asp Gln Pro
                100                 105                 110

Leu Gln Leu Ala Gly Met Gln Gly Gln Val Gln Gln Ala Glu Gly Met
            115                 120                 125

Leu Arg Gly Ala Asp Phe Pro Leu Phe Ile His Gly Met Phe Ala Gln
        130                 135                 140

Met Ala Gly Gly Leu Asp Ala Glu Glu Leu Ala Arg Val Asn Gly Ile
145                 150                 155                 160

Arg Ser Pro Lys Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 170
<211> LENGTH: 753
<212> TYPE: DNA
<213> ORGANISM: Artificial Sequence
<220> FEATURE:
<223> OTHER INFORMATION: Synthetic Lactonase (CL00028670)

<400> SEQUENCE: 170
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cgtcgcgcag ctcgccgaga cgacgtgat ccccggggaa      240 cccccggtgg tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga agcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753

<210> SEQ ID NO 171
<211> LENGTH: 251
```

```
<212> TYPE: PRT
<213> ORGANISM: Artificial Sequence
<220> FEATURE:
<223> OTHER INFORMATION: Synthetic Lactonase (CL00028687)

<400> SEQUENCE: 171
```

| Met | Ile | Leu | Ala | His | Asp | Val | Ser | Gly | Ser | Gly | Pro | Leu | Leu | Val | Leu |
|---|---|---|---|---|---|---|---|---|---|---|---|---|---|---|---|
| 1 | | | | 5 | | | | | 10 | | | | | 15 | |

| Leu | His | Gly | Ile | Thr | Glu | Asp | Arg | Arg | Ser | Trp | Asp | Pro | Val | Asp | Phe |
|---|---|---|---|---|---|---|---|---|---|---|---|---|---|---|---|
| | | | 20 | | | | | 25 | | | | | 30 | | |

| Thr | Asp | Gly | Phe | Thr | Val | Val | Arg | Val | Asp | Leu | Arg | Gly | His | Gly | Ala |
|---|---|---|---|---|---|---|---|---|---|---|---|---|---|---|---|
| | | | 35 | | | | | 40 | | | | | 45 | | |

| Ser | Ala | Ala | Glu | Glu | Pro | Tyr | Asp | Ile | Pro | Thr | Leu | Ala | Thr | Asp | Val |
|---|---|---|---|---|---|---|---|---|---|---|---|---|---|---|---|
| | 50 | | | | | 55 | | | | | 60 | | | | |

| His | Asp | Thr | Leu | Ala | Gln | Leu | Ala | Glu | Asn | Asp | Val | Ile | Pro | Ala | Glu |
|---|---|---|---|---|---|---|---|---|---|---|---|---|---|---|---|
| 65 | | | | | 70 | | | | | 75 | | | | | 80 |

| Leu | Pro | Val | Ile | Val | Gly | His | Ser | Met | Gly | Gly | Ile | Val | Ala | Thr | Ala |
|---|---|---|---|---|---|---|---|---|---|---|---|---|---|---|---|
| | | | | 85 | | | | | 90 | | | | | 95 | |

| Tyr | Gly | Ala | Leu | Phe | Pro | Ala | Arg | Ala | Ile | Val | Asn | Val | Asp | Gln | Pro |
|---|---|---|---|---|---|---|---|---|---|---|---|---|---|---|---|
| | | | 100 | | | | | 105 | | | | | 110 | | |

| Leu | Gln | Leu | Ala | Gly | Met | Gln | Gly | Gln | Val | Gln | Gln | Ala | Glu | Gly | Met |
|---|---|---|---|---|---|---|---|---|---|---|---|---|---|---|---|
| | | | 115 | | | | | 120 | | | | | 125 | | |

| Leu | Arg | Gly | Ala | Asp | Phe | Pro | Leu | Phe | Ile | His | Gly | Met | Phe | Ala | Gln |
|---|---|---|---|---|---|---|---|---|---|---|---|---|---|---|---|
| | 130 | | | | | 135 | | | | | 140 | | | | |

| Met | Ala | Gly | Gly | Leu | Asp | Ala | Glu | Glu | Leu | Ala | Arg | Val | Asn | Gly | Ile |
|---|---|---|---|---|---|---|---|---|---|---|---|---|---|---|---|
| 145 | | | | | 150 | | | | | 155 | | | | | 160 |

| Arg | Ser | Pro | Arg | Gln | Asp | Val | Val | Leu | Gly | Met | Trp | Arg | Pro | Leu | Leu |
|---|---|---|---|---|---|---|---|---|---|---|---|---|---|---|---|
| | | | | 165 | | | | | 170 | | | | | 175 | |

| Glu | Asp | Ser | Pro | Glu | Glu | Leu | Ala | Ala | Leu | Val | Ser | Gly | Leu | Thr | Arg |
|---|---|---|---|---|---|---|---|---|---|---|---|---|---|---|---|
| | | | 180 | | | | | 185 | | | | | 190 | | |

| Ile | Pro | Glu | Asp | Val | Pro | Tyr | Leu | Val | Ile | Thr | Gly | Leu | Asp | Ala | Gly |
|---|---|---|---|---|---|---|---|---|---|---|---|---|---|---|---|
| | | | 195 | | | | | 200 | | | | | 205 | | |

| Pro | Glu | Tyr | Ala | Ala | Trp | Leu | Gln | Arg | Glu | Ile | Pro | Gln | Ala | Val | Gln |
|---|---|---|---|---|---|---|---|---|---|---|---|---|---|---|---|
| | 210 | | | | | 215 | | | | | 220 | | | | |

| Glu | Val | Trp | Gln | Pro | Pro | Thr | His | Tyr | Pro | His | Leu | Val | Asp | Pro | Ala |
|---|---|---|---|---|---|---|---|---|---|---|---|---|---|---|---|
| 225 | | | | | 230 | | | | | 235 | | | | | 240 |

| Arg | Phe | Val | Glu | Arg | Val | Glu | Ala | Phe | Val | Arg |
|---|---|---|---|---|---|---|---|---|---|---|
| | | | 245 | | | | | 250 | | |

```
<210> SEQ ID NO 172
<211> LENGTH: 753
<212> TYPE: DNA
<213> ORGANISM: Artificial Sequence
<220> FEATURE:
<223> OTHER INFORMATION: Synthetic Lactonase (CL00028687)

<400> SEQUENCE: 172
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccgccgaa     240
ctgccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
```

```
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc ggaggacgt cccgtacctc     600 gtgatcacgg tctcgatgc cgggccagag tacgcggcgt ggctgcagcg ggagatcccg    660
caggccgtcc aggaggtctg gcagccgccg acccactacc gcacctcgt cgacccggca    720 cggttcgtcg agcgcgtcga ggctttcgtc cgc                                  753
```

<210> SEQ ID NO 173
<211> LENGTH: 251
<212> TYPE: PRT
<213> ORGANISM: Artificial Sequence
<220> FEATURE:
<223> OTHER INFORMATION: Synthetic Lactonase (CL00028741)

<400> SEQUENCE: 173

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Ala Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Ile Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Lys Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 174
<211> LENGTH: 753
<212> TYPE: DNA
<213> ORGANISM: Artificial Sequence
<220> FEATURE:
<223> OTHER INFORMATION: Synthetic Lactonase (CL00028741)

<400> SEQUENCE: 174

```
atgatcctcg cccacgacgt gtcgggctcc ggcccgctgc tggtcctcct gcacggcatc    60
accgaagacc gccgcagctg ggatccggtc gatttcaccg acggcttcac ggtcgtgcgg   120
gtcgacctgc gcgggcacgg ggcatcagcc gccgaagaac cgtacgacat ccccacgctc   180
gcgaccgacg tgcacgacac cctcgcgcag ctcgccgaga acgacgtgat ccccgccgaa   240
ctgccggtga tcgtcggcca ctcgatgggc gggatcgtcg cgacggcgta cggcgcgctc   300
ttccccgcgc gggcgatcgt caacgtggac cagcctctcc agctcgcggg catgcagggc   360
cagatccagc aggcggaggg gatgctccgc ggggcggact cccgctgtt catccacggc   420
atgttcgcgc agatggcggg cggcctggat gccgaggagc tggcgcgggt gaatggcatc   480
cggtctccga agcaggacgt cgtcctcggg atgtggcggc cgcttctcga ggactcaccc   540
gaagaactgg cggcgctcgt gagcggtctg acgaggatcc cggaggacgt cccgtacctc   600
gtgatcacgg gtctcgatgc cgggccagag tacgcggcgt ggctgcagcg ggagatcccg   660
caggccgtcc aggaggtctg gcagccgccg acccactacc cgcacctcgt cgacccggca   720
cggttcgtcg agcgcgtcga ggctttcgtc cgc                                753
```

<210> SEQ ID NO 175
<211> LENGTH: 251
<212> TYPE: PRT
<213> ORGANISM: Artificial Sequence
<220> FEATURE:
<223> OTHER INFORMATION: Synthetic Lactonase (CL00028745)

<400> SEQUENCE: 175

```
Met Ile Leu Ala His Asp Val Ser Gly Ser Gly Pro Leu Leu Val Leu
1               5                   10                  15
Leu His Gly Ile Thr Glu Asp Arg Arg Ser Trp Asp Pro Val Asp Phe
            20                  25                  30
Thr Asp Gly Phe Thr Val Val Arg Val Asp Leu Arg Gly His Gly Ala
        35                  40                  45
Ser Ala Ala Glu Glu Pro Tyr Asp Ile Pro Thr Leu Ala Thr Asp Val
    50                  55                  60
His Asp Thr Leu Ala Gln Leu Ala Glu Asn Asp Val Ile Pro Ala Glu
65                  70                  75                  80
Leu Pro Val Val Gly His Ser Met Gly Gly Ile Val Ala Thr Ala
                85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Gln Ala Glu Gly Met
        115                 120                 125
Leu Arg Gly Ala Asp Phe Pro Leu Phe Ile His Gly Met Phe Ala Gln
    130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Gly Leu Thr Arg
            180                 185                 190
Ile Pro Glu Asp Val Pro Tyr Leu Val Ile Thr Gly Leu Asp Ala Gly
        195                 200                 205
Pro Glu Tyr Ala Ala Trp Leu Gln Arg Glu Ile Pro Gln Ala Val Gln
    210                 215                 220
```

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 176
<211> LENGTH: 753
<212> TYPE: DNA
<213> ORGANISM: Artificial Sequence
<220> FEATURE:
<223> OTHER INFORMATION: Synthetic Lactonase (CL00028745)

<400> SEQUENCE: 176
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccgccgaa     240
ctgccggtgg tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcaga aggcggaggg gatgctccgc ggggcggact cccgctgttt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                 753

<210> SEQ ID NO 177
<211> LENGTH: 251
<212> TYPE: PRT
<213> ORGANISM: Artificial Sequence
<220> FEATURE:
<223> OTHER INFORMATION: Synthetic Lactonase (CL00028752)

<400> SEQUENCE: 177

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Ile Gln Gln Ala Glu Gly Met
        115                 120                 125

Leu Arg Gly Ala Asp Phe Pro Leu Phe Ile His Gly Met Phe Ala Gln
    130                 135                 140

```
Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
            165                 170                 175

Glu Asp Ser Pro Glu Glu Leu Ala Ala Leu Val Ser Gly Leu Thr Arg
        180                 185                 190

Val Pro Glu Asp Val Pro Tyr Leu Val Ile Thr Gly Leu Asp Ala Gly
    195                 200                 205

Pro Glu Tyr Ala Ala Trp Leu Gln Arg Glu Ile Pro His Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
            245                 250
```

<210> SEQ ID NO 178
<211> LENGTH: 753
<212> TYPE: DNA
<213> ORGANISM: Artificial Sequence
<220> FEATURE:
<223> OTHER INFORMATION: Synthetic Lactonase (CL00028752)

<400> SEQUENCE: 178

```
atgatcctcg cccacgacgt gtcgggctcc ggcccgctgc tggtcctcct gcacggcatc     60
accgaagacc gccgcagctg ggatccggtc gatttcaccg acggcttcac ggtcgtgcgg    120
gtcgacctgc gcgggcacgg ggcatcagcc gccgaagaac cgtacgacat ccccacgctc    180
gcgaccgacg tgcacgacac cctcgcgcag ctcgccgaga cgacgtgat ccccggggaa     240
ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
cagatccagc aggcggaggg gatgctccgc ggggcggact cccgctgtt catccacggc     420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgagggtcc cggaggacgt cccgtacctc    600
gtgatcacgg tctcgatgc cgggccagag tacgcggcgt ggctgcagcg ggagatcccg    660
cacgccgtcc aggaggtctg gcagccgccg acccactacc cgcacctcgt cgaccggca    720
cggttcgtcg agcgcgtcga ggctttcgtc cgc                                 753
```

<210> SEQ ID NO 179
<211> LENGTH: 251
<212> TYPE: PRT
<213> ORGANISM: Artificial Sequence
<220> FEATURE:
<223> OTHER INFORMATION: Synthetic Lactonase (CL00028754)

<400> SEQUENCE: 179

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60
```

| | | | | | | | | | | | | | | | |
|---|---|---|---|---|---|---|---|---|---|---|---|---|---|---|---|
|His|Asp|Thr|Leu|Ala|Gln|Leu|Ala|Glu|Asn|Asp|Val|Ile|Pro|Gly|Glu|
|65| | | |70| | | |75| | | |80| | | |

Pro Pro Val Ile Val Gly His Ser Met Gly Gly Ile Val Ala Thr Ala
              85                  90                  95

Tyr Gly Ala Leu Phe Pro Ala Arg Ala Ile Val Asn Val Asp Gln Pro
              100                 105                 110

Leu Gln Leu Ala Gly Met Gln Gly Gln Ile Gln Gln Ala Glu Gly Met
          115                 120                 125

Leu Arg Gly Ala Asp Phe Pro Leu Phe Ile His Gly Met Phe Ala Gln
      130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
              165                 170                 175

Glu Asp Ser Pro Glu Glu Leu Ala Ala Leu Val Ser Gly Leu Thr Arg
              180                 185                 190

Ile Pro Glu Asp Val Pro Tyr Leu Val Ile Thr Gly Leu Asp Ala Gly
          195                 200                 205

Pro Glu Tyr Ala Ala Trp Leu Gln Arg Glu Ile Pro Gln Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
              245                 250

<210> SEQ ID NO 180
<211> LENGTH: 753
<212> TYPE: DNA
<213> ORGANISM: Artificial Sequence
<220> FEATURE:
<223> OTHER INFORMATION: Synthetic Lactonase (CL00028754)

<400> SEQUENCE: 180

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga cgacgtgat ccccggggaa      240 cccccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
cagatccagc aggcggaggg gatgctccgc ggggcggact cccgctgtt catccacggc      420 atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 181
<211> LENGTH: 251
<212> TYPE: PRT
<213> ORGANISM: Artificial Sequence
<220> FEATURE:
<223> OTHER INFORMATION: Synthetic Lactonase (CL00028773)

<400> SEQUENCE: 181

| | | | | | | | | | | | | | | |
|---|---|---|---|---|---|---|---|---|---|---|---|---|---|---|
|Met|Ile|Leu|Ala|His|Asp|Val|Ser|Gly|Ser|Gly|Pro|Leu|Leu|Val|Leu|
|1| | | |5| | | | |10| | | | |15| |

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Ala Asp Val
    50                  55                  60

His Asp Thr Leu Ala Gln Leu Ala Glu Asn Asp Val Ile Pro Ala Glu
65                  70                  75                  80

Pro Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Val Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro His Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
            245                 250

<210> SEQ ID NO 182
<211> LENGTH: 753
<212> TYPE: DNA
<213> ORGANISM: Artificial Sequence
<220> FEATURE:
<223> OTHER INFORMATION: Synthetic Lactonase (CL00028773)

<400> SEQUENCE: 182

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcggccgacg tgcacgacac cctcgcgcag ctcgccgaga acgacgtgat ccccgccgaa     240
cccccggtga tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccgctgtt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
```

```
gaagaactgg cggcgctcgt gagcggtctg acgagggtcc cggaggacgt cccgtacctc    600
gtgatcacgg gtctcgatgc cgggccagag tacgcggcgt ggctgcagcg ggagatcccg    660
cacgccgtcc aggaggtctg gcagccgccg acccactacc cgcacctcgt cgacccggca    720
cggttcgtcg agcgcgtcga ggctttcgtc cgc                                  753
```

<210> SEQ ID NO 183
<211> LENGTH: 251
<212> TYPE: PRT
<213> ORGANISM: Artificial Sequence
<220> FEATURE:
<223> OTHER INFORMATION: Synthetic Lactonase (CL00028835)

<400> SEQUENCE: 183

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Ala Asp Val
    50                  55                  60

His Asp Thr Val Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Ile Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Lys Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 184
<211> LENGTH: 753
<212> TYPE: DNA
<213> ORGANISM: Artificial Sequence
<220> FEATURE:
<223> OTHER INFORMATION: Synthetic Lactonase (CL00028835)

<400> SEQUENCE: 184

```
atgatcctcg cccacgacgt gtcgggctcc ggcccgctgc tggtcctcct gcacggcatc     60
accgaagacc gccgcagctg ggatccggtc gatttcaccg acggcttcac ggtcgtgcgg    120
```

```
gtcgacctgc gcgggcacgg ggcatcagcc gccgaagaac cgtacgacat ccccacgctc    180
gcggccgacg tgcacgacac cgtcgcgcag ctcgccgaga cgacgtgat ccccggggaa    240 ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
cagatccagc aggcggaggg gatgctccgc ggggcggact cccgctgtt catccacggc    420 atgttcgcgc agatggcggg cggcctggat gccgaggagc tggcgcgggt gaatggcatc    480
cggtctccga agcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 185
<211> LENGTH: 251
<212> TYPE: PRT
<213> ORGANISM: Artificial Sequence
<220> FEATURE:
<223> OTHER INFORMATION: Synthetic Lactonase (CL00028844)

<400> SEQUENCE: 185

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Ala Asp Val
    50                  55                  60

His Asp Thr Leu Ala Gln Leu Ala Glu Asn Asp Val Ile Pro Gly Glu
65                  70                  75                  80

Pro Pro Val Val Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
```

<210> SEQ ID NO 186
<211> LENGTH: 753
<212> TYPE: DNA
<213> ORGANISM: Artificial Sequence
<220> FEATURE:
<223> OTHER INFORMATION: Synthetic Lactonase (CL00028844)

<400> SEQUENCE: 186

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcggccgacg tgcacgacac cctcgcgcag ctcgccgaga cgacgtgat ccccggggaa      240
cccccggtgg tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc      420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc ggaggacgt cccgtacctc      600
gtgatcacgg tctcgatgc cgggccagag tacgcggcgt ggctgcagcg ggagatcccg      660
caggccgtcc aggaggtctg gcagccgccg acccactacc gcacctcgt cgacccggca      720
cggttcgtcg agcgcgtcga ggctttcgtc cgc                                   753
```

<210> SEQ ID NO 187
<211> LENGTH: 251
<212> TYPE: PRT
<213> ORGANISM: Artificial Sequence
<220> FEATURE:
<223> OTHER INFORMATION: Synthetic Lactonase (CL00028864)

<400> SEQUENCE: 187

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Asp Thr Leu Ala Gln Leu Ala Glu Asn Asp Val Ile Pro Gly Glu
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Ile Gln Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
```

|  | 165 |  |  | 170 |  |  | 175 |  |
|---|---|---|---|---|---|---|---|---|

Glu Asp Ser Pro Glu Glu Leu Ala Ala Leu Val Ser Gly Leu Thr Arg
        180              185              190

Ile Pro Glu Asp Val Pro Tyr Leu Val Ile Thr Gly Leu Asp Ala Gly
    195              200              205

Pro Glu Tyr Ala Ala Trp Leu Gln Arg Glu Ile Pro Gln Ala Val Gln
  210              215              220

Glu Val Trp Gln Pro Pro Thr His Tyr Pro His Leu Val Asp Pro Ala
225            230              235            240

Arg Phe Val Glu Arg Val Glu Ala Phe Val Arg
          245              250

<210> SEQ ID NO 188
<211> LENGTH: 753
<212> TYPE: DNA
<213> ORGANISM: Artificial Sequence
<220> FEATURE:
<223> OTHER INFORMATION: Synthetic Lactonase (CL00028864)

<400> SEQUENCE: 188

```
atgatcctcg cccacgacgt gtcgggctcc ggcccgctgc tggtcctcct gcacggcatc     60
accgaagacc gccgcagctg ggatccggtc gatttcaccg acggcttcac ggtcgtgcgg    120
gtcgacctgc gcgggcacgg ggcatcagcc gccgaagaac cgtacgacat ccccacgctc    180
gcgaccgacg tgcacgacac cctcgcgcag ctcgccgaga acgacgtgat ccccggggaa    240
ctgccggtga tcgtcggcca ctcgatgggc gggatcgtcg cgacggcgta cggcgcgctc    300
ttccccgcgc gggcgatcgt caacgtggac cagcctctcc agctcgcggg catgcagggc    360
cagatccagc aggcggaggg gatgctccgc ggggcggact cccgctgttc atccacggc     420
atgttcgcgc agatggcggg cggcctggat ccgaggagc tggcgcgggt gaatggcatc    480
cggtctccga ggcaggacgt cgtcctcggg atgtggcggc cgcttctcga ggactcaccc    540
gaagaactgg cggcgctcgt gagcggtctg acgaggatcc cggaggacgt cccgtacctc    600
gtgatcacgg tctcgatgc cgggccagag tacgcggcgt ggctgcagcg ggagatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 189
<211> LENGTH: 251
<212> TYPE: PRT
<213> ORGANISM: Artificial Sequence
<220> FEATURE:
<223> OTHER INFORMATION: Synthetic Lactonase (CL00028867)

<400> SEQUENCE: 189

Met Ile Leu Ala His Asp Val Ser Gly Ser Gly Pro Leu Leu Val Leu
1            5                10              15

Leu His Gly Ile Thr Glu Asp Arg Arg Ser Trp Asp Pro Val Asp Phe
           20               25             30

Thr Asp Gly Phe Thr Val Val Arg Val Asp Leu Arg Gly His Gly Ala
            35                40             45

Ser Ala Ala Glu Glu Pro Tyr Asp Ile Pro Thr Leu Ala Thr Asp Val
    50              55              60

His Asp Thr Leu Ala Gln Leu Ala Glu Asn Asp Val Ile Pro Ala Glu
65            70              75            80

Leu Pro Val Ile Val Gly His Ser Met Gly Gly Ile Val Ala Thr Ala

```
                85                  90                  95
Tyr Gly Ala Leu Phe Pro Ala Arg Ala Ile Val Asn Val Asp Gln Pro
            100                 105                 110

Leu Gln Leu Ala Gly Met Gln Gly Gln Ile Gln Ala Glu Gly Met
        115                 120                 125

Leu Arg Gly Ala Asp Phe Pro Leu Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 190
<211> LENGTH: 753
<212> TYPE: DNA
<213> ORGANISM: Artificial Sequence
<220> FEATURE:
<223> OTHER INFORMATION: Synthetic Lactonase (CL00028867)

<400> SEQUENCE: 190
atgatcctcg cccacgacgt gtcgggctcc ggcccgctgc tggtcctcct gcacggcatc       60
accgaagacc gccgcagctg ggatccggtc gatttcaccg acggcttcac ggtcgtgcgg      120
gtcgacctgc gcgggcacgg ggcatcagcc gccgaagaac cgtacgacat ccccacgctc      180
gcgaccgacg tgcacgacac cctcgcgcag ctcgccgaga cgacgtgat  ccccgccgaa      240 ctgccggtga tcgtcggcca ctcgatgggc gggatcgtcg cgacggcgta cggcgcgctc      300
ttccccgcgc gggcgatcgt caacgtggac cagcctctcc agctcgcggg catgcagggc      360
cagatccagc aggcggaggg gatgctccgc ggggcggact cccgctgtt  catccacggc      420 atgttcgcgc agatggcggg cggcctggat gccgaggagc tggcgcgggt gaatggcatc      480
cggtctccga ggcaggacgt cgtcctcggg atgtggcggc cgcttctcga ggactcaccc      540
gaagaactgg cggcgctcgt gagcggtctg acgaggatcc cggaggacgt cccgtacctc      600
gtgatcacgg gtctcgatgc cgggccagag tacgcggcgt ggctgcagcg ggagatcccg      660
caggccgtcc aggaggtctg gcagccgccg acccactacc cgcacctcgt cgacccggca      720
cggttcgtcg agcgcgtcga ggctttcgtc cgc                                   753

<210> SEQ ID NO 191
<211> LENGTH: 251
<212> TYPE: PRT
<213> ORGANISM: Artificial Sequence
<220> FEATURE:
<223> OTHER INFORMATION: Synthetic Lactonase (CL00028868)

<400> SEQUENCE: 191

Met Ile Leu Ala His Asp Val Ser Gly Ser Gly Pro Leu Leu Val Leu
```

```
  1               5                  10                 15
Leu His Gly Ile Thr Glu Asp Arg Arg Ser Trp Asp Pro Val Asp Phe
            20                  25                 30

Thr Asp Gly Phe Thr Val Val Arg Val Asp Leu Arg Gly His Gly Ala
            35                  40                 45

Ser Ala Ala Glu Glu Pro Tyr Asp Ile Pro Thr Leu Ala Thr Asp Val
 50                  55                 60

His Asp Thr Leu Ala Gln Leu Ala Glu Asn Asp Val Ile Pro Ala Glu
 65                  70                 75                 80

Leu Pro Val Ile Val Gly His Ser Met Gly Gly Ile Val Ala Thr Ala
                 85                 90                 95

Tyr Gly Ala Leu Phe Pro Ala Arg Ala Ile Val Asn Val Asp Gln Pro
                100                105                110

Leu Gln Leu Ala Gly Met Gln Gly Gln Val Gln Ala Glu Gly Met
            115                120                 125

Leu Arg Gly Ala Asp Phe Pro Leu Phe Ile His Gly Met Phe Ala Gln
            130                135                 140

Met Ala Gly Gly Leu Asp Ala Glu Glu Leu Ala Arg Val Asn Gly Ile
145                 150                155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                190

Val Pro Glu Asp Val Pro Tyr Leu Val Ile Thr Gly Leu Asp Ala Gly
            195                 200                205

Pro Glu Tyr Ala Ala Trp Leu Gln Arg Glu Ile Pro Gln Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 192
<211> LENGTH: 753
<212> TYPE: DNA
<213> ORGANISM: Artificial Sequence
<220> FEATURE:
<223> OTHER INFORMATION: Synthetic Lactonase (CL00028868)

<400> SEQUENCE: 192

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgacac cctcgcgcag ctcgccgaga acgacgtgat ccccgccgaa     240
ctgccggtga tcgtcggcca ctcgatgggc ggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccgctgtt catccacggc     420 atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgagggtcc cggaggacgt cccgtacctc     600
gtgatcacgg gtctcgatgc cgggccagag tacgcggcgt ggctgcagcg ggagatcccg     660
```
caggccgtcc aggaggtctg gcagccgccg acccactacc cgcacctcgt cgacccggca    720
cggttcgtcg agcgcgtcga ggctttcgtc cgc    753

<210> SEQ ID NO 193
<211> LENGTH: 251
<212> TYPE: PRT
<213> ORGANISM: Artificial Sequence
<220> FEATURE:
<223> OTHER INFORMATION: Synthetic Lactonase (CL00028915)

<400> SEQUENCE: 193

```
Met Ile Leu Ala His Asp Val Ser Gly Ser Gly Pro Leu Val Leu
1               5                   10                  15

Leu His Gly Ile Thr Glu Asp Arg Arg Ser Trp Asp Pro Val Asp Phe
                20                  25                  30

Thr Lys Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Ile Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Asn Ala Leu Val Ser Arg Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 194
<211> LENGTH: 753
<212> TYPE: DNA
<213> ORGANISM: Artificial Sequence
<220> FEATURE:
<223> OTHER INFORMATION: Synthetic Lactonase (CL00028915)

<400> SEQUENCE: 194
atgatcctcg cccacgacgt gtcgggctcc ggcccgctgc tggtcctcct gcacggcatc    60
accgaagacc gccgcagctg ggatccggtc gatttcacca agggcttcac ggtcgtgcgg    120
gtcgacctgc gcgggcacgg ggcatcagcc gccgaagaac cgtacgacat ccccacgctc    180
gcgaccgacg tgcacgagac cctcgcgcag ctcgccgaga acgacgtgat ccccgggggc    240

```
ctgccgatca tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact cccggtctt catccacggc     420 atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactga acgcgctcgt gagccgcctg acgaggatcc cggaggacgt cccgtacctc    600
gtgatcacgg tctcgatgc cgggccagag tacgcggcgt ggctgcagcg ggagatcccg     660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 195
<211> LENGTH: 251
<212> TYPE: PRT
<213> ORGANISM: Artificial Sequence
<220> FEATURE:
<223> OTHER INFORMATION: Synthetic Lactonase (CL00028922)

<400> SEQUENCE: 195

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Lys Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Ile Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Asn Ala Leu Val Ser Arg Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Thr Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 196

<211> LENGTH: 753
<212> TYPE: DNA
<213> ORGANISM: Artificial Sequence
<220> FEATURE:
<223> OTHER INFORMATION: Synthetic Lactonase (CL00028922)

<400> SEQUENCE: 196

```
atgatcctcg cccacgacgt gtcgggctcc ggcccgctgc tggtcctcct gcacggcatc    60
accgaagacc gccgcagctg ggatccggtc gatttcacca agggcttcac ggtcgtgcgg   120
gtcgacctgc gcgggcacgg gcatcagcc gccgaagaac cgtacgacat ccccacgctc   180
gcgaccgacg tgcacgagac cctcgcgcag ctcgccgaga cgacgtgat ccccgggggc   240
ctgccgatca tcgtcggcca ctcgatgggc gggatcgtcg cgacggcgta cggcgcgctc   300
ttccccgcgc gggcgatcgt caacgtggac cagcctctcc agctcgcggg catgcagggc   360
caggtgcagc aggcggaggg gatgctccgc ggggcggact cccggtcttt catccacggc   420
atgttcgcgc agatggcggg cggcctggat gccgaggagc tggcgcgggt gaatggcatc   480
cggtctccga ggcaggacgt cgtcctcggg atgtggcggc cgcttctcga ggactcaccc   540
gaagaactga acgcgctcgt gagccgcctg acgaggatcc cggaggacgt cccgtacctc   600
gtgatcacgg gtctcgatgc cgggccagag tacgcggcgt ggctgcagcg gaccatcccg   660
caggccgtcc aggaggtctg gcagccgccg acccactacc gcacctcgt cgacccggca   720
cggttcgtcg agcgcgtcga ggctttcgtc cgc                                753
```

<210> SEQ ID NO 197
<211> LENGTH: 251
<212> TYPE: PRT
<213> ORGANISM: Artificial Sequence
<220> FEATURE:
<223> OTHER INFORMATION: Synthetic Lactonase (CL00028925)

<400> SEQUENCE: 197

```
Met Ile Leu Ala His Asp Val Ser Gly Ser Gly Pro Leu Leu Val Leu
 1               5                   10                  15

Leu His Gly Ile Thr Glu Asp Arg Arg Ser Trp Asp Pro Val Asp Phe
            20                  25                  30

Thr Lys Gly Phe Thr Val Val Arg Val Asp Leu Arg Gly His Gly Ala
        35                  40                  45

Ser Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Ile Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190
```

Ile Pro Glu Asp Val Pro Tyr Leu Val Ile Thr Gly Leu Asp Ala Gly
            195                 200                 205

Pro Glu Tyr Ala Ala Trp Leu Gln Arg Glu Ile Pro Gln Ala Val Gln
        210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
            245                 250

<210> SEQ ID NO 198
<211> LENGTH: 753
<212> TYPE: DNA
<213> ORGANISM: Artificial Sequence
<220> FEATURE:
<223> OTHER INFORMATION: Synthetic Lactonase (CL00028925)

<400> SEQUENCE: 198

```
atgatcctcg cccacgacgt gtcgggctcc ggcccgctgc tggtcctcct gcacggcatc      60
accgaagacc gccgcagctg ggatccggtc gatttcacca agggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga cgacgtgat ccccggggc      240
ctgccgatca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact ccccggtctt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg tctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 199
<211> LENGTH: 251
<212> TYPE: PRT
<213> ORGANISM: Artificial Sequence
<220> FEATURE:
<223> OTHER INFORMATION: Synthetic Lactonase (CL00028945)

<400> SEQUENCE: 199

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Lys Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Ile Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
            115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Asn Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 200
<211> LENGTH: 753
<212> TYPE: DNA
<213> ORGANISM: Artificial Sequence
<220> FEATURE:
<223> OTHER INFORMATION: Synthetic Lactonase (CL00028945)

<400> SEQUENCE: 200
atgatcctcg cccacgacgt gtcgggctcc ggcccgctgc tggtcctcct gcacggcatc      60
accgaagacc gccgcagctg ggatccggtc gatttcacca agggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga cgacgtgat ccccgggggc      240 ctgccgatca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccggtctt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactga acgcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                 753

<210> SEQ ID NO 201
<211> LENGTH: 251
<212> TYPE: PRT
<213> ORGANISM: Artificial Sequence
<220> FEATURE:
<223> OTHER INFORMATION: Synthetic Lactonase (CL00028948)

<400> SEQUENCE: 201

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Lys Gly Phe Thr Val Val Arg Val Asp Leu Arg Gly His Gly Ala
    35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
                100                 105                 110

Leu Gln Leu Ala Gly Met Gln Gly Gln Val Gln Ala Glu Gly Met
    115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
                180                 185                 190

Ile Pro Glu Asp Val Pro Tyr Leu Val Ile Thr Gly Leu Asp Ala Gly
                195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 202
<211> LENGTH: 753
<212> TYPE: DNA
<213> ORGANISM: Artificial Sequence
<220> FEATURE:
<223> OTHER INFORMATION: Synthetic Lactonase (CL00028948)

<400> SEQUENCE: 202
atgatcctcg cccacgacgt gtcgggctcc ggcccgctgc tggtcctcct gcacggcatc      60
accgaagacc gccgcagctg ggatccggtc gatttcacca agggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga acgacgtgat ccccggggc      240 ctgccggtca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccggtcttc atccacggc      420 atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgaccggca      720 cggttcgtcg agcgcgtcga ggctttcgtc cgc                                  753

<210> SEQ ID NO 203
<211> LENGTH: 251
<212> TYPE: PRT
<213> ORGANISM: Artificial Sequence
<220> FEATURE:
<223> OTHER INFORMATION: Synthetic Lactonase (CL00028964)

<400> SEQUENCE: 203

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
                20                  25                  30

Thr Lys Gly Phe Thr Val Val Arg Val Asp Leu Arg Gly His Gly Ala
            35                  40                  45

Ser Ala Ala Glu Glu Pro Tyr Asp Ile Pro Thr Leu Ala Thr Asp Val
        50                  55                  60

His Glu Thr Leu Ala Gln Leu Ala Glu Asn Asp Val Ile Pro Gly Gly
65                  70                  75                  80

Leu Pro Ile Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Val Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Asn Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Thr Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 204
<211> LENGTH: 753
<212> TYPE: DNA
<213> ORGANISM: Artificial Sequence
<220> FEATURE:
<223> OTHER INFORMATION: Synthetic Lactonase (CL00028964)

<400> SEQUENCE: 204

```
atgatcctcg cccacgacgt gtcgggctcc ggcccgctgc tggtcctcct gcacggcatc    60
accgaagacc gccgcagctg ggatccggtc gatttcacca agggcttcac ggtcgtgcgg   120
gtcgacctgc gcgggcacgg ggcatcagcc gccgaagaac cgtacgacat ccccacgctc   180
gcgaccgacg tgcacgagac cctcgcgcag ctcgccgaga acgacgtgat ccccgggggc   240
ctgccgatca tcgtcggcca ctcgatgggg ggatcgtcg cgacggcgta cggcgcgctc   300
ttccccgcgc gggcgatcgt caacgtggac cagcctctcc agctcgcggg catgcagggc   360
```

```
caggtgcagc aggcggaggg gatgctccgc ggggcggact tcccggtctt catccacggc    420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactga acgcgctcgt gagcggtctg acgaggatcc cggaggacgt cccgtacctc    600
gtgatcacgg gtctcgatgc cgggccagag tacgcggcgt ggctgcagcg gaccatcccg    660
caggccgtcc aggaggtctg gcagccgccg acccactacc cgcacctcgt cgacccggca    720
cggttcgtcg agcgcgtcga ggctttcgtc cgc                                 753
```

<210> SEQ ID NO 205
<211> LENGTH: 251
<212> TYPE: PRT
<213> ORGANISM: Artificial Sequence
<220> FEATURE:
<223> OTHER INFORMATION: Synthetic Lactonase (CL00028973)

<400> SEQUENCE: 205

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 206
<211> LENGTH: 753
<212> TYPE: DNA
<213> ORGANISM: Artificial Sequence
<220> FEATURE:

<223> OTHER INFORMATION: Synthetic Lactonase (CL00028973)

<400> SEQUENCE: 206

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga acgacgtgat ccccgggggc     240
ctgccggtca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccggtctt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc gcacctcgt cgacccggca      720
cggttcgtcg agcgcgtcga ggctttcgtc cgc                                   753
```

<210> SEQ ID NO 207
<211> LENGTH: 251
<212> TYPE: PRT
<213> ORGANISM: Artificial Sequence
<220> FEATURE:
<223> OTHER INFORMATION: Synthetic Lactonase (CL00028979)

<400> SEQUENCE: 207

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Lys Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Asn Ala Leu Val Ser Arg Leu Thr Arg
            180                 185                 190

Ile Pro Glu Asp Val Pro Tyr Leu Val Ile Thr Gly Leu Asp Ala Gly
        195                 200                 205
```

Pro Glu Tyr Ala Ala Trp Leu Gln Arg Thr Ile Pro Gln Ala Val Gln
        210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250

<210> SEQ ID NO 208
<211> LENGTH: 753
<212> TYPE: DNA
<213> ORGANISM: Artificial Sequence
<220> FEATURE:
<223> OTHER INFORMATION: Synthetic Lactonase (CL00028979)

<400> SEQUENCE: 208
atgatcctcg cccacgacgt gtcgggctcc ggcccgctgc tggtcctcct gcacggcatc     60
accgaagacc gccgcagctg ggatccggtc gatttcacca agggcttcac ggtcgtgcgg    120
gtcgacctgc gcgggcacgg gcatcagcc gccgaagaac cgtacgacat ccccacgctc    180
gcgaccgacg tgcacgagac cctcgcgcag ctcgccgaga cgacgtgat ccccggggc    240 ctgccggtca tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc ggggcggact cccggtcttc atccacggc    420 atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactga acgcgctcgt gagccgcctg acgaggatcc cggaggacgt cccgtacctc    600
gtgatcacgg gtctcgatgc cgggccagag tacgcggcgt ggctgcagcg gaccatcccg    660
caggccgtcc aggaggtctg gcagccgccg acccactacc cgcacctcgt cgacccggca    720
cggttcgtcg agcgcgtcga ggctttcgtc cgc                                 753

<210> SEQ ID NO 209
<211> LENGTH: 251
<212> TYPE: PRT
<213> ORGANISM: Artificial Sequence
<220> FEATURE:
<223> OTHER INFORMATION: Synthetic Lactonase (CL00029127)

<400> SEQUENCE: 209

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Lys Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
            115                 120                 125

Leu Arg Gly Ala Asp Phe Pro Val Phe Ile His Gly Met Phe Ala Gln
130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
            165                 170                 175

Glu Asp Ser Pro Glu Glu Leu Ala Ala Leu Val Ser Arg Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
            245                 250

<210> SEQ ID NO 210
<211> LENGTH: 753
<212> TYPE: DNA
<213> ORGANISM: Artificial Sequence
<220> FEATURE:
<223> OTHER INFORMATION: Synthetic Lactonase (CL00029127)

<400> SEQUENCE: 210
atgatcctcg cccacgacgt gtcgggctcc ggcccgctgc tggtcctcct gcacggcatc      60
accgaagacc gccgcagctg ggatccggtc gatttcacca agggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga cgacgtgat ccccgggggc      240
ctgccggtca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccggtctt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagccgcctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                 753

<210> SEQ ID NO 211
<211> LENGTH: 251
<212> TYPE: PRT
<213> ORGANISM: Artificial Sequence
<220> FEATURE:
<223> OTHER INFORMATION: Synthetic Lactonase (CL00029160)

<400> SEQUENCE: 211

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

```
Ser Ala Ala Glu Glu Pro Tyr Asp Ile Pro Thr Leu Ala Thr Asp Val
 50                  55                  60
His Glu Thr Leu Ala Gln Leu Ala Glu Asn Asp Val Ile Pro Gly Gly
 65                  70                  75                  80
Leu Pro Ile Ile Val Gly His Ser Met Gly Gly Ile Val Ala Thr Ala
                 85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Ala Glu Gly Met
        115                 120                 125
Leu Arg Gly Ala Asp Phe Pro Val Phe Ile His Gly Met Phe Ala Gln
130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Gly Leu Thr Met
            180                 185                 190
Ile Pro Glu Asp Val Pro Tyr Leu Val Ile Thr Gly Leu Asp Ala Gly
        195                 200                 205
Pro Glu Tyr Ala Ala Trp Leu Gln Arg Glu Ile Pro Gln Ala Val Gln
210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250
```

<210> SEQ ID NO 212
<211> LENGTH: 753
<212> TYPE: DNA
<213> ORGANISM: Artificial Sequence
<220> FEATURE:
<223> OTHER INFORMATION: Synthetic Lactonase (CL00029160)

<400> SEQUENCE: 212

```
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga acgacgtgat ccccggggc      240
ctgccgatca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact cccggtcttc catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgatgatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgaccccgca     720
cggttcgtcg agcgcgtcga ggctttcgtc cgc                                  753
```

<210> SEQ ID NO 213
<211> LENGTH: 251
<212> TYPE: PRT

<213> ORGANISM: Artificial Sequence
<220> FEATURE:
<223> OTHER INFORMATION: Synthetic Lactonase (CL00029162)

<400> SEQUENCE: 213

```
Met Ile Leu Ala His Asp Val Ser Gly Ser Gly Pro Leu Leu Val Leu
1               5                   10                  15
Leu His Gly Ile Thr Glu Asp Arg Arg Ser Trp Asp Pro Val Asp Phe
            20                  25                  30
Thr Lys Gly Phe Thr Val Val Arg Val Asp Leu Arg Gly His Gly Ala
        35                  40                  45
Ser Ala Ala Glu Glu Pro Tyr Asp Ile Pro Thr Leu Ala Thr Asp Val
    50                  55                  60
His Glu Thr Leu Ala Gln Leu Ala Glu Asn Asp Val Ile Pro Gly Gly
65                  70                  75                  80
Leu Pro Val Ile Val Gly His Ser Met Gly Gly Ile Val Ala Thr Ala
                85                  90                  95
Tyr Gly Ala Leu Phe Pro Ala Arg Ala Ile Val Asn Val Asp Gln Pro
            100                 105                 110
Leu Gln Leu Ala Gly Met Gln Gly Gln Val Gln Gln Ala Glu Gly Met
        115                 120                 125
Leu Arg Gly Ala Asp Phe Pro Val Phe Ile His Gly Met Phe Ala Gln
    130                 135                 140
Met Ala Gly Gly Leu Asp Ala Glu Glu Leu Ala Arg Val Asn Gly Ile
145                 150                 155                 160
Arg Ser Pro Arg Gln Asp Val Val Leu Gly Met Trp Arg Pro Leu Leu
                165                 170                 175
Glu Asp Ser Pro Glu Glu Leu Ala Ala Leu Val Ser Arg Leu Thr Arg
            180                 185                 190
Ile Pro Glu Asp Val Pro Tyr Leu Val Ile Thr Gly Leu Asp Ala Gly
        195                 200                 205
Pro Glu Tyr Ala Ala Trp Leu Gln Arg Thr Ile Pro Gln Ala Val Gln
    210                 215                 220
Glu Val Trp Gln Pro Pro Thr His Tyr Pro His Leu Val Asp Pro Ala
225                 230                 235                 240
Arg Phe Val Glu Arg Val Glu Ala Phe Val Arg
                245                 250
```

<210> SEQ ID NO 214
<211> LENGTH: 753
<212> TYPE: DNA
<213> ORGANISM: Artificial Sequence
<220> FEATURE:
<223> OTHER INFORMATION: Synthetic Lactonase (CL00029162)

<400> SEQUENCE: 214

```
atgatcctcg cccacgacgt gtcgggctcc ggcccgctgc tggtcctcct gcacggcatc      60
accgaagacc gccgcagctg ggatccggtc gatttcacca agggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga acgacgtgat ccccgggggc     240
ctgccggtca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcaga ggcgagggga tgctccgcc ggggcggact cccggtgctt catccacggc     420
atgttcgcgc agatggcggg cggcctggat gccgaggagc tggcgcgggt gaatggcatc     480
```

```
cggtctccga ggcaggacgt cgtcctcggg atgtggcggc cgcttctcga ggactcaccc      540
gaagaactgg cggcgctcgt gagccgcctg acgaggatcc cggaggacgt cccgtacctc      600
gtgatcacgg tctcgatgc cgggccagag tacgcggcgt ggctgcagcg accatcccg        660
caggccgtcc aggaggtctg gcagccgccg acccactacc cgcacctcgt cgacccggca      720
cggttcgtcg agcgcgtcga ggctttcgtc cgc                                   753
```

<210> SEQ ID NO 215
<211> LENGTH: 251
<212> TYPE: PRT
<213> ORGANISM: Artificial Sequence
<220> FEATURE:
<223> OTHER INFORMATION: Synthetic Lactonase (CL00029199 G3P)

<400> SEQUENCE: 215

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Lys Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Asn Ala Leu Val Ser Arg Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
                245                 250
```

<210> SEQ ID NO 216
<211> LENGTH: 753
<212> TYPE: DNA
<213> ORGANISM: Artificial Sequence
<220> FEATURE:
<223> OTHER INFORMATION: Synthetic Lactonase (CL00029199 G3P)

<400> SEQUENCE: 216

```
atgatcctcg cccacgacgt gtcgggctcc ggcccgctgc tggtcctcct gcacggcatc      60
accgaagacc gccgcagctg ggatccggtc gatttcacca agggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga cgacgtgat ccccgggggc      240
ctgccggtca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccggtctt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactga cgcgctcgt gagccgcctg acgaggatcc cggaggacgt cccgtacctc     600
gtgatcacgg gtctcgatgc cgggccagag tacgcggcgt ggctgcagcg ggagatcccg     660
caggccgtcc aggaggtctg gcagccgccg acccactacc cgcacctcgt cgacccggca     720
cggttcgtcg agcgcgtcga ggctttcgtc cgc                                  753
```

<210> SEQ ID NO 217
<211> LENGTH: 251
<212> TYPE: PRT
<213> ORGANISM: Artificial Sequence
<220> FEATURE:
<223> OTHER INFORMATION: Synthetic Lactonase (CL00029214)

<400> SEQUENCE: 217

```
Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Asp Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Ile Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
145                 150                 155                 160

Arg Ser Pro Arg Gln Asp Val Val Leu Gly Met Trp Arg Pro Leu Leu
                165                 170                 175

Glu Asp Ser Pro Glu Glu Leu Asn Ala Leu Val Ser Arg Leu Thr Arg
            180                 185                 190

Ile Pro Glu Asp Val Pro Tyr Leu Val Ile Thr Gly Leu Asp Ala Gly
        195                 200                 205

Pro Glu Tyr Ala Ala Trp Leu Gln Arg Glu Ile Pro Gln Ala Val Gln
    210                 215                 220

Glu Val Trp Gln Pro Pro Thr His Tyr Pro His Leu Val Asp Pro Ala
```

```
225                 230                 235                 240
Arg Phe Val Glu Arg Val Glu Ala Phe Val Arg
                245                 250

<210> SEQ ID NO 218
<211> LENGTH: 753
<212> TYPE: DNA
<213> ORGANISM: Artificial Sequence
<220> FEATURE:
<223> OTHER INFORMATION: Synthetic Lactonase (CL00029214)

<400> SEQUENCE: 218
atgatcctcg cccacgacgt gtcgggctcc ggcccgctgc tggtcctcct gcacggcatc      60
accgaagacc gccgcagctg ggatccggtc gatttcaccg acggcttcac ggtcgtgcgg     120
gtcgacctgc gcgggcacgg gcatcagcc gccgaagaac cgtacgacat ccccacgctc     180
gcgaccgacg tgcacgagac cctcgcgcag ctcgccgaga acgacgtgat ccccggggc     240
ctgccgatca tcgtcggcca ctcgatgggc gggatcgtcg cgacggcgta cggcgcgctc    300
ttccccgcgc gggcgatcgt caacgtggac cagcctctcc agctcgcggg catgcagggc    360
caggtgcagc aggcggaggg gatgctccgc gggcggact tcccggtctt catccacggc     420
atgttcgcgc agatggcggg cggcctggat gccgaggagc tggcgcgggt gaatggcatc    480
cggtctccga ggcaggacgt cgtcctcggg atgtggcggc cgcttctcga ggactcaccc    540
gaagaactga acgcgctcgt gagccgcctg acgaggatcc cggaggacgt cccgtacctc    600
gtgatcacgg gtctcgatgc cgggccagag tacgcggcgt ggctgcagcg ggagatcccg    660
caggccgtcc aggaggtctg gcagccgccg acccactacc gcacctcgt cgacccggca    720
cggttcgtcg agcgcgtcga ggctttcgtc cgc                                  753

<210> SEQ ID NO 219
<211> LENGTH: 251
<212> TYPE: PRT
<213> ORGANISM: Artificial Sequence
<220> FEATURE:
<223> OTHER INFORMATION: Synthetic Lactonase (CL00029220)

<400> SEQUENCE: 219

Met Ile Leu Ala His Asp Val Ser Gly Ser Gly Pro Leu Leu Val Leu
1               5                   10                  15

Leu His Gly Ile Thr Glu Asp Arg Arg Ser Trp Asp Pro Val Asp Phe
            20                  25                  30

Thr Lys Gly Phe Thr Val Val Arg Val Asp Leu Arg Gly His Gly Ala
        35                  40                  45

Ser Ala Ala Glu Glu Pro Tyr Asp Ile Pro Thr Leu Ala Thr Asp Val
    50                  55                  60

His Glu Thr Leu Ala Gln Leu Ala Glu Asn Asp Val Ile Pro Gly Gly
65                  70                  75                  80

Leu Pro Val Ile Val Gly His Ser Met Gly Gly Ile Val Ala Thr Ala
                85                  90                  95

Tyr Gly Ala Leu Phe Pro Ala Arg Ala Ile Val Asn Val Asp Gln Pro
            100                 105                 110

Leu Gln Leu Ala Gly Met Gln Gly Gln Val Gln Ala Glu Gly Met
        115                 120                 125

Leu Arg Gly Ala Asp Phe Pro Val Phe Ile His Gly Met Phe Ala Gln
    130                 135                 140

Met Ala Gly Gly Leu Asp Ala Glu Glu Leu Ala Arg Val Asn Gly Ile
```

-continued

```
145                 150                 155                 160
Arg Ser Pro Arg Gln Asp Val Val Leu Gly Met Trp Arg Pro Leu Leu
            165                 170                 175

Glu Asp Ser Pro Glu Glu Leu Ala Ala Leu Val Ser Gly Leu Thr Arg
            180                 185                 190

Ile Pro Glu Asp Val Pro Tyr Leu Val Ile Thr Gly Leu Asp Ala Gly
            195                 200                 205

Pro Glu Tyr Ala Ala Trp Leu Gln Arg Thr Ile Pro Gln Ala Val Gln
    210                 215                 220

Glu Val Trp Gln Pro Pro Thr His Tyr Pro His Leu Val Asp Pro Ala
225                 230                 235                 240

Arg Phe Val Glu Arg Val Glu Ala Phe Val Arg
            245                 250

<210> SEQ ID NO 220
<211> LENGTH: 753
<212> TYPE: DNA
<213> ORGANISM: Artificial Sequence
<220> FEATURE:
<223> OTHER INFORMATION: Synthetic Lactonase (CL00029220)

<400> SEQUENCE: 220
atgatcctcg cccacgacgt gtcgggctcc ggcccgctgc tggtcctcct gcacggcatc      60
accgaagacc gccgcagctg ggatccggtc gatttcacca agggcttcac ggtcgtgcgg     120
gtcgacctgc gcgggcacgg ggcatcagcc gccgaagaac cgtacgacat ccccacgctc     180
gcgaccgacg tgcacgagac cctcgcgcag ctcgccgaga cgacgtgat ccccggggggc    240 ctgccggtca tcgtcggcca ctcgatgggc gggatcgtcg cgacggcgta cggcgcgctc     300
ttccccgcgc gggcgatcgt caacgtggac cagcctctcc agctcgcggg catgcagggc     360
caggtgcagc aggcggaggg gatgctccgc ggggcggact tcccggtctt catccacggc     420
atgttcgcgc agatggcggg cggcctggat gccgaggagc tggcgcgggt gaatggcatc     480
cggtctccga ggcaggacgt cgtcctcggg atgtggcggc cgcttctcga ggactcaccc     540
gaagaactgg cggcgctcgt gagcggtctg acgaggatcc cggaggacgt cccgtacctc     600
gtgatcacgg gtctcgatgc cgggccagag tacgcggcgt ggctgcagcg gaccatcccg     660
caggccgtcc aggaggtctg gcagccgccg acccactacc cgcacctcgt cgacccggca     720
cggttcgtcg agcgcgtcga ggctttcgtc cgc                                 753
```